(12) United States Patent
Castro et al.

(10) Patent No.: US 9,060,862 B2
(45) Date of Patent: Jun. 23, 2015

(54) SEMI-CONSTRAINED BALL AND SOCKET JOINTS

(75) Inventors: Floyd Franklin Castro, Oakland, CA (US); James Mark Oakley Fisher, Walnut Creek, CA (US); Alex Paul Moskovitz, Berkeley, CA (US)

(73) Assignee: Floyd Franklin Castro, Oakland, CA (US)

( * ) Notice: Subject to any disclaimer, the term of this patent is extended or adjusted under 35 U.S.C. 154(b) by 0 days.

(21) Appl. No.: 13/544,479

(22) Filed: Jul. 9, 2012

(65) Prior Publication Data

US 2013/0013079 A1 Jan. 10, 2013

Related U.S. Application Data

(60) Provisional application No. 61/505,970, filed on Jul. 8, 2011.

(51) Int. Cl.
| | |
|---|---|
| *A61F 2/30* | (2006.01) |
| *A61F 2/32* | (2006.01) |
| *A61F 2/40* | (2006.01) |
| A61F 2/34 | (2006.01) |
| A61F 2/36 | (2006.01) |
| A61F 2/08 | (2006.01) |

(52) U.S. Cl.
CPC ... *A61F 2/30* (2013.01); *A61F 2/32* (2013.01); *A61F 2/40* (2013.01); *A61F 2002/30433* (2013.01); *A61F 2002/30462* (2013.01); *A61F 2002/30604* (2013.01); *A61F 2002/30649* (2013.01); *A61F 2002/30652* (2013.01); *A61F 2002/3233* (2013.01); *A61F 2002/3401* (2013.01); *A61F 2002/3038* (2013.01); *A61F 2002/30624* (2013.01); *A61F 2002/30635* (2013.01); *A61F 2002/3064* (2013.01); *A61F 2002/30647* (2013.01); *A61F 2002/3461* (2013.01); *A61F 2002/3469* (2013.01); *A61F 2002/3491* (2013.01); *A61F 2002/3617* (2013.01); *A61F 2/08* (2013.01)

(58) Field of Classification Search
CPC ............... A61F 2/30; A61F 2/32; A61F 2/38; A61F 2/40
USPC ..................... 623/19.11–20.13, 22.11–22.39, 623/23.39–23.43
See application file for complete search history.

(56) References Cited

U.S. PATENT DOCUMENTS

| | | |
|---|---|---|
| RE28,895 E | 7/1976 | Noiles |
| 4,123,806 A | 11/1978 | Amstutz et al. |
| 4,159,544 A | 7/1979 | Termanini |
| 4,770,661 A | 9/1988 | Oh |

(Continued)

*Primary Examiner* — Yashita Sharma
(74) *Attorney, Agent, or Firm* — Alex P. Moskovitz, Esq.

(57) ABSTRACT

Regarding semi-constrained artificial ball (head) and socket (cup) joints such as the hip or shoulder joint, which allow for certain numbers of degrees of rotation along three independent axes. For example, one embodiment creates at least two axes of rotation through a super-spherical space carved out of the inner surface of the cup, with a cup-cable connecting two points along the super-spherical space, and a perpendicular head-cable looping around the head and the cup-cable within the super-spherical space, and with the head-cable residing in a groove. Another embodiment creates two axes of rotation through a combination of a 1) swivel with lever and/or 2) cable attached to a circular track (with the knob or ring around cable facing inward or outward), both of which have the center of the head as the center of rotation. The third axis may be created by a horizontal swivel and by wiggle room.

29 Claims, 48 Drawing Sheets

(56) References Cited

U.S. PATENT DOCUMENTS

| | | |
|---|---|---|
| 4,960,427 A | 10/1990 | Noiles |
| 5,007,936 A | 4/1991 | Woolson |
| 5,092,897 A | 3/1992 | Forte |
| 5,127,920 A | 7/1992 | MacArthur |
| 5,192,329 A | 3/1993 | Christie et al. |
| 5,556,434 A | 9/1996 | Epstein |
| 5,951,605 A | 9/1999 | Dennis et al. |
| 5,989,293 A | 11/1999 | Cook et al. |
| 5,989,294 A | 11/1999 | Marlow |
| 6,010,535 A | 1/2000 | Shah |
| 6,042,611 A | 3/2000 | Noiles |
| 6,042,612 A | 3/2000 | Voydeville |
| 6,129,765 A | 10/2000 | Lopez et al. |
| 6,156,069 A | 12/2000 | Amstutz |
| 6,228,122 B1 | 5/2001 | McGann |
| 6,248,132 B1 | 6/2001 | Harris |
| 6,299,647 B1 | 10/2001 | Townley |
| 6,503,281 B1 | 1/2003 | Mallory |
| 6,527,808 B1 | 3/2003 | Albertorio et al. |
| 6,923,833 B2 | 8/2005 | Wasielewski |
| 6,986,792 B2 | 1/2006 | McLean et al. |
| 7,022,142 B2 | 4/2006 | Johnson |
| 7,074,241 B2 | 7/2006 | McKinnon |
| 7,160,332 B2 | 1/2007 | Frederick et al. |
| 7,169,186 B2 | 1/2007 | Harris et al. |
| 7,179,296 B2 | 2/2007 | Dooney |
| 7,192,449 B1 | 3/2007 | McQueen et al. |
| 7,335,231 B2 | 2/2008 | McLean |
| 7,780,737 B2 | 8/2010 | Bonnard et al. |
| 2001/0032021 A1 | 10/2001 | McKinnon |
| 2003/0120347 A1 | 6/2003 | Steinberg |
| 2004/0199257 A1 | 10/2004 | Dooney |
| 2007/0106392 A1 | 5/2007 | Servidio et al. |
| 2007/0276364 A1 | 11/2007 | Hvolris |
| 2009/0088853 A1 | 4/2009 | Ogilvie et al. |

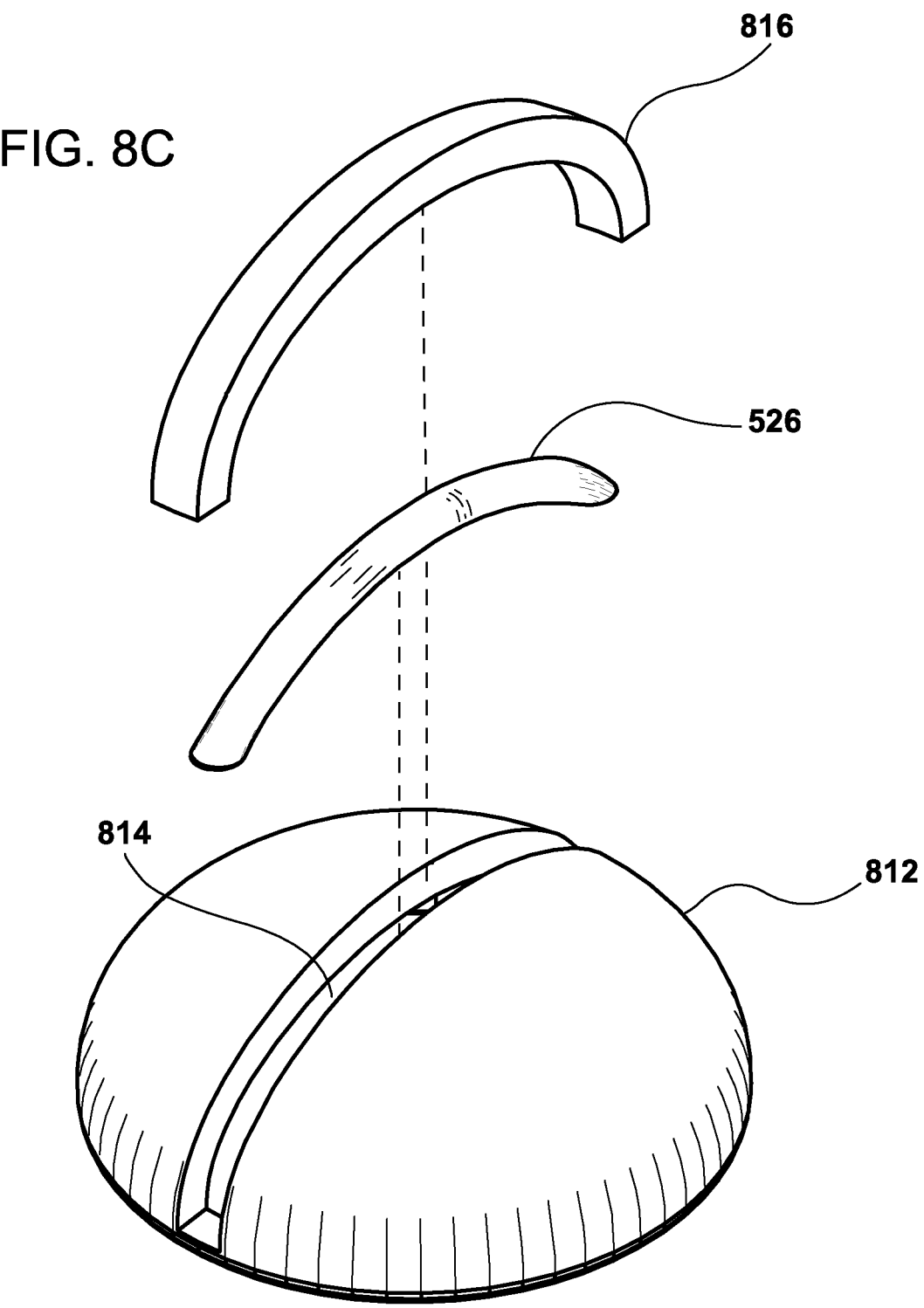

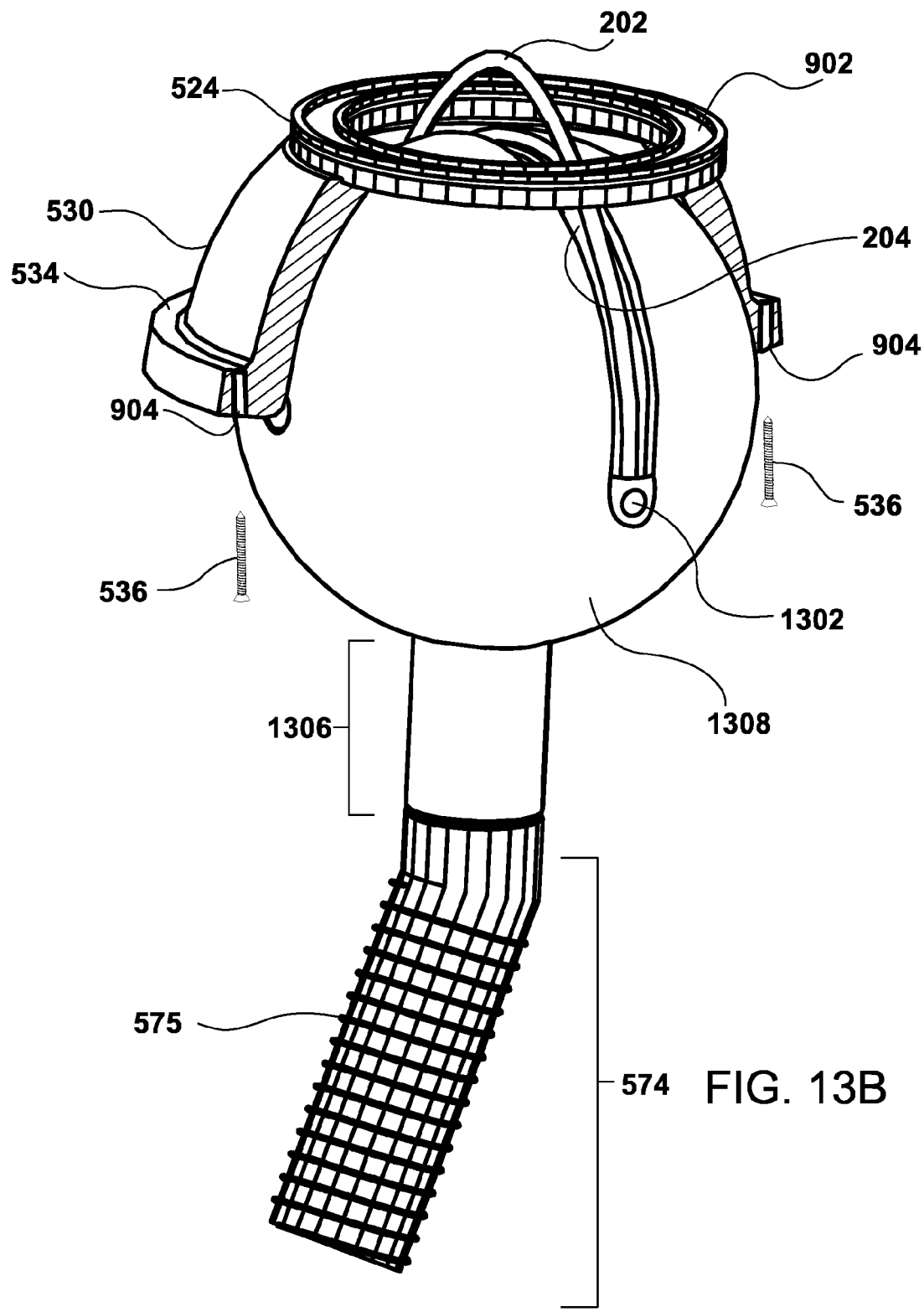

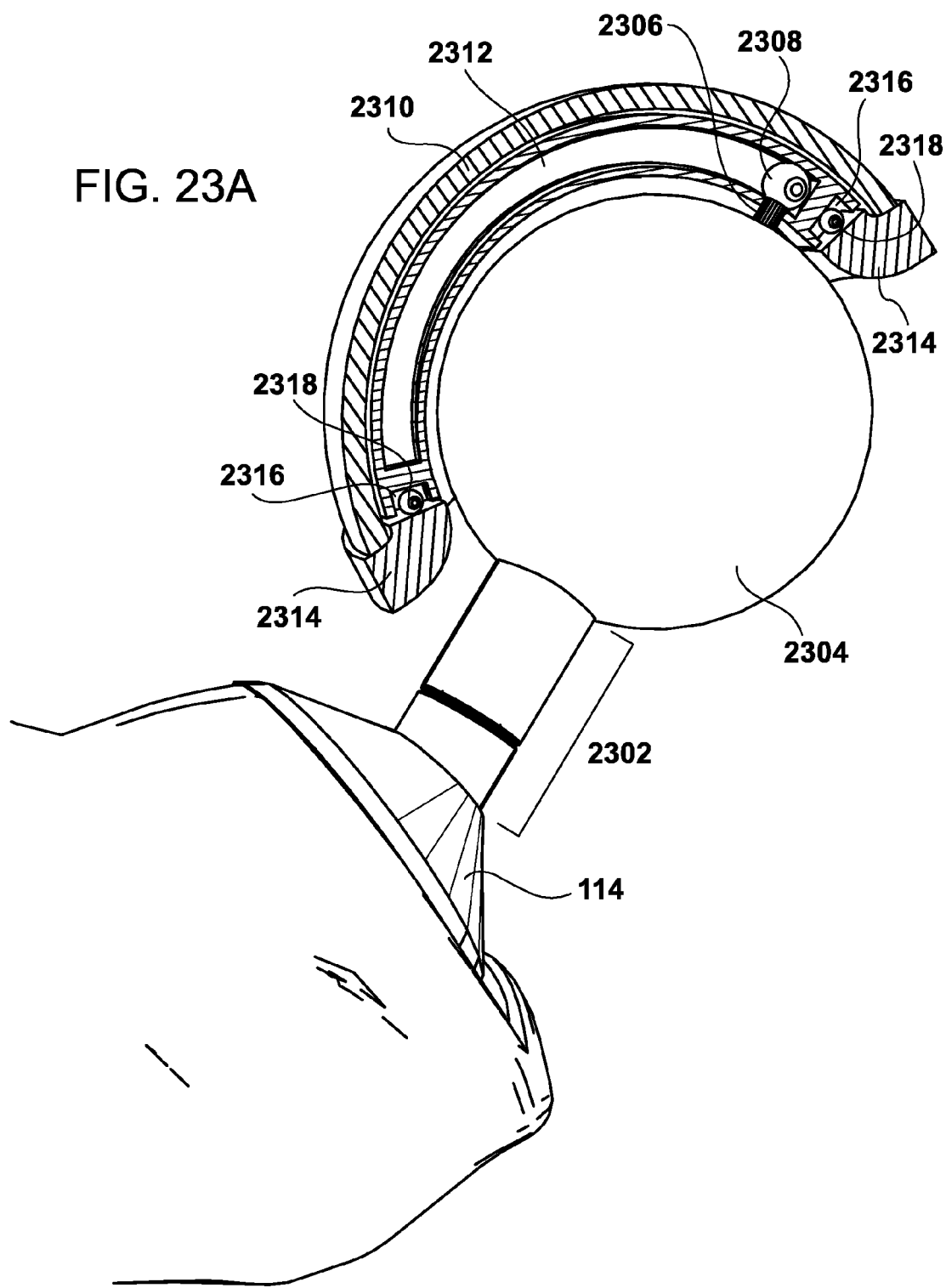

SEMI-CONSTRAINED BALL AND SOCKET JOINTS

CROSS REFERENCE TO RELATED APPLICATIONS

This application claims the benefit of U.S. Provisional Application No. 61/505,970, filed Jul. 8, 2011, of the same title and same inventors.

BACKGROUND

Natural ball and socket joints (such as hip (FIG. 1) and shoulder joints (FIG. 2)) allow for certain degrees of rotation along three independent axes. For instance, you can kick your leg forward/backward, outward/inward, and twist your leg. (The ball in that instance is the end of the femur that fits inside the enclosing socket of the hip.) Older adults and others in need of artificial ball and socket joints (such as hip and shoulder replacements) wish to maximize range of movement without a high risk of dislocation of the ball from the socket. Furthering this goal allows the prosthetic bearer to, among other things, participate maximally in fitness that can help prevent one's health from deteriorating, and also to avoid painful corrective surgeries that further disrupt the ball and socket connection and risk even further dislocation. Thus, there is an extremely substantial need for a prosthetic apparatus that allows for maximal range of rotational movement without dislocation.

There have been many attempts to constrain the ball to the socket in the past: For instance, U.S. Pat. Nos. 7,780,737; 7,766,971; 7,749,277; 7,335,231; 7,192,449; 7,179,298; 7,179,296; 7,169,186; 7,160,332; 7,144,427; 7,115,145; 7,074,24; 7,022,142; 6,986,792; 6,923,833; 6,527,808; 6,299,647; 6,042,612; 6,042,611; 5,916,270; 5,782,930; 5,639,280; 5,556,434; 5,092,897; 5,062,823; 4,960,427; 4,770,661; 3,996,625; U.S. Applications 20100174380; 20100087930; 20080125866; 20090088853 20070225818; 20070135927; 20070106392; 20070106389; 20060241780; 20060101; 20030050703; 20030191537; 20030212458; 20010032021. However, all are limited either in rate of dislocation or in range of smooth motion. Thus, this extremely substantial need for a prosthetic ball and socket apparatus that allows for maximal range of motion along each of the planes of rotation and along the line of twisting without dislocation has gone unmet for quite some time.

SUMMARY

Versions of the invention allow for increased degrees of rotation of a head-bone (such as a femur 112 or a humerus 402) along three independent axes relative to the cup-bone (such as a hip-bone 102 or a shoulder framework 404), while still constraining the head-bone from dislocation from the cup-bone.

First, to explain some terms—imagine the head as an earth viewed from space, with an equator, a north pole, south pole, northern hemisphere, latitudinal lines (running sideways), longitudinal lines (running north and south). Now imagine a head from the preferred embodiment from the first version 108 inside a socket 104 of a cup 106 (see FIG. 12). The head's north pole 1202 is closest to the apex of the inner surface of the cup 702 (though when the head 108 rotates, the head's north pole 1202 rotates). The apex of the inner surface of the cup may also be referred to as "the north pole of the inner surface of the cup." The head's south pole 1204 is furthest from the apex 702 of the inner surface of the cup 802. The head's equator 1206 contacts where the rim of the inner surface of the cup 532 meets the head 108 through the cup-liner 531 (except when the head 108 rotates). In neutral position (when the head 108 has not articulated in any directions yet), the cup's north pole 514 and equator 532 are at approximately the same point as the head's north pole 1202 and equator 1206 (this is not true when the head 108 has rotated along either the line of a cup-cable 526 or perpendicularly along the line of a head-cable 202). Usable head rotation means geometries of various parts that when combined into an embodiment and/or version, allow for head rotation that satisfies a particular function (walking default, alternatively normal movement, or movement sufficient to do a particular activity and/or other functions), and obviously does not break down after a week of use (alternatively, nor does it lead to excess buildup of toxic material, for example metal debris leaching out into the body resulting from metal on metal rubbing). For instance, the term "horizontal" (usually used in context of a "horizontal swivel") means latitudinal enough for usable head rotation (the term horizontal is defined alternately and more specifically below).

FIGS. 1-12 all depict an embodiment (which is the preferred embodiment of the first version and of all versions) of the first version. This version comprises (see FIG. 5, and also FIG. 2 for most parts) A) a head to head-bone rod 218 (with one end to be inserted into the head-bone such as a femur 112 or a humerus 402, and a second end connected to a head 108), B) the head 108 and C) a cup 106 encircling the head 108, with the cup 106 to be inserted into the cup-bone (such as the hip-bone 102 or the shoulder framework 404), and D) a cup-liner 531 interposed between the cup 106 and the head 108.

For the first version:

A. The head to head-bone rod 218 fastens at one end to "roughly the south pole of the head", and at the other end comprises a rod to be inserted into the head-bone. (See for example FIG. 2). ["Roughly the south pole of the head" means close enough to the south pole of the head to allow for usable head rotation.] Alternatively, the head to head-bone rod can attach to the south pole (without the "roughly" qualification), or anything in between roughly and exactly. If the head-cable 202 passes through "about the head's south pole", ["about the head's south pole" means close enough to the south pole to allow for usable head rotation] then the head to head-bone rod 218 has a hole roughly at the south pole end of the head 1204 to allow the head-groove 204 and head-cable 202 to pass through about the south pole 1204. (See FIG. 9).

B. The head: The head 108 is "roughly a ball shape" [meaning having spherical portions of the surface of the head 108 that allow it to fit snugly within the spherical portions 506 of the inner surface of the cup 802, even when the head 108 is rotated along any axis allowed to any number of degrees allowed (in the context of all of the parts put together), as well as having room for the cup-cable 526 within the super-spherical cavity 804] that fits inside the cup 106 and contacts the spherical portions 506 of the inner surface of the cup 802 through the cup-liner 531. "A head fitting inside the inner surface of the cup" means the same thing as "roughly a ball shape". The phrase "contacting the spherical portion of the inner surface of the cup" contemplates direct contact with the spherical portion of the inner surface of the cup and/or indirectly through a cup-liner. Ideally, the head contacts all spherical portions of the inner surface of the cup, but alternatively, the head contacts enough spherical portions to allow for usable head rotation or more.

The head 108 has a "roughly longitudinal groove" [meaning sufficiently longitudinal to allow for usable rotational movement of the head 108 along the cup-cable 526 axis in both directions and defined as a "head-groove" 204] looped around the circumference of the head 108 running "roughly pole to pole" [meaning both 1) going from the north pole of the head 1202 to the south pole 1204 and back, and 2) changing direction in its loop from northward to southward (and vice versa), closely enough to each pole to allow for usable head rotation, including but not limited to rotational movement of the head 108 along the cup-cable 526 axis in both directions]. Alternatively, the head-groove may be completely longitudinal and run completely pole to pole, or anything in between this exactitude and that allowing for usable head rotation. The phrase "fitting inside the head-groove when the head-cable is between the head and the spherical portion of the inner surface of the cup" means that those portions of the head-cable that are currently between the spherical portion of the inner surface of the cup and the head are inside the head-groove so as not to get caught or pinched between the head's spherical surface and the spherical portion of the inner surface of the cup. Alternatively, the head-cable can be "looping around a portion of the head", where the head cannot move translationally away from the inner surface of the cup's north pole without the head-cable tightening, or catching. This serves the same purpose of constraining the head translationally as when the head-cable is "attaching to the head" at at least two ends.

Note that while ball-bearings 602 are included in the preferred embodiment between the head 108 and the head-cable 202, allowing the head 108 to rotate independently of the head-cable 202, thus allowing the head-cable 202 to maintain its shape when it loops around the cup-cable 526, thus obviating the need for the head-cable 202 to be flexible, that if the head-cable 202 is flexible, then it can change its shape as the stretch of head-cable forming the loop around the cup-cable 526 changes. (This change in shape can also allow the head 108 to potentially rotate further than if the head-cable 202 was straight—see for example FIG. 11D showing the head-cable line rotating further along the head 108 than in the superspherical cavity 804—see also FIG. 16D.) Additionally, even if the head-cable 202 is not flexible, and the head 108 did not rotate independently from the head-cable 202, there would still be wiggle room before either an end of the loop of the head-cable 108 hit the cup 106 or the head-cable 108 caught on the cup-cable 526.

In another embodiment, a sheath 1304 encloses the head-cable 202 for a portion of the head-cable 202 that does not need to come out of the head-groove 204 to begin to loop around the cup-cable 526 (optionally and preferably all of the length not needing to come out of the groove) during usable head rotation (see FIG. 13A).

In yet another embodiment (see FIGS. 15A-15B), the swerving head-cable 1502 and/or swerving head groove 1506 in the accommodating head 1504 do not go around the south pole 1204 of the head 1504, though the swerving head-cable 1502 does make a complete loop (no breaks in the swerving head-cable 1502), obviating the need for a hole 570 between the stem 110 and the south pole of the head 1204, making the formerly pronged portion 564 into a non-pronged portion 1306. Again, the geometry of the swerve around the south pole of the head 1204 must 1) allow for usable head rotation and 2) if no sheath (similar to the sheath 1304 in FIG. 13A) is used around the swerving head-cable 1502, not allow for the swerving head-cable 1502 to slip out of the swerving head-groove 1506 during usable head rotation.

In yet another embodiment (see FIG. 13B), the head-cable 202 and/or head-groove 204 do not go all the way down to the south pole of the head 1204 and loop around it, but attach 1302 to the accommodating head 1308 at certain latitudes above the south pole of the head 1204 at each end. The latitudes at each end attached must allow for usable head rotation.

In yet another embodiment (see FIGS. 14A-14B), the head-cable is forked 1406 (with accommodating forked head-groove 1404) around the south pole of the head 1204, again obviating the need for a hole 570 between the stem 110 and the south pole 1204 of the head 1402, making the formerly pronged portion 564 into a non-pronged portion 1306. Again, the geometry of the swerve around the south pole of the head 1204 must 1) allow for usable head rotation and 2) if no sheath (similar to the sheath 1304 in FIG. 13A) is used around the forked head-cable 1406, not allow for the forked head-cable 1406 to slip out of the forked head-groove 1404 during usable head rotation.

In yet another embodiment (see FIGS. 16A-16B), instead of one head-cable 202, a number one head-cable 1604 in a number one head-groove 1606 is used on one side of the south pole of the head 1204, and a number two head-cable 1608 in a number two head-groove 1610 in an accommodating head 1602 is used on the other side of the south pole of the head 1204, again obviating the need for a hole 570 between the stem 110 and the south pole of the head 1204, making the formerly pronged portion 564 into a non-pronged portion 1306. Again, the geometry of each head-cable around the south pole of the head 1204 must 1) allow for usable head rotation and 2) if no sheath (similar to the sheath 1304 in FIG. 13A) is used around the number one head-cable 1604 or the number two head-cable 1608, not allow for either head-cable to slip out of the head-groove 1610 during usable head rotation. Note that any number of head-cables may be used, so long as they allow for usable head rotation. It is best (and optional) to have the head-cables parallel and close to the north pole-south pole line of the head 1602, but they may be non-parallel and/or further apart if they still allow for usable head rotation.

In yet another embodiment (see FIG. 17), the above embodiment (in the previous paragraph) with multiple head-cables is changed by replacing the cup-cable 526 with two mini-cup-cables 1702. Again, the geometry must allow for usable head rotation. It is optionally useful to have stretchable head-cables to obtain more degrees in the range of motion along each axis.

In yet another embodiment (see FIG. 20), a shortened head-cable 2004 does not have any head-groove 204 but attaches to the accommodating head 2002 at two points 2006 in the northern hemisphere of the accommodating head 2002, again obviating the need for a hole 570 between the stem 110 and the south pole of the head 1204, making the formerly pronged portion 564 into a non-pronged portion 1306. Optimally, the shortened head-cable 2004 attaches at each end at 45 degrees from the north pole of the head 1202 on opposite sides of the north pole, so as to allow the head 2002 to rotate 45 degrees in each direction along the line of the shortened head-cable 2004 before either 1) the attachment point 2006 of the head-cable 2004 bangs into the inner surface of the cup 804, or 2) the shortened head-cable 2004 catches on the cup-cable 526.

In yet another embodiment (see FIG. 2106), instead of using a head-cable 202 and cup-cable 526, a head-cup-cable 2104 connects the inner surface of the cup 802 to the accommodating head 2102 with attachment point 2106 (optionally and preferably connecting the north pole of the head to the north pole of the cup, for maximum range of motion in all directions). It is useful for the head-cup-cable 2104 to be stretchable and have room to unfold itself and become longer (like a snake uncurling), so as to increase the range of motion, so long as it does not get tangled within itself.

Note again that the above embodiments not needing a hole 570 for the head-cable 202 have an un-pronged portion 1306 attaching the stem to the south pole of the head 1204. All of these embodiments optionally but optimally have cables parallel to the north-south pole line and as close to it as possible (excepting for a strong enough stem for usable head rotation).

If it is not necessary for the head-cable to slide linearly relative to a head-groove, then the head-cable must just fit these requirements: 1) it must be able to loop around the cup-cable(s) during usable head rotation; 2) it must not catch at the cup's equator between the head and the inner surface of the cup (through the cup-liner).)

Though not optimal, it is not necessary for the head-cable to be in the head-groove all of the way along the head (aside from looping around the cup-cable), so long as usable head rotation is obtained.

Though the cup 106 is shown in the figures extending to the equator of the head and no further, the cup can extend down beyond the equator of the head into the southern hemisphere, so long as usable head rotation is obtained. This can be used as an additional safeguard to keep the head from dislocating from the socket, but sacrifices range of motion to the extent it encircles the head.

B. The cup: The cup 106 is comprised of an inner surface 802 and an outer surface 511, the outer surface 511 fastened to the cup bone (for example, hip bone 102 or shoulder framework fitting around the cup 404) and the head 108 fitting within the cup's inner surface 802. The inner surface is comprised of a spherical portion 506 and a super-spherical (hollowed out beyond spherically) portion 508. (See for example FIG. 5 for components mentioned in this paragraph).

Optionally and preferably the super-spherical portion 508 of the inner surface of the cup 802 viewed from the side is a portion of a circle with its center the same as the spherical portion 506 but with a larger radius, also optionally with sides that jut inward allowing the cup-cable 526 to contact the inner surface of the cup 802 at a perpendicular angle. However, so long as the super-spherical cavity 804 allows room for the head-cable 202 to loop around the cup-cable 526 and rotate for usable rotation, there is enough concavity in the super-spherical cavity 804].

Spherical Portion:

The spherical portion 506 of the inner surface of the cup 802 "runs roughly all of the way around the inner surface of the cup along latitude lines, is located roughly closer to the cup's equator than the super-spherical portion, and extends approximately up from the equator to a certain latitude on the inner surface of the cup" [meaning also covering enough surface area along the head's equator 1206 to accomplish the following: 1) once fitted into the spherical portion 506 of the socket/cup, the head 108 cannot move translationally further into the socket; and 2) the surface area of the portion where the head 108 contacts the cup-liner 531 is sufficient such that any debris buildup caused by rubbing of the head 108 and the inner surface of the cup 802 against the cup liner 531 does not unduly impair operation of the apparatus nor the patient's health to render the hip implant unsafe to implant]. Alternatively, the "inner surface wherein a portion of the inner surface running from the cup's equator to a more northerly latitude" is defined to runs all of the way around the inner surface of the cup along latitude lines, extends upward from the cup's equator to a particular latitude (for example, 5, 10, 20, 45 degrees upward from the cup's equator, these examples not meant to be limiting).

Super-Spherical Portion:

The super-spherical portion 508 of the inner surface of the cup 802 "runs roughly all of the way around the cup along latitude lines, is located roughly closer to the cup's north pole, and extends down approximately from the inner surface of the cup's north pole to said certain latitude on the inner surface of the cup" [meaning also covering enough surface area to allow usable rotational movement both along the line of the cup-cable 526 and along the line of the head-cable 202]. Alternatively, there can be "a portion of the inner surface running from the more northerly latitude to the north pole of the cup", wherein the super-spherical (same meaning as "hollowed out super-spherically") portion runs all of the way around the cup along latitude lines, and runs down latitudinally from the north pole of the inner surface of the cup to the latitude at which the spherical portion begins.

Connecting the Cup to the Cup-Bone:

The cup 106 is fastened to the cup-bone, either directly or indirectly through a mounting plate 302 (or other combination of parts) encapsulating the cup 106 (optionally and preferably with two screws into the cup-bone, and the cup 106 connecting to the mounting plate 302 through male and female locking grooves).

In yet another embodiment (See FIGS. 22A-C), the portions of the cup 106 along the cup's equator are recessed along the line of the head-cable 202 (with one recess 2202 at one side, and another recess 2204 on the opposite side), allowing the stem 110 room to swing up beyond 180 degrees (see FIG. 22B). Note that the cup-liner 531 must also be similarly recessed.

Optionally, the cup liner 531 lines at least the spherical portions 506 of the inner surface of the cup 802 and contacts the inner surface of the cup 802 on one side and the head on the other side. (See for example FIGS. 3, 5).

Optionally, a locking ring for the cup liner holds the cup liner in place, such as found in U.S. Pat. No. 7,766,971.

The cup-cable 526 runs "roughly parallel to the surface of the head above the north hemisphere and roughly perpendicular to the head-groove" [meaning parallel enough to the surface of the head and perpendicular enough relative to the head-groove to allow for usable head rotation], attached at each end at a point on the super-spherical portion of the inner surface of the cup (optionally with a lip that allows the cup-cable to contact the inner surface of the cup at a perpendicular angle). (See for example, FIGS. 13A-B). Alternatively, the cup-cable can run exactly parallel to the surface of the head above the north hemisphere.

Cup-Cable/Head-Cable Interface:

In yet another embodiment (see FIGS. 18-19), the head-cable 202 can slide linearly relative to an interface 1802, while the cup-cable 526 can also slide linearly (though perpendicular to the head-cable) relative to the interface 1802. This allows the distance between the cup-cable 526 and the head-cable 202 to remain fixed for easier motion. The interface 1802 is composed of 1) a subunit 1804 with a hole 1808 for the head-cable 202 housing a roller bearing above the head-cable 1902 and a roller bearing below the head-cable 1904; and 2) a subunit 1806 with a hole 1810 for the cup-cable 526 housing a roller bearing above the cup-cable 1906 and a roller bearing below the cup-cable 1908. Note that any number of roller bearings (or other bearings such as ball-bearings, or sets of bearings) may be used, so long as the head-cable 202 and cup-cable 526 each can slide independently. It is also possible to have only the cup-cable 526 able to slide if ball-bearings in the head-groove allow the head to rotate independently of the head-cable.

More on the Swivel:

The swivel allows the head-bone to rotate along the z-axis (when you twist your leg (for the hip joint) or twist your shoulder (for the shoulder joint) in the axis pointing from the inner surface of the cup's north pole down to the head-bone, discussed earlier as "latitudinally"). Rotation along this z-axis is called "horizontal", resulting in the term "horizontal swivel." The swivel may be horizontal, or roughly horizontal enough to allow for usable head rotation, or anything in between. The swivel may be at any workable point between the head-bone and the cup-bone—thus, if it does not interfere with the functioning of the other parts of the apparatus, such points which should be obvious to one of ordinary skill in the art. For instance, the swivel also may be between the inner surface of the cup 802 and the cup-bone (for example, the hip bone 102 or the shoulder framework 404), or between the inner surface of the cup 802 and the head 108, or between the south 1204 pole of the head and the head-bone (for example, the femur 112 or the humerus 402), or bisecting the head 108 (so long as it doesn't interfere with the head-cable 202 sliding in any head-grooves 204, and is sufficiently strong so that the part adjacent to the swivel closer to the cup-bone (for example, the hip bone 102 or the shoulder framework 404) remains "substantially fixed" [meaning not susceptible to breakage or unusable bending] (aside from the horizontal twisting afforded by the swivel) relative to the part adjacent to the swivel further from the cup-bone (for example, the hip bone 102 or the shoulder framework 404)). The swivel is optional, as the head 108 may still swivel horizontally before the head-cable 202 runs into the cup-cable by becoming less perpendicular to each other.

It should be obvious to one of ordinary skill in the art, using the main concepts and the first version to work off of, to make and use different versions using a) various means of connection (instead of screws, substituting other ways of connecting the parts); b) splitting a given part into multiple parts (for instance, to allow for assembly of most parts outside of the body, and to allow parts to be more easily replaced (for instance, so the bone doesn't have to be drilled into)), and/or combining parts; c) varying numbers along ranges (for instance, the size of the head, exact shape of super-spherical cavity so long as it performs its function, exact latitude at which the inner surface of the cup shifts from super-spherical to spherical, exact placement and design of the horizontal swivel, among others); and/or d) omitting features so long as the function of usable head rotation is still served. While different type heads (or other parts) are referred to throughout, the usage of a specific reference numeral (such as 108) is not meant to constrain the meaning if other geometries (including but not limited to parts from other embodiments and/or other versions) are workable within the general inventive concept, but just to be an example.

It should be obvious to a person of ordinary skill in the art how to assemble any of the previously mentioned versions, with the following additional tips:

1. To assemble the head 108/head-cable 202/head to head-bone rod 218 complex when there is a south pole hole in the end of the head to head-bone rod 570 which the head-cable 202 and head-groove 204 fit through, the head to head-bone rod 218 may have two prongs 571 that fit into the head 108 at the south pole of the head 1204, where the head-cable 202 loops around the beginnings of the prongs in the prongs hole 570 and turns along with the prongs 571 until the prongs 571 are fully screwed in. (One alternative (not in preferred embodiment) would be if the head-groove 204 is to completely loop around the south pole of the head 1204, then after the head-cable 202 is inserted between the two prongs 571, then a piece with head-groove portion 577 facing the beginnings of the prongs 571 could be attached between the two prongs to complete the head-groove 204 between the prongs 571.) Or, instead of looping the head-cable 202 around prongs 571 in the head-head-bone rod 218 before the prongs 571 are screwed into the head 108, a section of one of the prongs 571 could be cut out and replaced (or just put in) after sliding the head-cable 202 between the two prongs 571. There are many other methods of assembling these parts, which should be obvious to one of ordinary skill in the art.

2. To loop the head-cable 202 around the cup-cable 526 while both will eventually end up in a covered cavity 804 between the inner surface of the cup 802 and the northern hemisphere of the head, there must be a hole adequate to allow the cup-cable 526 to be inserted properly between the head-cable 202 and the head 108 (if the preferred embodiment method detailed above of squeezing the cup-cable 526 between two parts of the cup 106 is not used)—with (see FIG. 8B) a hole 808 at either end of where the cup-cable 526 attaches with an accommodating cup 810 to the cup, or (see FIG. 8C) closer to the top of the cup, beginning with an accommodating cup 812 with an accommodating hole in the top 814 through which first the cup-cable 526 fits into the cavity 804 and then the hole 814 is closed by an accommodating piece 816 to fit into the cup 812.

Any number of variations of the above two methods of assembly, and/or other methods, should be obvious to one of ordinary skill in the art.

Each version may be used to create independent axes of rotational movement (through a combination of rotation along the line of the head-cable 202 (see FIGS. 11A-11B examples), along the line of the cup-cable 526 (see FIGS. 11C-11D), and twisting through the swivel—alternately using the natural twisting allowed by the head-cable and cup-cable instead of the swivel), while still constraining the head translationally relative to the cup. The degrees of rotation along each axis are limited by physical constraints—ie when one part (such as a head-cable 202) runs into another part (such as the inner surface of the cup 802).

In another version, each axis of rotation is created piecemeal through "swivel devices" that form a device assembly (which connects the cup-bone (such as the hip bone 102 or the shoulder framework 404) to the head-bone (such as the femur 112 or the humerus 402).

Each axis of rotation is created piecemeal through a "swivel device" that rotates around where the center of the head 108 would be, either through 1) a swivel with a lever (see for example FIGS. 30A-C), comprising a swivel whose axis of rotation crosses through the center of the head with a lever 3004 extending perpendicular to said axis of rotation and outward from the center of where the head 108 would be, or 2) a cable that is caught within but slides smoothly along a circular track along a fixed radius from the center of the head (optionally with ball bearings interfacing between the cable caught in the track and the track), the cable being a permutation of the variables a) inside the head track (top left of FIGS. 26, 29) vs. along the cup track (top left of FIGS. 27, 28) and b) type of track (for instance, knob inside track (top left of FIGS. 26, 27) or ring around cable (top left of FIGS. 29, 28)). To create two independent axes of rotation, the axis about which each device rotates is perpendicular to the other device's axis. Note that each device may be attached to separate sides of the head (see for example FIGS. 24A-24B, 31A-31B), or to each other (see for example top left of FIG. 25A)—the only constraint when selecting devices is that the lever device (see for example FIGS. 30A-30C) may only be used when pointing outward from the head's center. Each device or combination (when the devices are not on separate sides of the head but are connected to each other) of devices attaches the head to either the head-bone or to the cup-bone, and the connection between the head and the bone not connected by a combination (the cup-bone or the head-bone, if two separate devices are not used) does not have to rotate (but may, such as through another device).

Adding more devices even after two axes of rotation were already created may be used to get extra degrees of rotation (such as by having both the head-bone and the cup-bone each separately attached to cables that insert along the same track (along the same axis of rotation, allowing for possibly more than 180 degrees of rotation along that axis)). (For example, see FIGS. 25A-C, where two knobs are both in a track 2313 in the head).

Swivel with Lever:

FIGS. 30A-30C depict the preferred embodiment of a swivel with lever 3004 (see FIGS. 30B-30C for inner parts). An accommodating head 3006 (with optional fixed point 3008 on opposite side of head 3006) is adapted to fit a swivel with lever 3004 extending perpendicular to axis of rotation and outward from the center of the head 3006, the swivel comprising the lever 3004 which is rotated by a ring 3002 that rotates about the center portion 3012 attached the head 3006 through ball-bearings 3014. The accommodating head 3006 contains a slot so that the lever 3004 can rotate a certain number of degrees without being stopped by the accommodating head 3006.

Inside Track:

An inside track is where something is caught within but slides smoothly along a circular track along a fixed radius from the center of the head, and where the fixed point is further away from the center of the head (for instance on the cup) than the track. For example, 1) (see for example, FIG. 27) a dumbbell portion with knob 2320 in track 2313 and stick portion 2306 extending to fixed points at the cup 2702 and on the bottom 2504 (optionally with ball-bearings 2704) (see FIG. 27, two knobs 2320) the inside of the head 2502 or 2) (see for example, FIG. 29) a ring 2904 around a cable 2906 in a slot 2902 on the inside of the head 2908.

Outside Track:

An outside track is where something is caught within but slides smoothly along a circular track along a fixed radius from the center of the head, and where the fixed point is closer to the center of the head (for instance in the head). For example, 1) (see for example, FIG. 26) a dumbbell portion with knob 2308 in track 2312 and stick portion 2306 extending down towards the center of the accommodating head 2604 (optionally with ball-bearings 2606 and with optional fixed point 2602 on the other side of accommodating head 2604) or 2) (see, for example, see FIG. 28) a ring 2804 around a cable 526 in a slot 2806 on the accommodating cup 2808.

A horizontal swivel (with an axis perpendicular to that of the two devices) may be created just as in the cables version (see for example FIG. 28). Unlike some of the cables embodiments, a swivel bisecting the head will not interfere with the operation of any cable, because there is none.

As with the cables version, there are many ways of implementing the details of the piecemeal version, such as number of parts (such as more sets of ball-bearings for lever), type of parts (such as using roller-bearings instead of ball-bearings), geometry (does not have to be exact so long as the function of usable head rotation is fulfilled) and any other factor obvious to one of ordinary skill in the art.

Alternatively to the piecemeal version, two or three axes of rotation may be created through a gimbal for each axis of rotation (optionally with a flexible cover). (For example, see FIG. 32). The third axis is created through a horizontal swivel as above.

Additionally, one track combined with a horizontal swivel may create two axes of rotation by acting like a weathervane (for example, see FIGS. 23A-23B). For example, an outside track with a knob (see FIGS. 23A-23B) can rotate along one axis. If the pressure on the left side of the head is different from that on the right side of the head 2304, then the head 2304 will swivel more and more until it reaches the point where it is only rotating about the axis of the track 2312.

Assembly of the piecemeal and track versions should be obvious to one of ordinary skill in the art.

The materials used for each embodiment within each version are those commonly used for making artificial hip joints. The inventor has no preference.

So long as usable head rotation can be maintained without a certain feature within a combination of features, that feature is optional. Of course, parts of different versions may be combined when they produce usable head rotation. Again, all embodiments mentioned above are merely intended to be examples, and are not intended to limit the scope of the invention—one of ordinary skill in the art will know many variations on implementing the details without varying the inventive concepts.

BRIEF DESCRIPTION OF THE DRAWINGS

The accompanying drawings, which are incorporated in and form a part of the specification, illustrate preferred (but not necessarily necessary) embodiments of the present invention and, together with the description and summary, disclose principles of the invention. Note: not all features of an embodiment and/or version are necessarily present in one drawing.

FIG. 8C is a perspective view of a second method of the cup-cable being assembled into an embodiment of the cup.

FIG. 13B is a perspective partial cross section view of an embodiment with the head-cable attaching to the head at each end of the head-cable.

FIG. 23A is a perspective, partial cross section view of an embodiment with an outside track with knob, also with horizontal swivel.

FIG. 24A is a perspective view of an embodiment of two perpendicular inside tracks with knobs on opposite sides of the head and a swivel in between.

DETAILED DESCRIPTION

Versions of the invention allow for increased degrees of rotation of a head-bone along three independent axes relative to the cup-bone, while still constraining the head-bone from dislocation from the cup-bone.

Figure 12A:
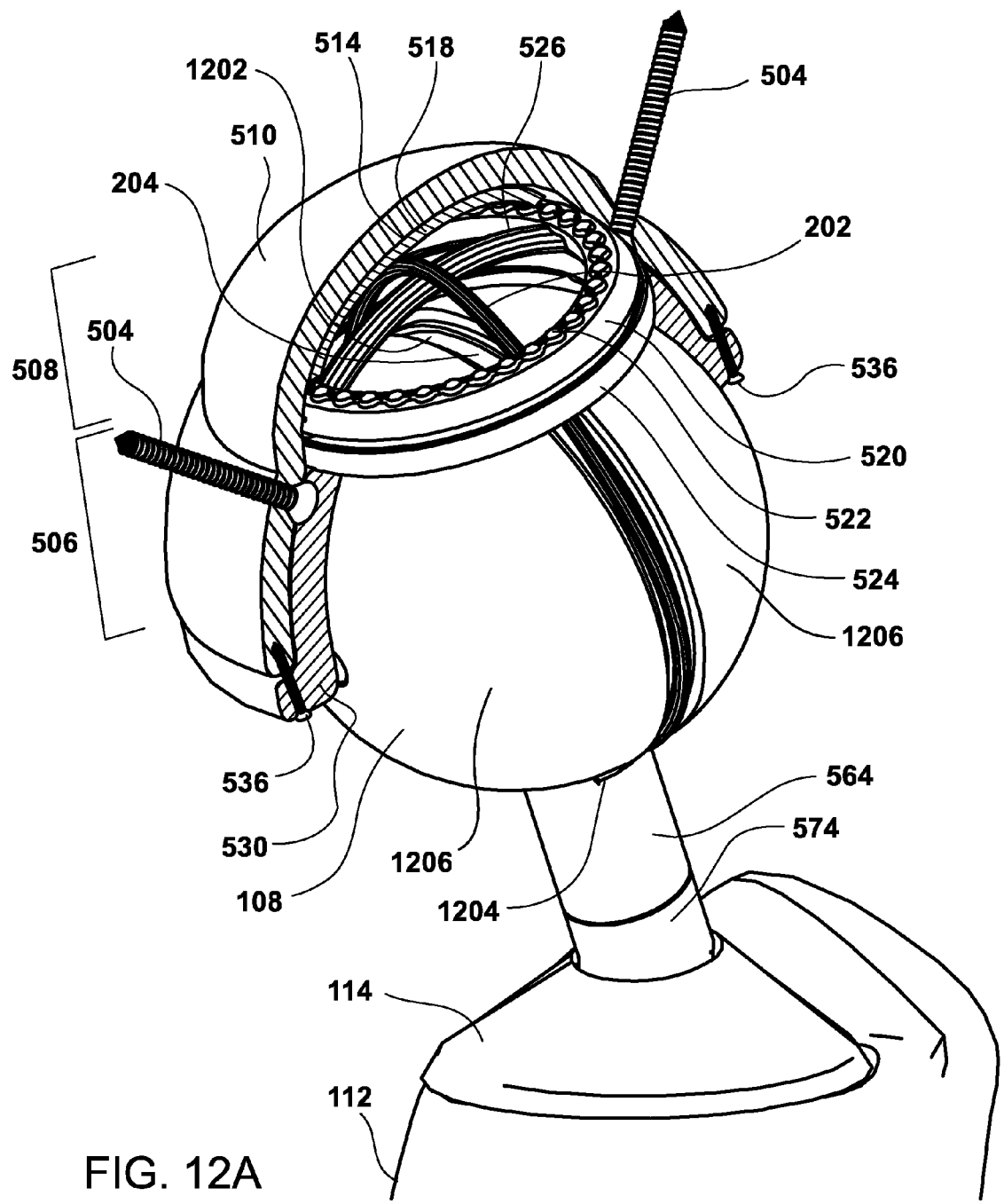
FIG. 12A is a perspective, partial cross section view of the embodiment of FIG. 5.
Figure 12B:
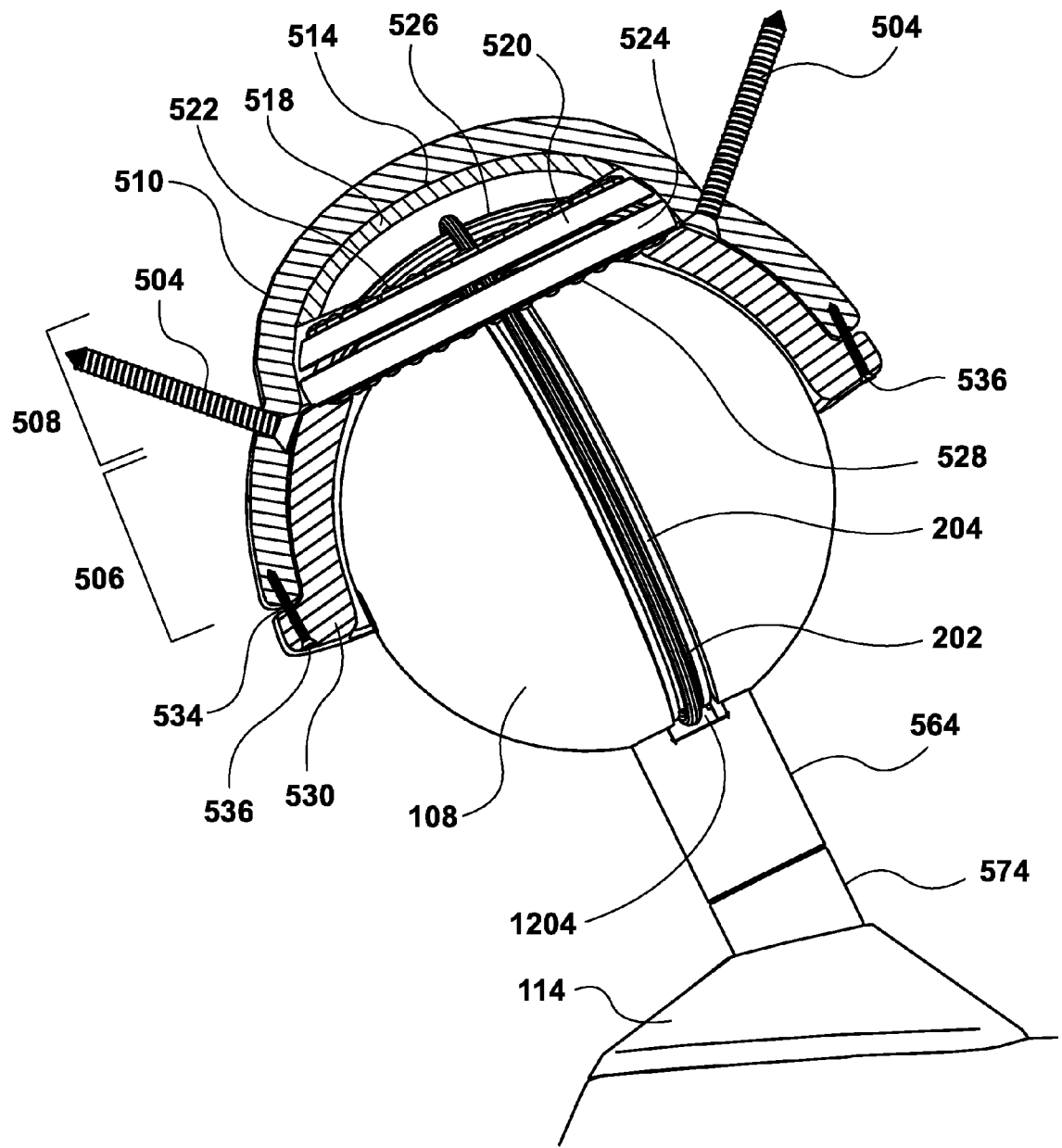
FIG. 12B is a side view, partial cross section of the embodiment of FIG. 5.

First, to explain some terms—imagine the head as an earth viewed from space, with an equator, a north pole, south pole, northern hemisphere, latitudinal lines (running sideways), longitudinal lines (running north and south). Now imagine a head from the preferred embodiment from the first version 108 inside a socket 104 of a cup 106 (see FIG. 12). The head's north pole 1202 is closest to the apex of the inner surface of the cup 702 (though when the head 108 rotates, the head's north pole 1202 rotates). The apex of the inner surface of the cup may also be referred to as "the north pole of the inner surface of the cup." The head's south pole 1204 is furthest from the apex 702 of the inner surface of the cup 802. The head's equator 1206 contacts where the rim of the inner surface of the cup 532 meets the head 108 through the cup-liner 531 (except when the head 108 rotates). In neutral position (when the head 108 has not articulated in any directions yet), the cup's north pole 514 and equator 532 are at approximately the same point as the head's north pole 1202 and equator 1206 (this is not true when the head 108 has rotated along either the line of a cup-cable 526 or perpendicularly along the line of a head-cable 202). Usable head rotation means geometries of various parts that when combined into an embodiment and/or version, allow for head rotation that satisfies a particular function (walking default, alternatively normal movement, or movement sufficient to do a particular activity and/or other functions), and obviously does not break down after a week of use (alternatively, nor does it lead to excess buildup of toxic material, for example metal debris leaching out into the body resulting from metal on metal rubbing). For instance, the term "horizontal" (usually used in context of a "horizontal swivel") means latitudinal enough for usable head rotation (the term horizontal is defined alternately and more specifically below).

Cables Version

Versions of the invention allow for increased degrees of rotation of a head-bone along three independent axes relative to the cup-bone, while still constraining the head-bone from dislocation from the cup-bone.

Cables Version:

FIGS. 1-12 all depict an embodiment (which is the preferred embodiment) of the first version. This version comprises (see FIG. 5, and also FIG. 2 for most parts) A) a head to head-bone rod 218 (with one end to be inserted into the head-bone such as a femur 112 or a humerus 402, and a second end connected to a head 108), B) the head 108 and C) a cup 106 encircling the head 108, with the cup 106 to be inserted into the cup-bone (such as the hip-bone 102 or the shoulder framework 404), and D) a cup-liner 531 interposed between the cup 106 and the head 108.

A. The head to head-bone rod 218 is comprised of i) a stem 110, the stem 110 at one end connecting to a head 108, and at a second end connecting to ii) a head-bone rod 114, said head-bone rod 114 to be inserted into the head-bone (such as a femur 112 or a humerus 402). i) The stem 110 is comprised of a) a pronged portion of the stem 564, said pronged portion of the stem comprising a hole at the non-pronged end 576 for insertion of a pronged-non-pronged threaded portion of the non-pronged portion of the stem 572, two parallel prongs 571 with a hole between the prongs 570, and two holes for two countersunk screws 568 (to go through the head 108), and b) a non-pronged portion 574, comprised of a pronged-non-pronged threaded section 572, and a head-bone connecting threaded section 574 with threads 575, said head-bone connecting threaded section 574 having a hole 578 for insertion of a head-bone connecting screw 214 connecting said section 574 to the head-bone rod 114 and the head-bone (such as a femur 112 or a humerus 402). ii) The head-bone rod 114 is comprised of a male portion to be inserted into the middle of the head-bone (such as a femur 112 or a humerus 402), a lip, a hole in the lip 212 for said head bone connecting screw 214 (connecting threaded section of head-bone connecting threaded section of stem 574 to the head-bone rod 114 and the head-bone (such as a femur 112 or a humerus 404)), and a female portion 216 for insertion of the threaded portion 575 of the non-pronged portion 574 of the stem 110.

B. The head 108 is comprised of i) a left semi-hemisphere 542 connected to ii) a central portion 556 with a groove, ball bearings around the groove 602, a sheath around the ball-bearings 204, and a head-cable around the sheath 202, said central portion 556 connected to iii) a right semi-hemisphere 544. i) The left semi-hemisphere 542 contains a slot 546 for the first countersunk screw 538 connecting the two semi-hemispheres, a slot 547 for the second screw 540 connecting the two semi-hemispheres, and slot 554 for one of the prongs of the stem 571. ii) The central portion 556 has two slots 558 for the countersunk screws. iii) The right semi-hemisphere 544 has a first slot 548 and a second slot 550 for the counter- sunk screws, and a slot 547 for one of the prongs of the stem 571. The head 108 has a north pole 1202, a south pole 1204, and an equator 1206.

C. The cup 106 comprises i) an outer shell 502 ii) a middle shell 517 and iii) an inner shell 530.

i. The outer shell 502 comprises a spherical portion 506 closest to the outer shell's equator 516 and moving up to a certain latitude on the head 108 where the outer shell is hollowed out beyond spherically (where the radius is larger), called the super-spherical portion of the outer shell 508. The outer shell helps enclose the super-spherical cavity 804. Note the north pole of the inner surface of the outer shell 514. Note that the outer shell 510 juts inward at the lower ends so that the inner surface of the cup 802 is perpendicular to the cup-cable 526 when meeting the cup-cable's 526 ends (this can help prevent the head-cable 202 from getting caught between the cup-cable and the inner surface of the cup 802). The outer shell is connected to the head-bone, such as the hip bone 102 or the shoulder framework 404 by two screws 504. The outer shell is connected to the inner shell by two screws 536 that fit into two slots in the outer shell 906.

ii. The middle shell 517 comprises a) a mid-super-spherical inner shell 518 that fits inside the inner surface of the outer shell and shaped 902 to fit the ball-bearings 522 between it and a middle ring like portion 520 (with a north pole on its inside surface 702); b) a mid-middle ring like portion 520 shaped to fit the ball bearings 522 between it and the mid-super-spherical shell 518, with notches on the bottom 604 to trap a cup-cable 526 between the mid-middle ring like portion 520 and a mid-lower shell 524; c) a mid-lower shell 524 comprises a ring like portion with notches on top to fit the cup-cable 526 between it and the mid-middle ring like portion 520.

iii. The inner shell 530 has spherical portions 506 but a hole cut out from the top to fit the mid-super-spherical inner shell 518. The inner shell 530 encircles the cup-liner 531, and both have a lip 534 so that the outer shell 502 can rest upon the inner shell 530. The outer shell is connected to the inner shell by two screws 536 that fit into two slots in the inner shell 904.

Note that the inner surface of the cup 802 has both a spherical portion 506 and a super-spherical portion 508.

D. The cup-liner 531 is interposed between the cup 106 and the head 108, but does not block the super-spherical cavity 804.

Note: The above constitutes one embodiment of the first version of the invention—one particular way to build it—but that particular expression does not encompass all of the inventive concepts used in this version. Many other ways of making and using this version using the same concepts as used in this version will be obvious to one of average skill in the art. The main concepts are as follows:

More on usable head rotation: For instance, the term "horizontal" (usually used in context of a "horizontal swivel") means latitudinal enough for usable head rotation. For example, Osteoarthritis.com gives the following values for normal hip rotation (minimal and maximal): flexion (bending) 0-125; extension (straightening) 115-0; hyperextension (straightening beyond normal range) 0-15; abduction (move away from central axis of body) 0-45; adduction (move towards central axis of body) 45-0; lateral rotation (rotation away from center of body) 0-45; medial rotation (rotation towards center of body) 0-45. Ten to thirty degree flexion is necessary for walking (Spina Bifida Association of America, sbaa.org), though lower degrees of flexion still enable movement of the joint. For shoulder joint rotation, Shoulder flexion 0-90; Shoulder extension 0-50; Shoulder abduction 0-90; Shoulder adduction 90-0; Shoulder lateral rotation 0-90;

Shoulder medial rotation 0-90. Thus, any embodiment within the inventive concepts detailed within this patent application that produces usable head rotation is therefore usable. Note that for the cables version, rotation along the cup-cable and independently along the head-cable is restricted to 180 degrees, unless the cup is recessed (see below).

Note that "usable head rotation" means for repeated use throughout the normal lifetime of an artificial hip joint, which is not accomplished if for example the head-cable 202 slips out of the groove 204 and doesn't allow for usable head rotation after a week (for instance) of use.

A. The head to head-bone rod fastens at one end to "roughly the south pole of the head" (or more exactly), and at the other end comprises a rod to be inserted into the head-bone. (See for example FIG. 2). ["Roughly the south pole of the head" means close enough to the south pole of the head to allow for usable head rotation.] If the head-cable 202 passes through "about the head's south pole", ["about the head's south pole" means close enough to the south pole to allow for usable head rotation] then the head to head-bone rod 218 has a hole roughly at the south pole end to allow the head-groove and head-cable to pass through about the south pole. (See FIG. 9).

B. The head: The head 108 is "roughly a ball shape" [meaning having spherical portions of the surface of the head 108 that allow it to fit snugly within the spherical portions 506 of the inner surface of the cup 802, even when the head 108 is rotated along any axis allowed to any number of degrees allowed (in the context of all of the parts put together), as well as having room for the cup-cable 526 within the super-spherical cavity 804] that fits inside the cup 106 and contacts the spherical portions 506 of the inner surface of the cup 802 through the cup-liner 531. "A head fitting inside the inner surface of the cup" means the same thing as "roughly a ball shape". The phrase "contacting the spherical portion of the inner surface of the cup" contemplates direct contact with the spherical portion of the inner surface of the cup and/or indirectly through a cup-liner. Ideally, the head contacts all spherical portions of the inner surface of the cup, but alternatively, the head contacts enough spherical portions to allow for usable head rotation or more.

The head 108 has a "roughly longitudinal groove" [meaning sufficiently longitudinal to allow for usable rotational movement of the head 108 along the cup-cable 526 axis in both directions and defined as a "head-groove" 204] looped around the circumference of the head 108 running "roughly pole to pole" [meaning both 1) going from the north pole of the head 1202 to the south pole 1204 and back, and 2) changing direction in its loop from northward to southward (and vice versa), closely enough to each pole to allow for usable head 108 rotation, including but not limited to rotational movement of the head 108 along the cup-cable 526 axis in both directions]. Alternatively, the head-groove may be completely longitudinal and run completely pole to pole, or anything in between this exactitude and that allowing for usable head rotation. The phrase "fitting inside the head-groove when the head-cable is between the head and the spherical portion of the inner surface of the cup" means that those portions of the head-cable that are currently between the spherical portion of the inner surface of the cup and the head are inside the head-groove so as not to get caught or pinched between the head's spherical surface and the spherical portion of the inner surface of the cup. Alternatively, the head-cable can be "looping around a portion of the head", where the head cannot move translationally away from the inner surface of the cup's north pole without the head-cable tightening, or catching. This serves the same purpose of constraining the head translationally as when the head-cable is "attaching to the head" at at least two ends.

Figure 1:
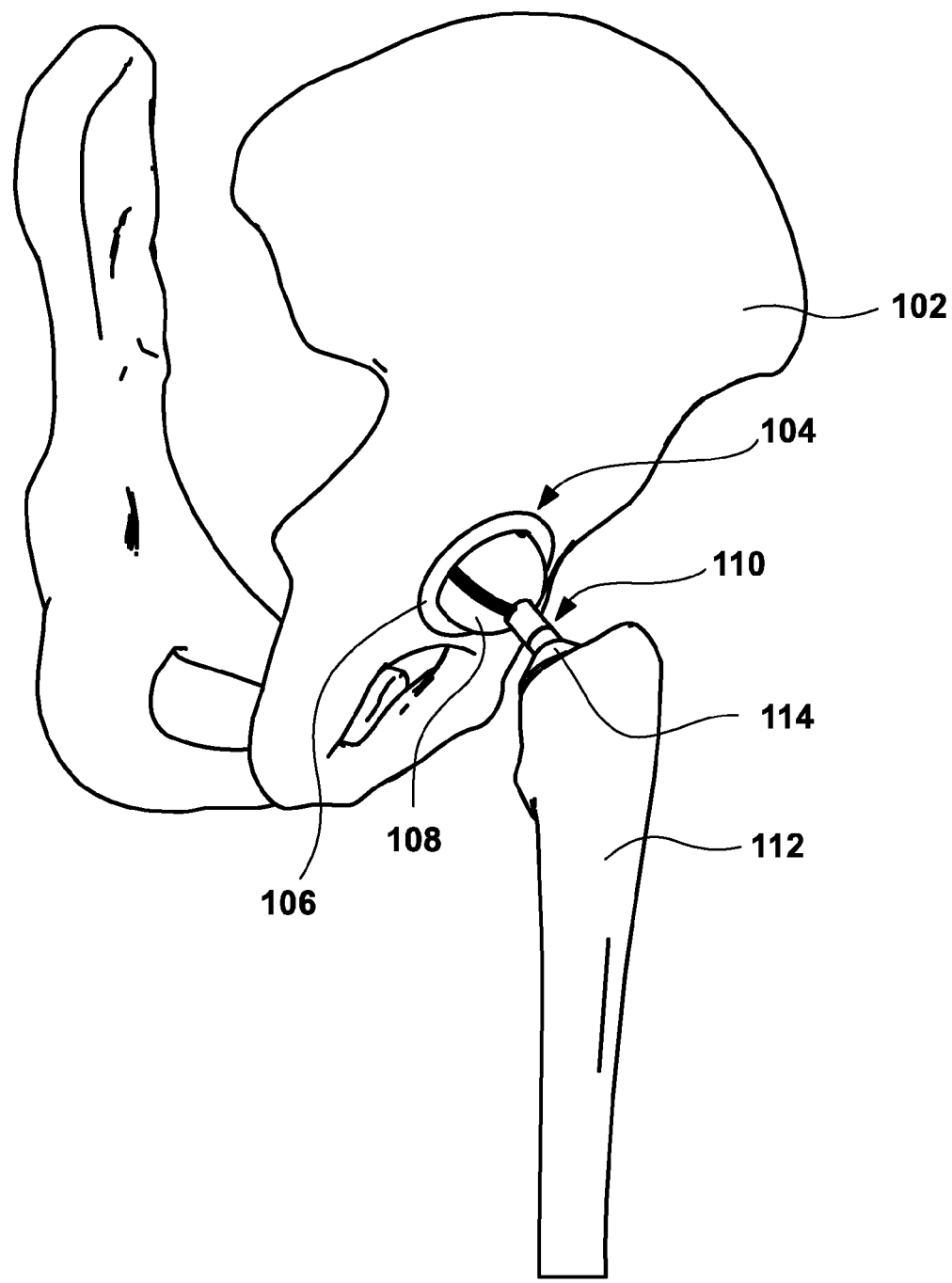
FIG. 1 is a perspective view of an embodiment of the invention connecting a femur to a hip bone.
Figure 2:
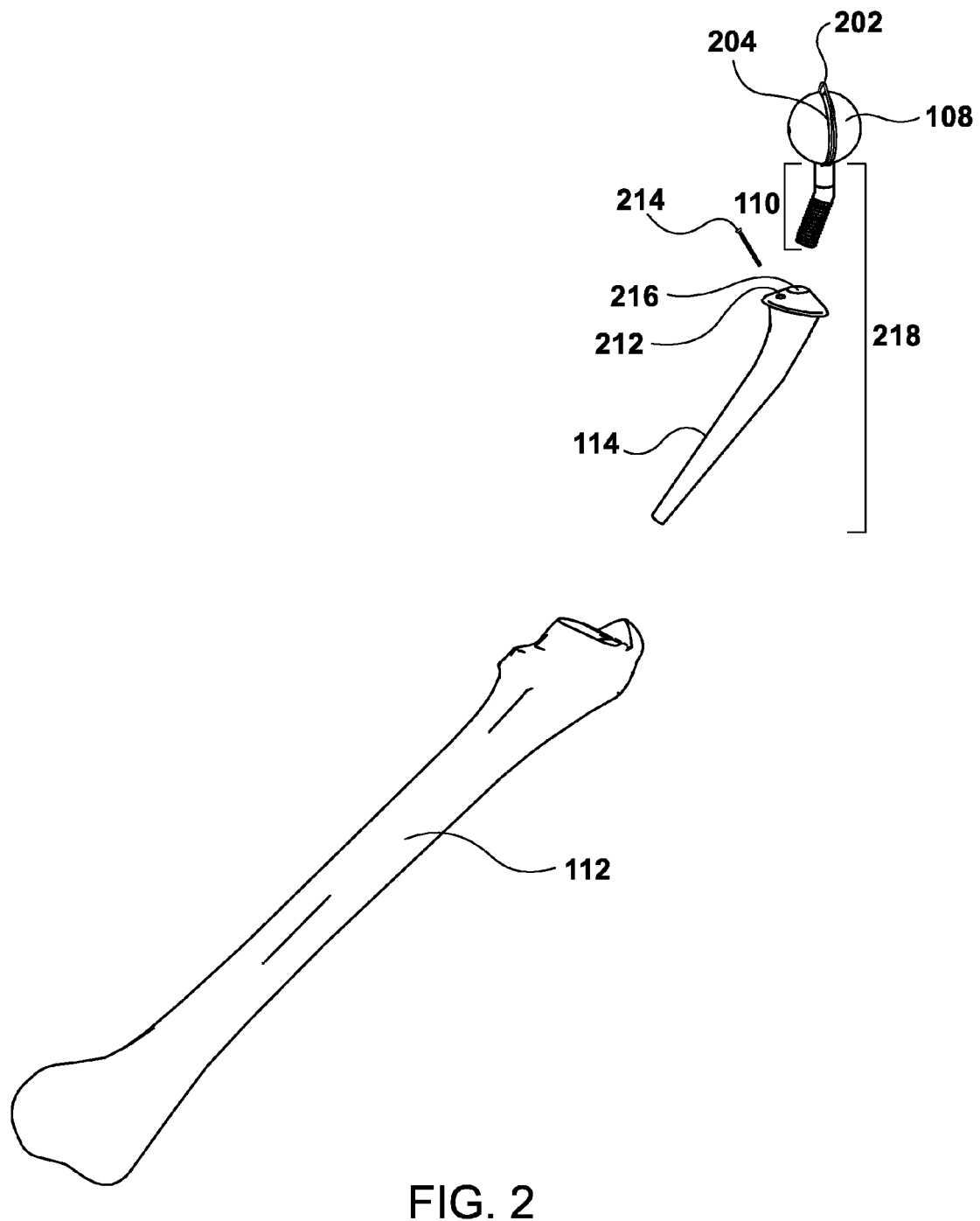
FIG. 2 is a partially exploded view of an embodiment of the invention with a head-cable.
Figure 3A:
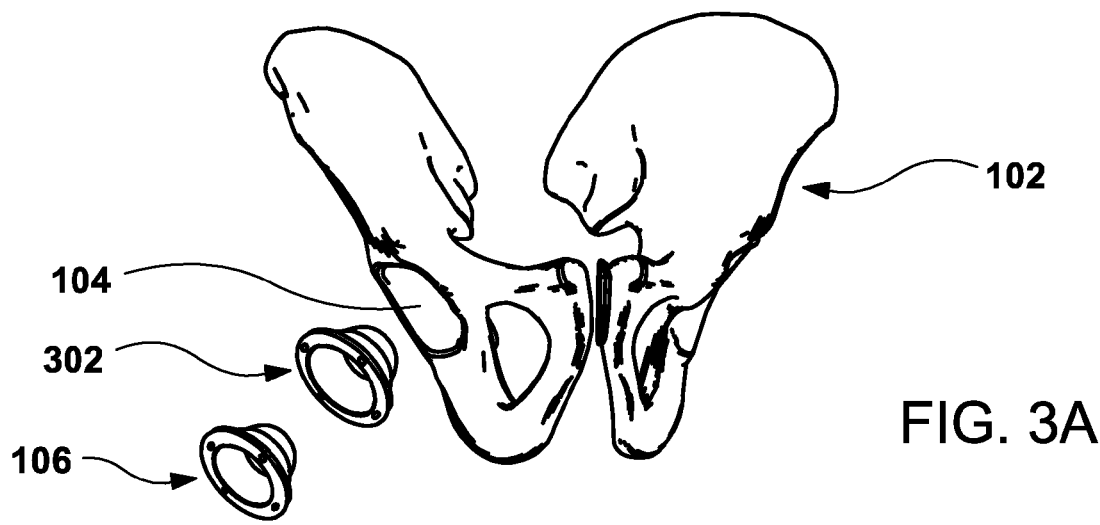
FIG. 3A is a perspective exploded view of a hip bone, an embodiment of cup liner and of cup.
Figure 3B:
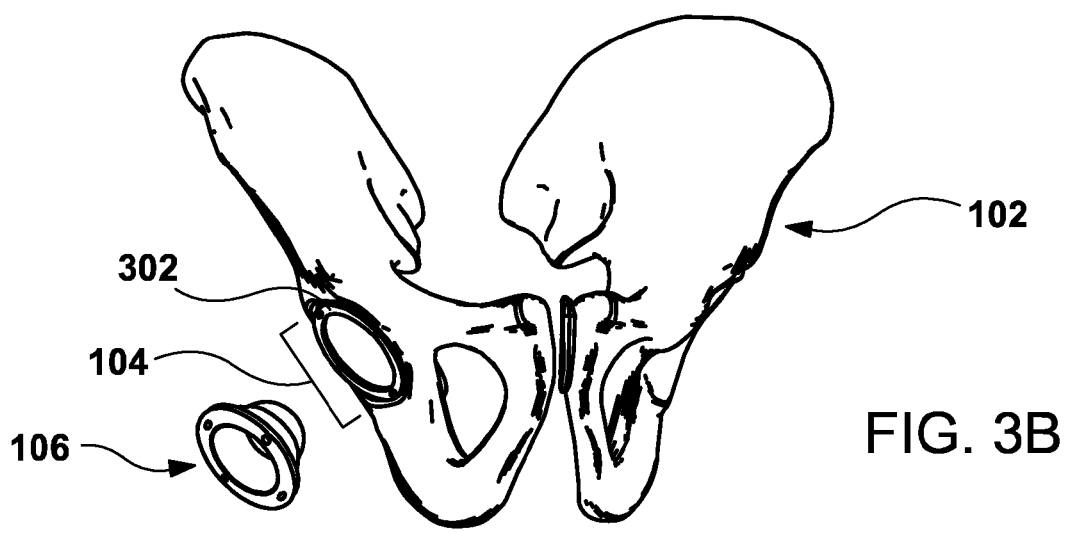
FIG. 3B is a perspective partially exploded view of the embodiment of FIG. 3A.
Figure 3C:
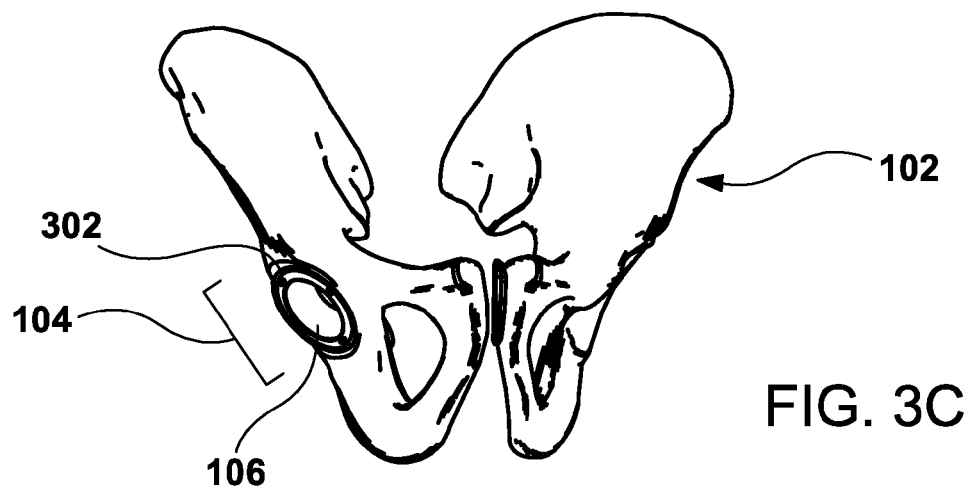
FIG. 3C is a unexploded perspective view of the embodiment of FIG. 3A.
Figure 4A:
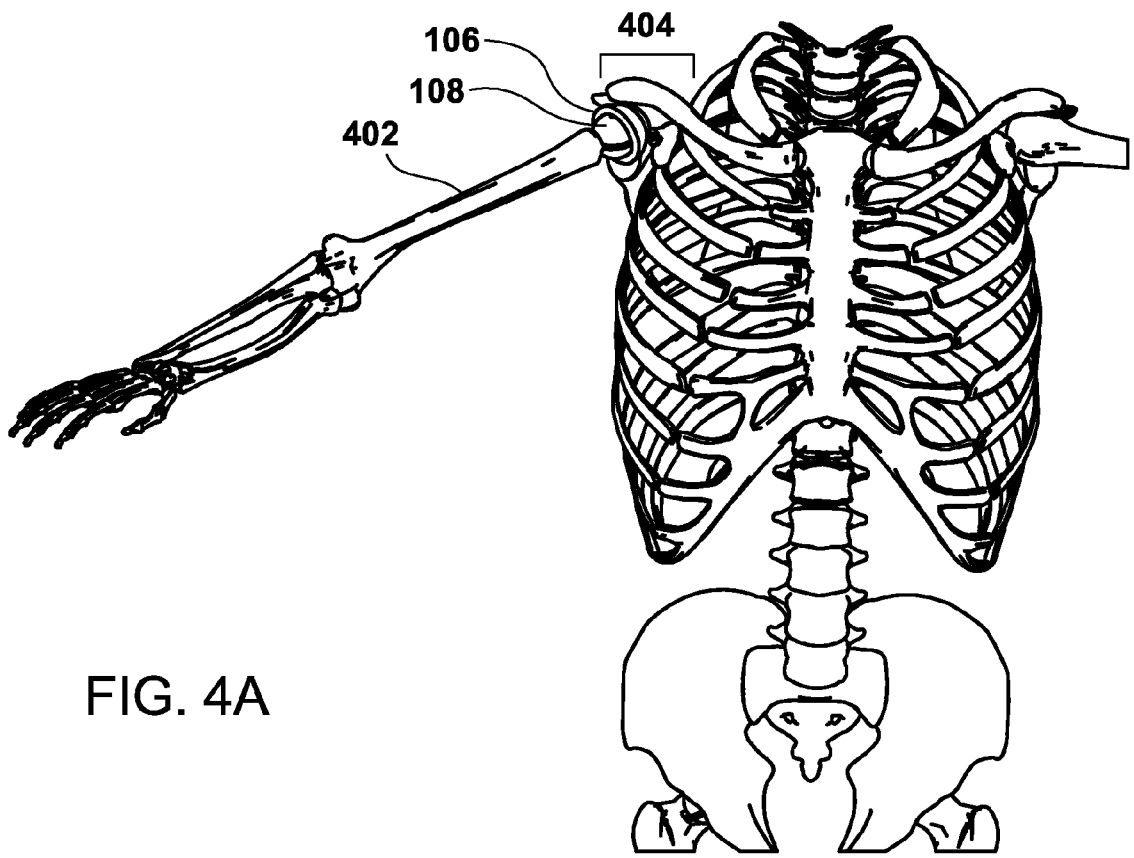
FIG. 4A is a perspective view of an embodiment of the invention forming the glenohumeral joint.
Figure 4B:
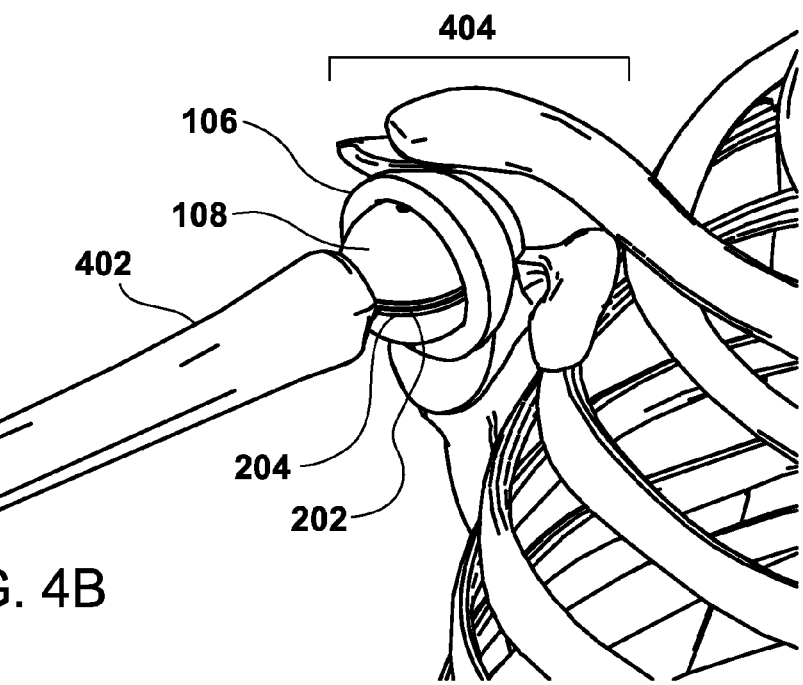
FIG. 4B is a perspective view of the embodiment of FIG. 4A, but with the glenohumeral joint magnified.
Figure 5:
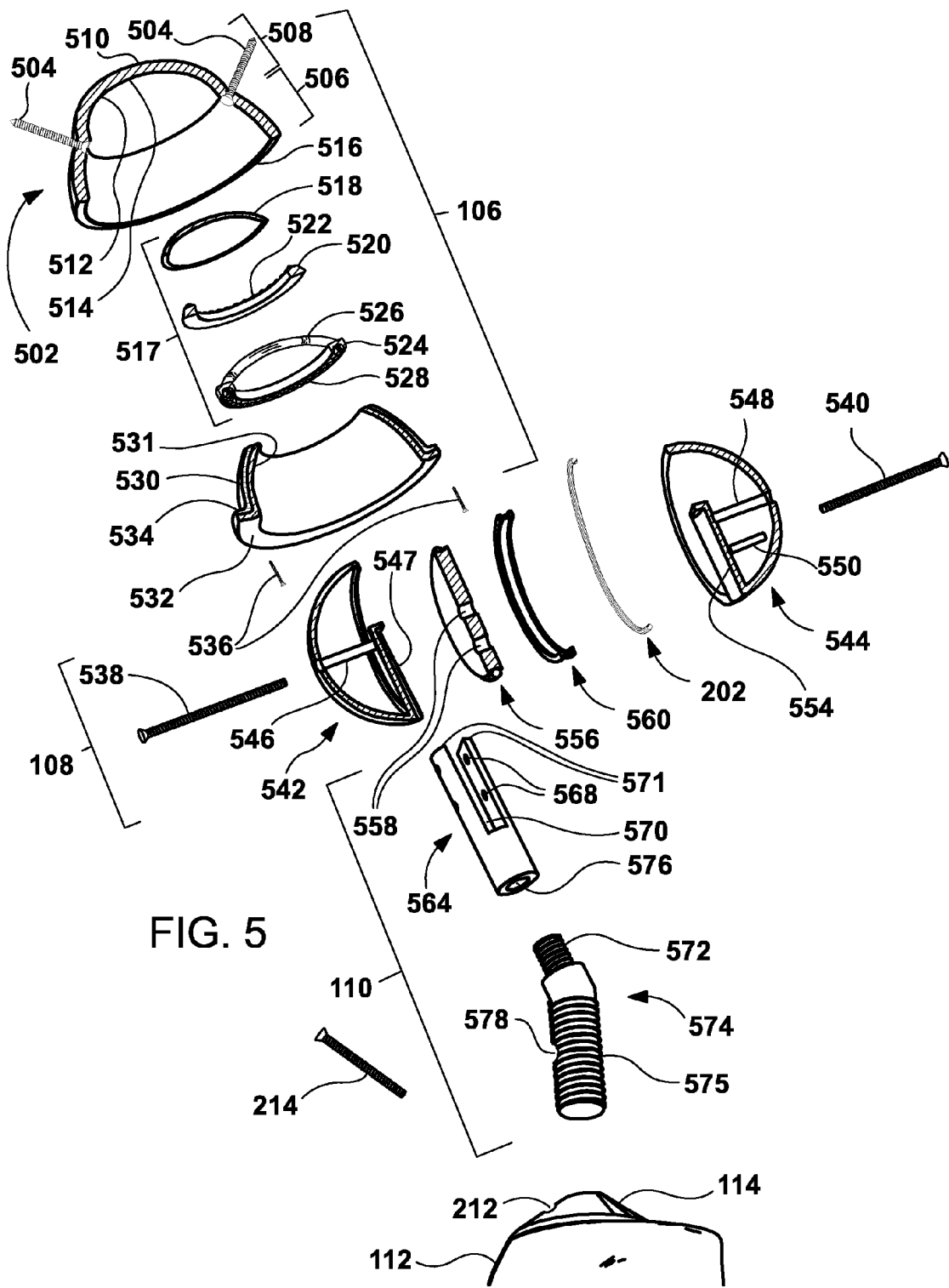
FIG. 5 is a perspective, exploded, partial cross section view of an embodiment with head-cable.
Figure 6:
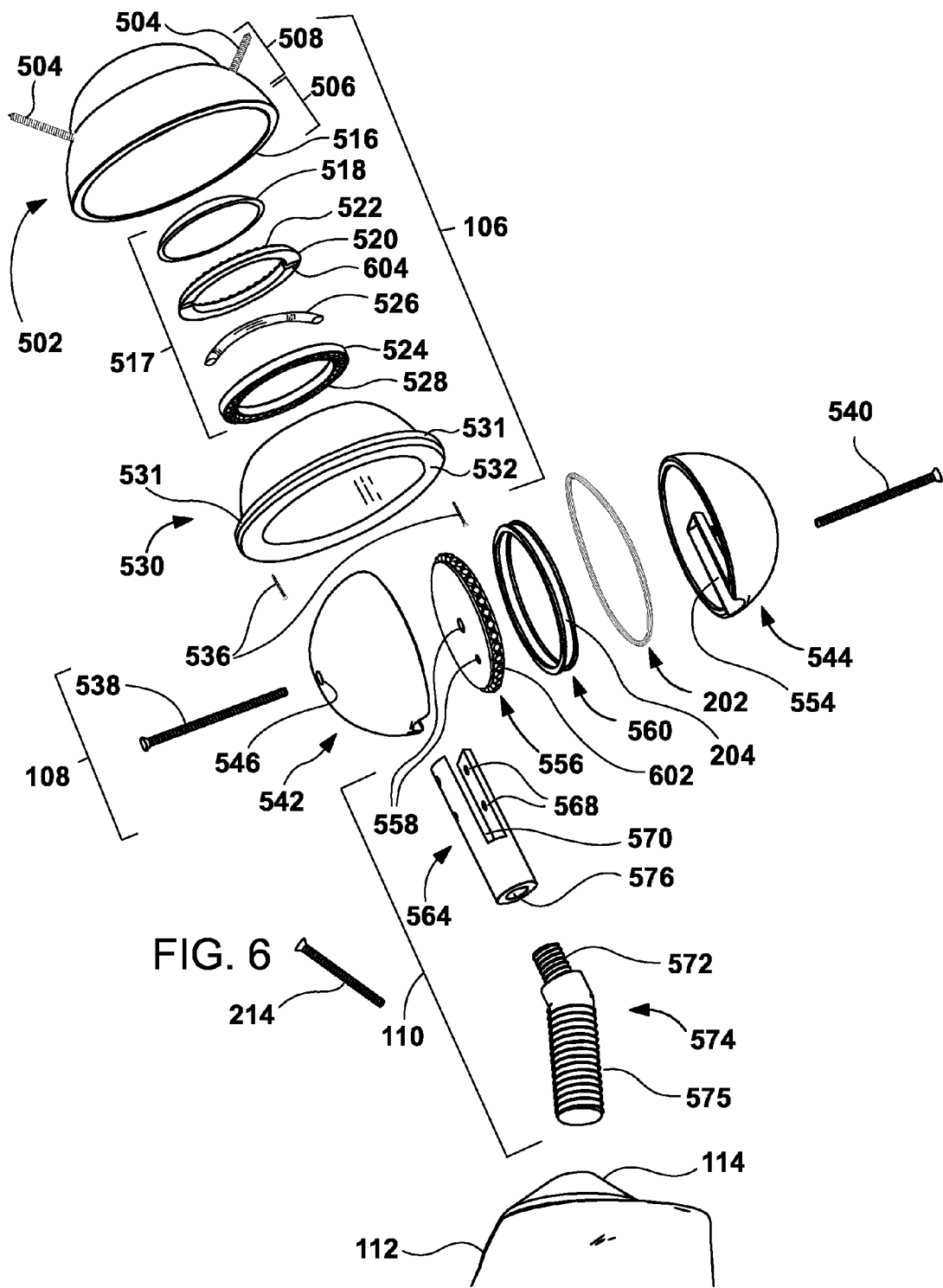
FIG. 6 is a perspective, exploded view of the embodiment of FIG. 5.
Figure 7:
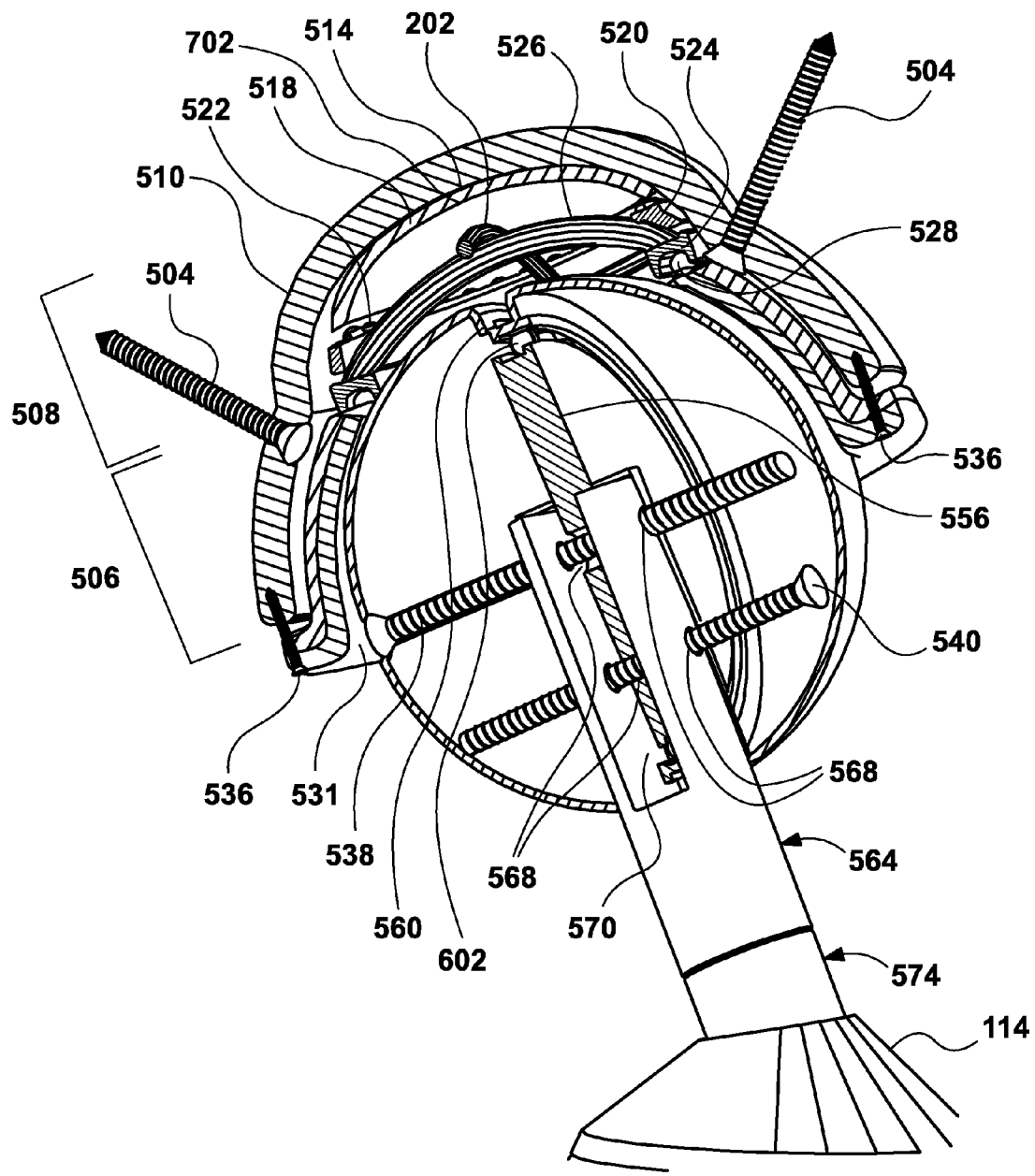
FIG. 7 is a perspective, partial cross section view of the embodiment of FIG. 5.
Figure 8A:
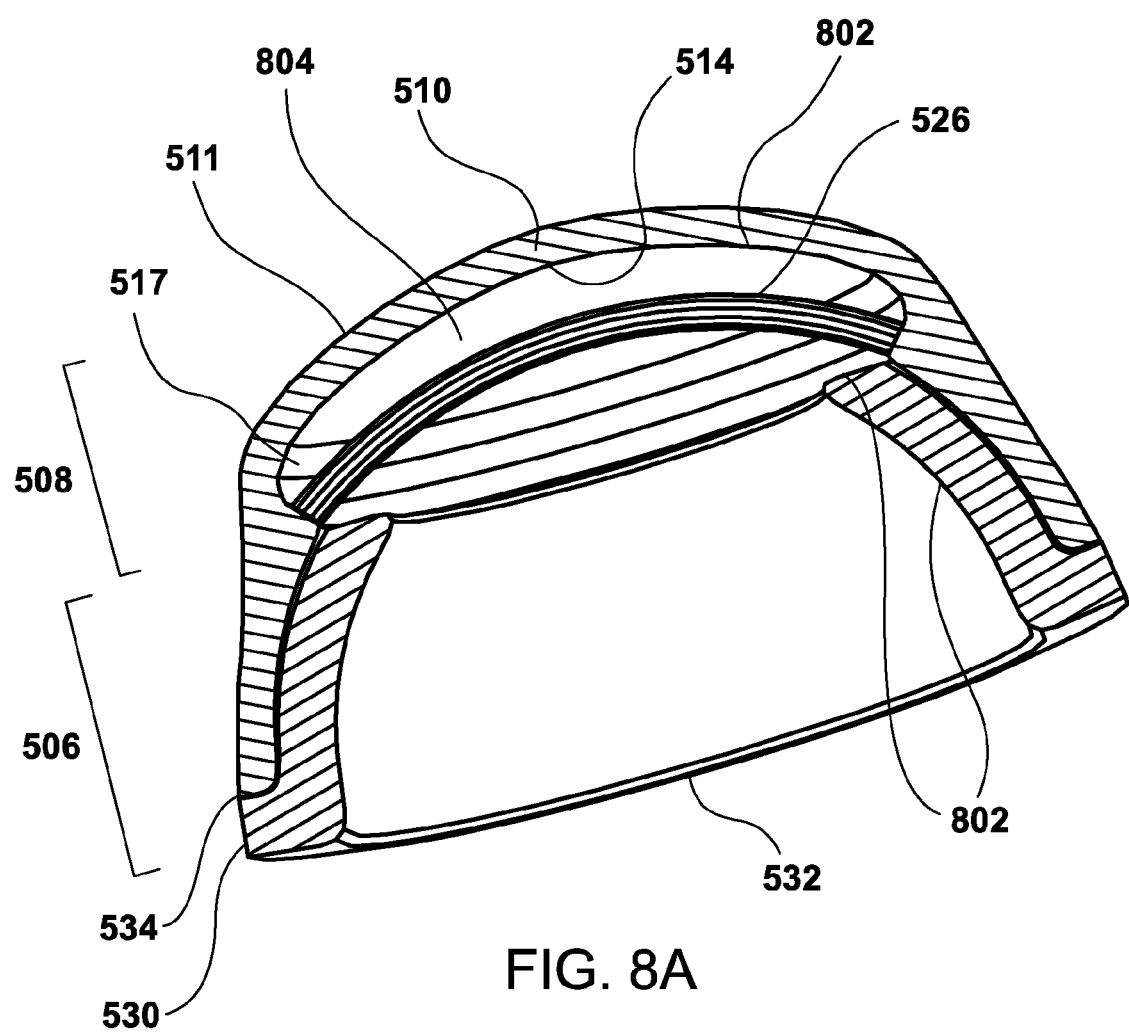
FIG. 8A is a cross section view of an embodiment of the cup.
Figure 8B:
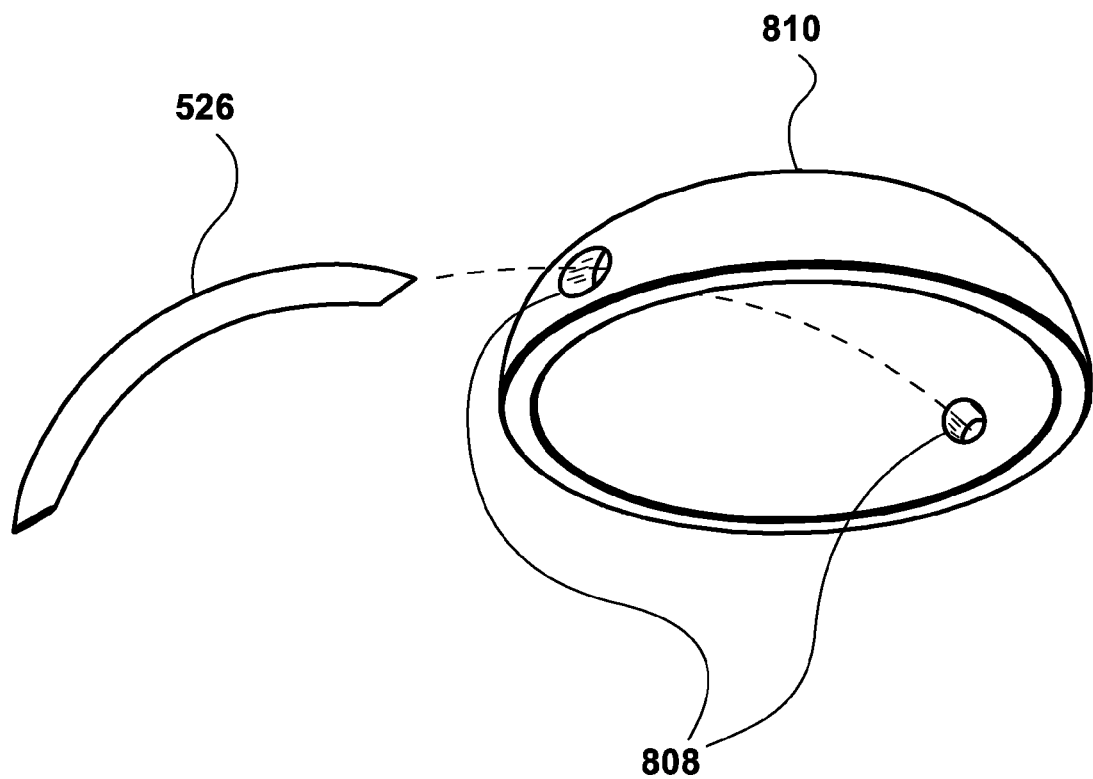
FIG. 8B is a perspective view of a first method of the cup-cable being assembled into an embodiment of the cup.
Figure 9:
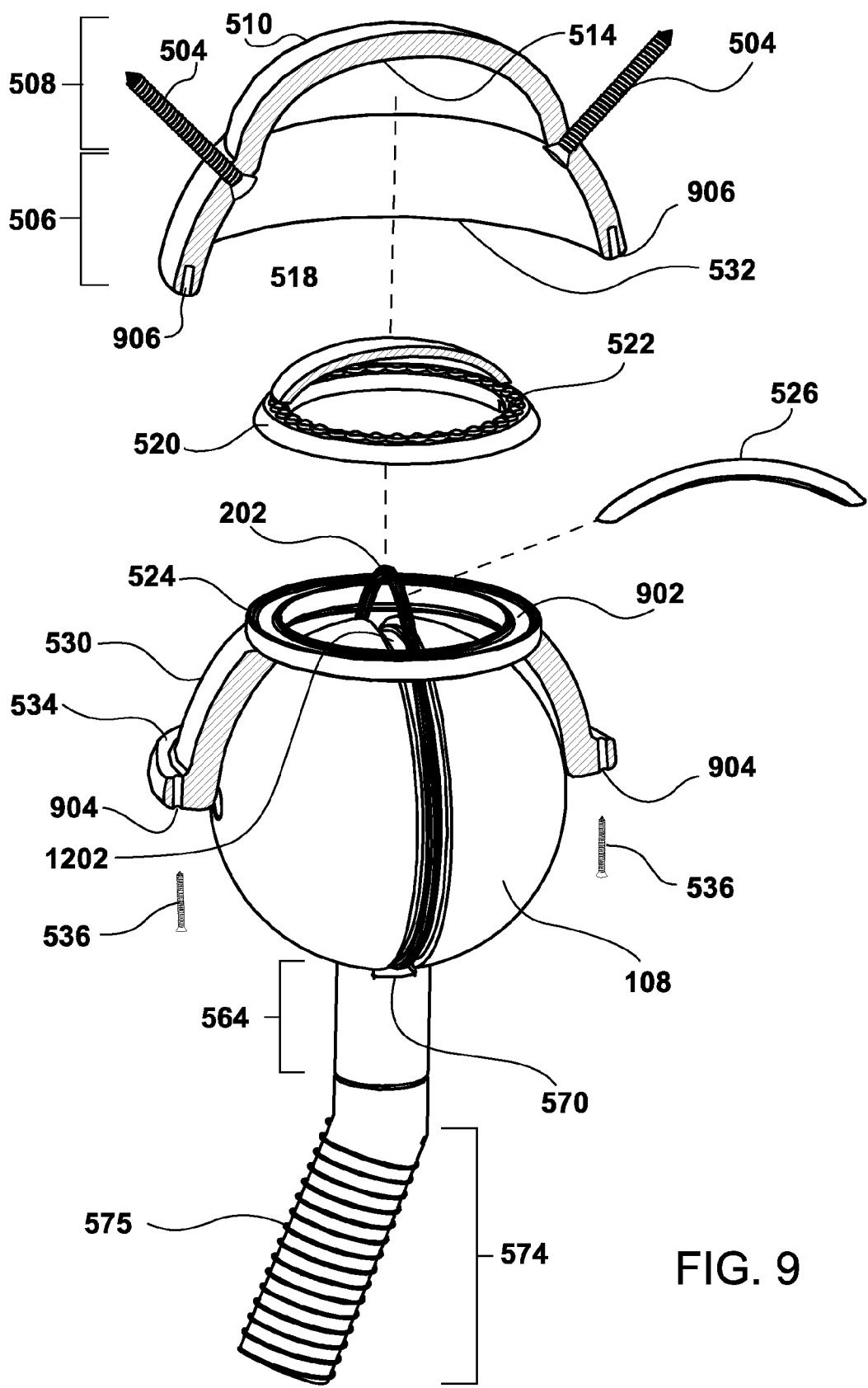
FIG. 9 is a perspective partial cross section view of the embodiment of FIG. 5.
Figure 10:
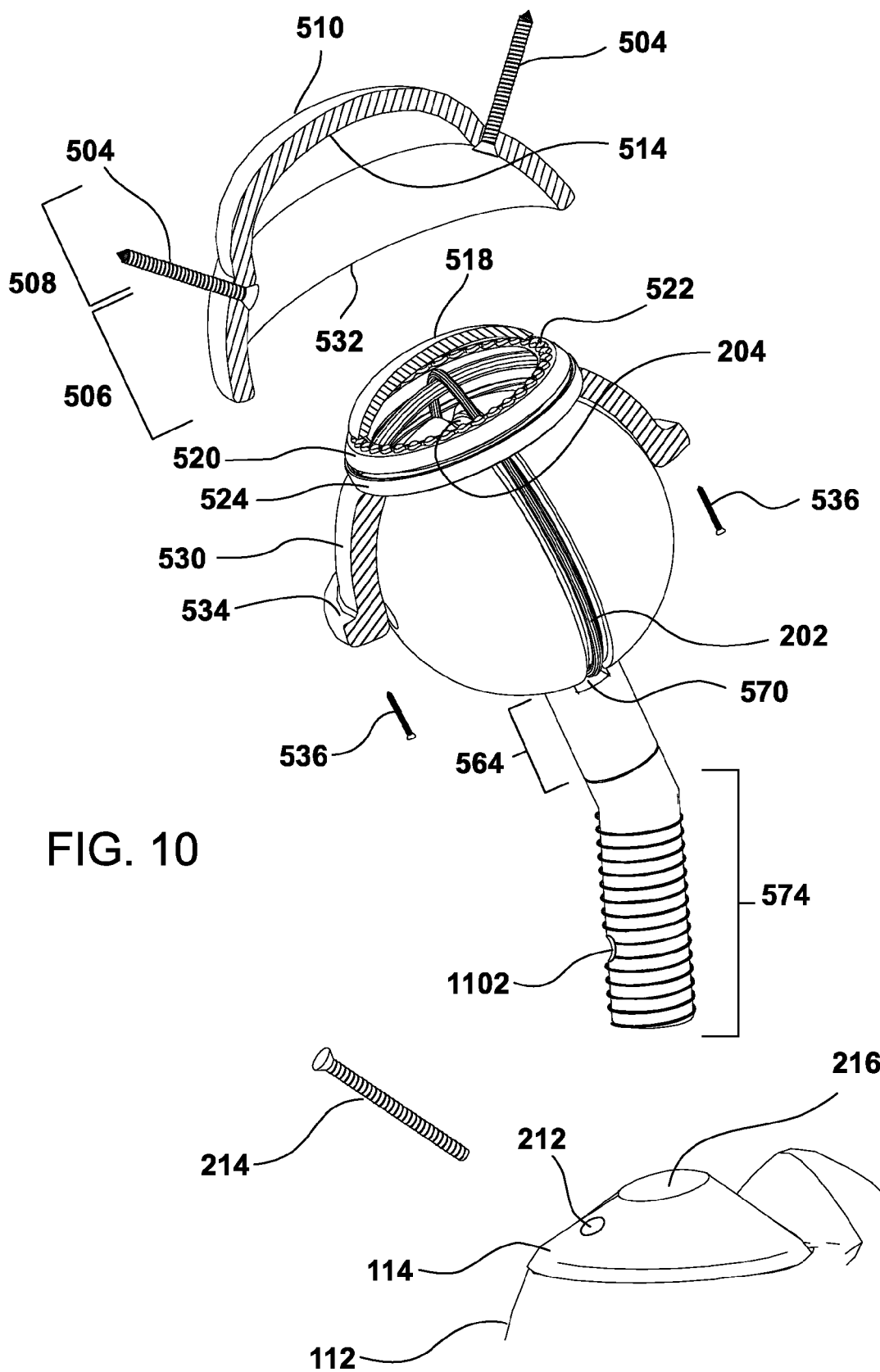
FIG. 10 is a partially exploded, partial cross section view of the embodiment of FIG. 5.
Figure 11A:
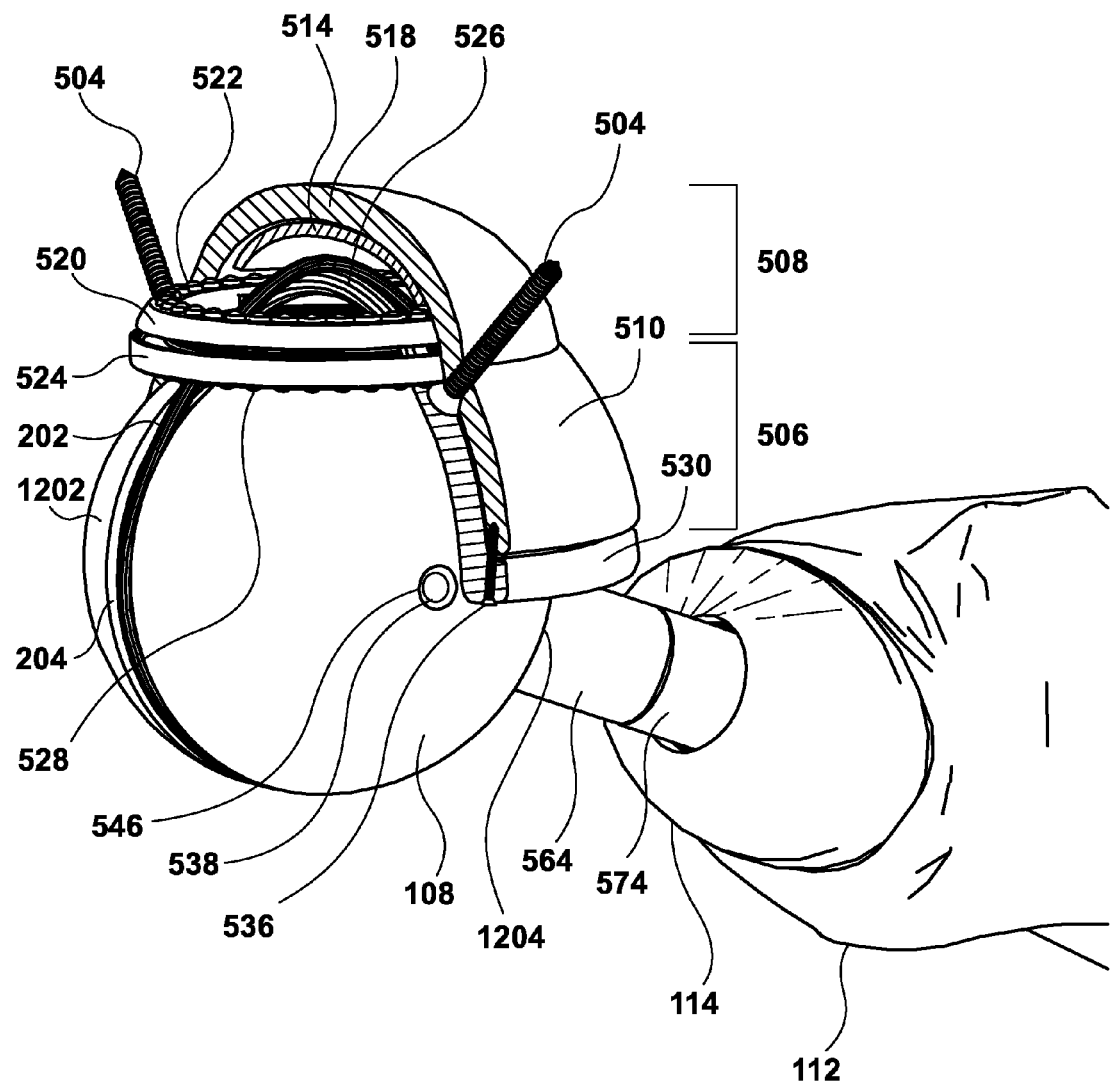
FIG. 11A is a perspective, partial cross section view of the embodiment of FIG. 5 with the head rotated along the line of the head-cable.
Figure 11B:
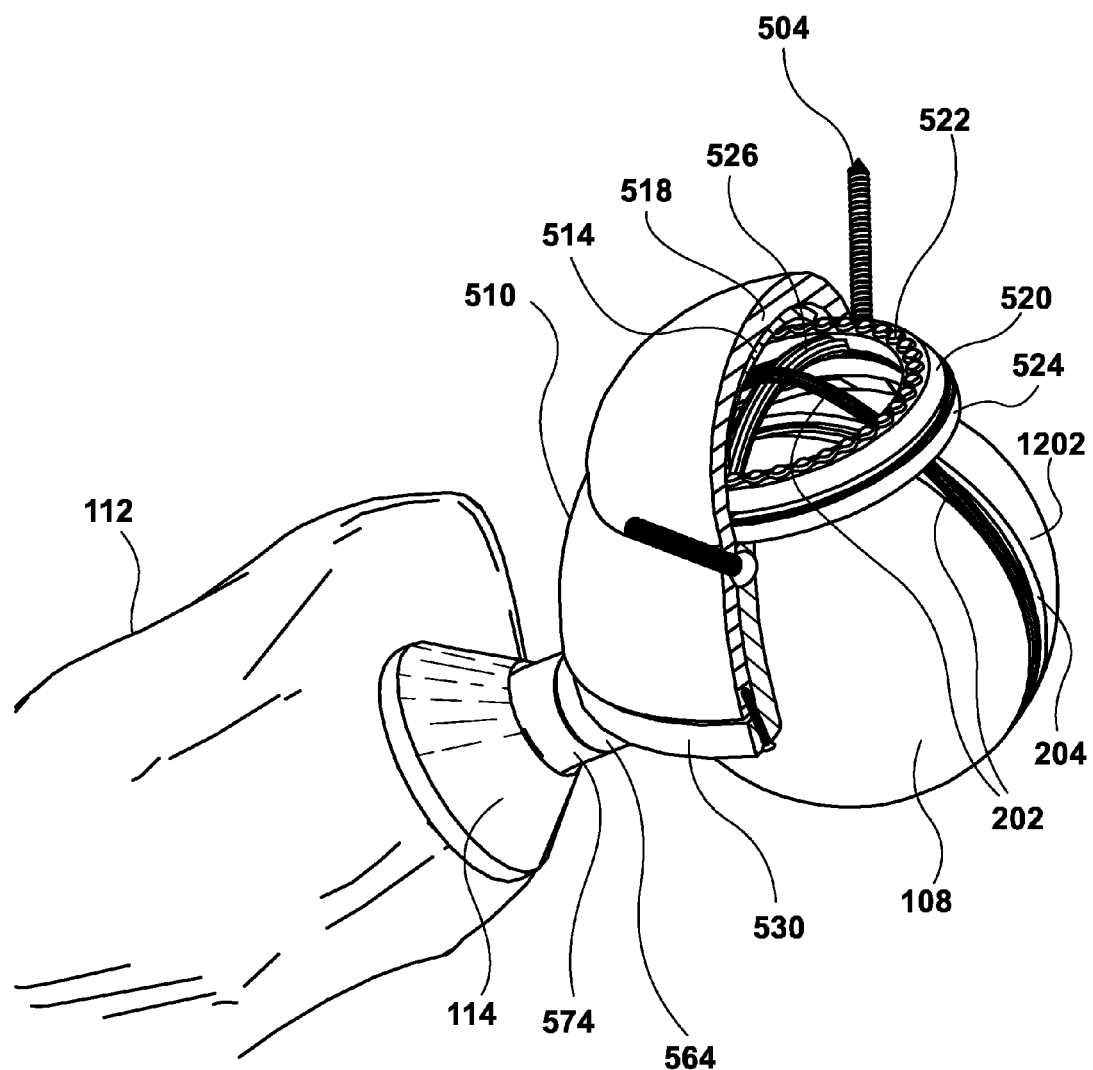
FIG. 11B is a different perspective view of the embodiment of FIG. 5 with the head rotated along the line of the head-cable.
Figure 11C:
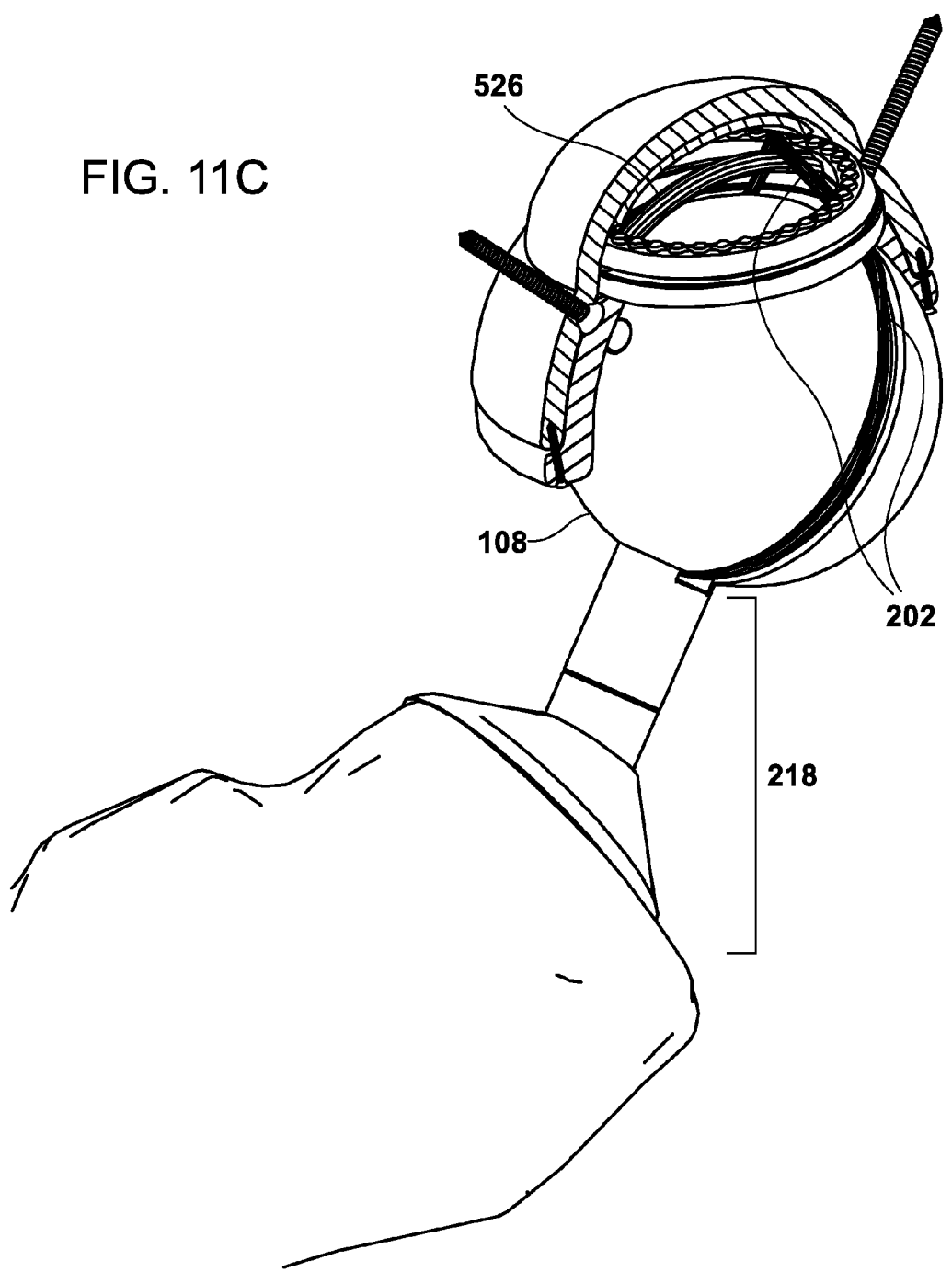
FIG. 11C is a perspective, partial cross section view of the embodiment of FIG. 5 with the head rotated along the line of the head-cable and rotated along the line of the cup-cable.
Figure 11D:
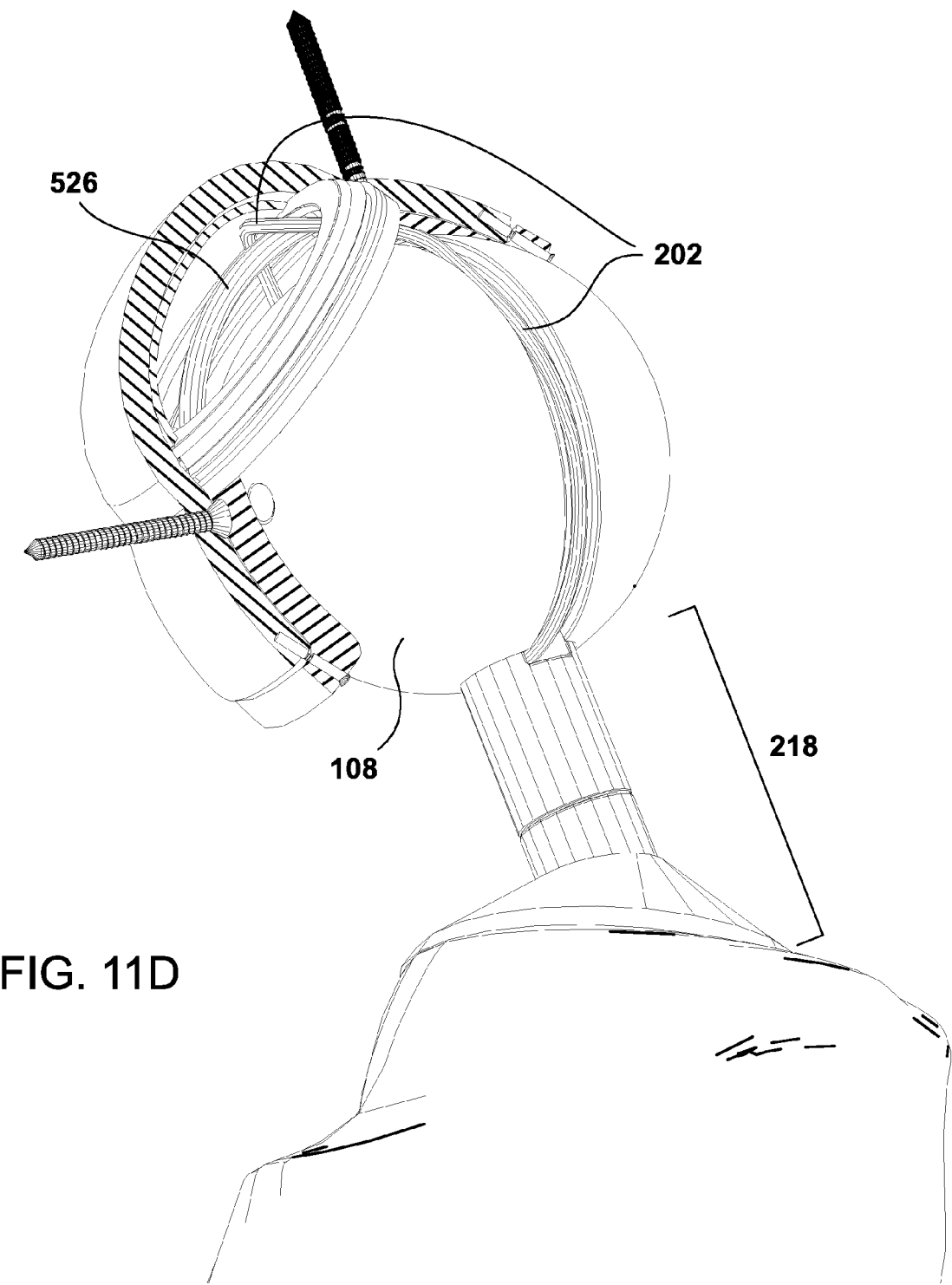
FIG. 11D is a different perspective, partial cross section of the embodiment of FIG. 5 with the head rotated along the line of the head-cable and rotated along the line of the cup-cable.
Figure 16A:
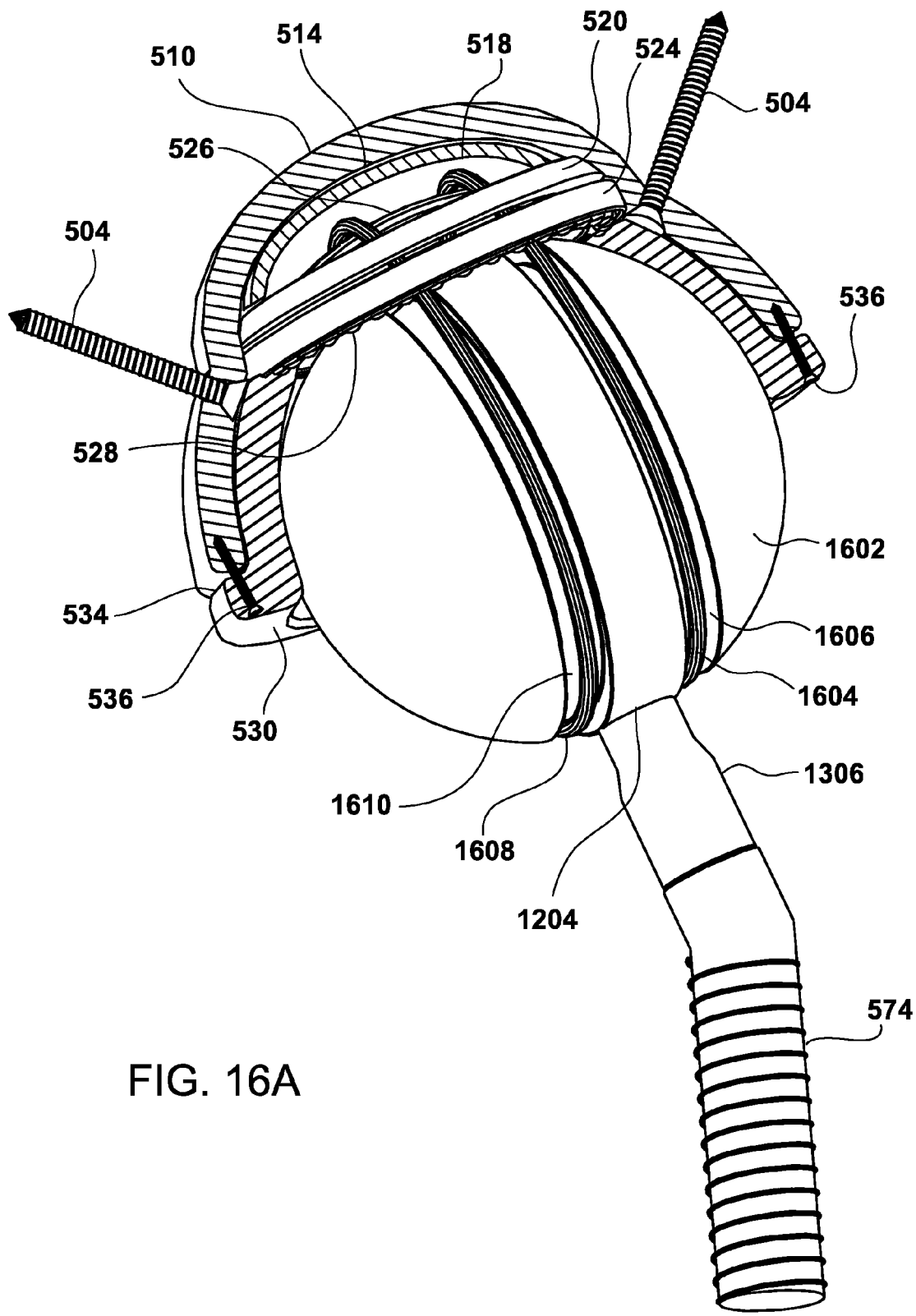
FIG. 16A is a perspective, partial cross section view of an embodiment with two head-cables.

Note that while ball-bearings are included in the preferred embodiment between the head 108 and the head-cable 202, allowing the head 108 to rotate independently of the head-cable 202, thus allowing the head-cable 202 to maintain its shape when it loops around the cup-cable 526, thus obviating the need for the head-cable 108 to be flexible 202, if the head-cable 108 is flexible, then it can change its shape as the stretch of head-cable forming the loop around the cup-cable 526 changes. (This change in shape can also allow the head 108 to potentially rotate further than if the head-cable was straight—see for example FIG. 11D showing the head-cable line rotating further along the head 108 than in the super-spherical cavity 804—see also FIG. 16D.) Additionally, even if the head-cable 202 was not flexible, and the head 108 did not rotate independently from the head-cable 202, there would still be wiggle room before either an end of the loop of the head-cable 108 hit the cup 106 or the head-cable 108 caught on the cup-cable 526.

Figure 13A:
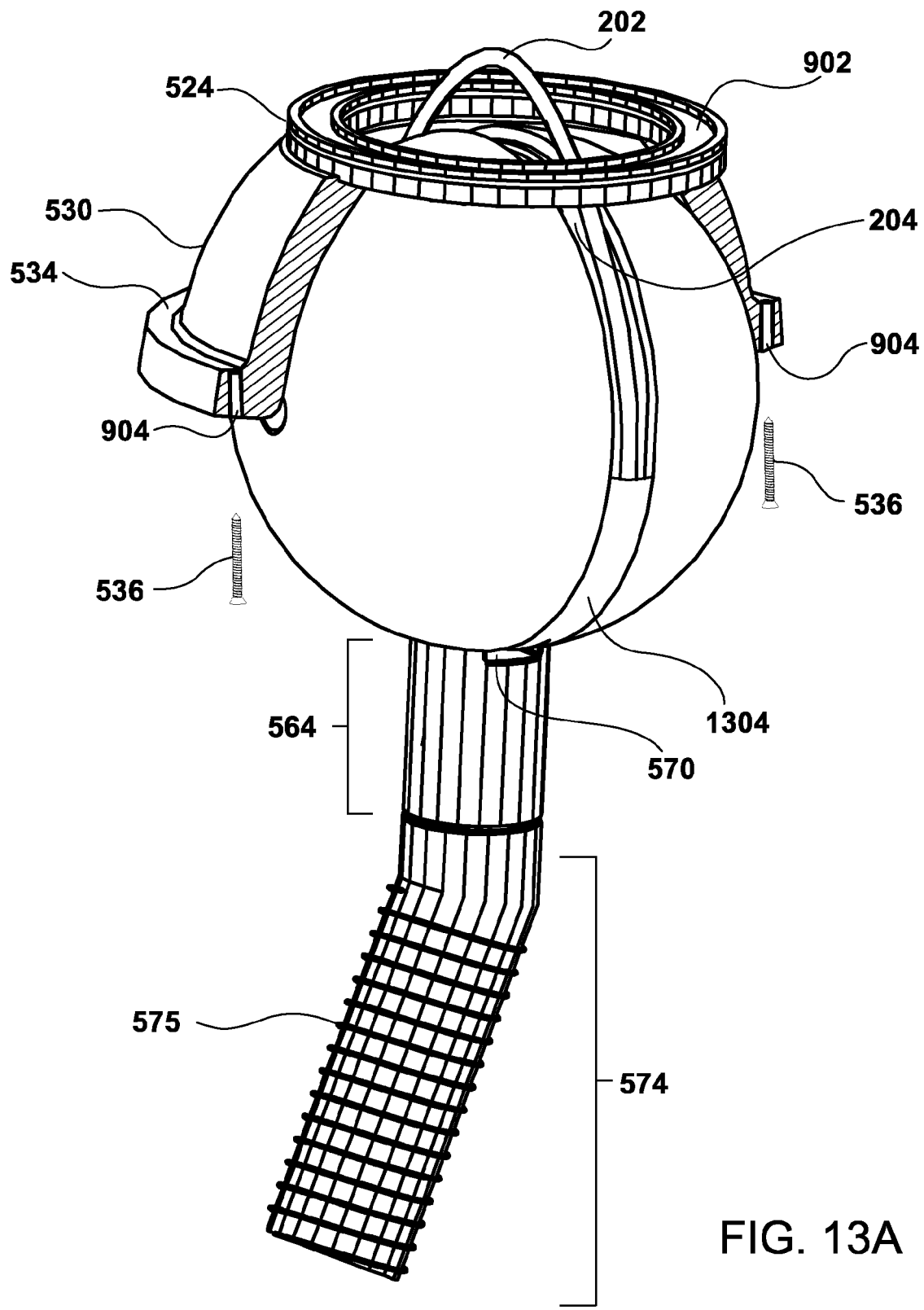
FIG. 13A is a perspective partial cross section view of an embodiment with a retaining sheath around the head-cable.

In another embodiment, a sheath 1304 encloses the head-cable 202 for a portion (optionally and preferably the complete length) of the head-cable 202 that does not need to come out of the head-groove 204 to begin to loop around the cup-cable 526 during usable head rotation (see FIG. 13A).

Figure 15A:
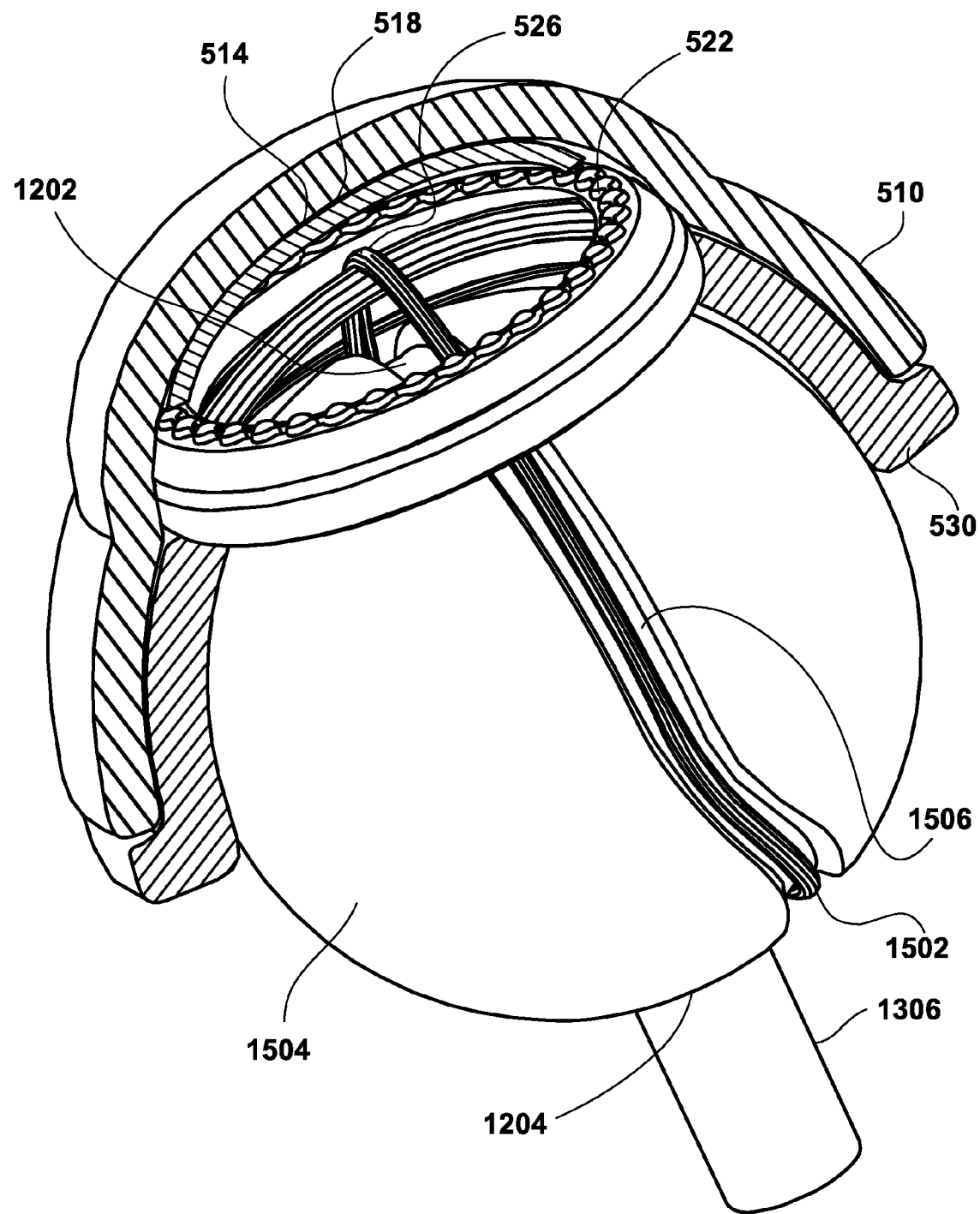
FIG. 15A is a perspective, partial cross section view of an embodiment with a cable detouring around the south pole of the head.
Figure 15B:
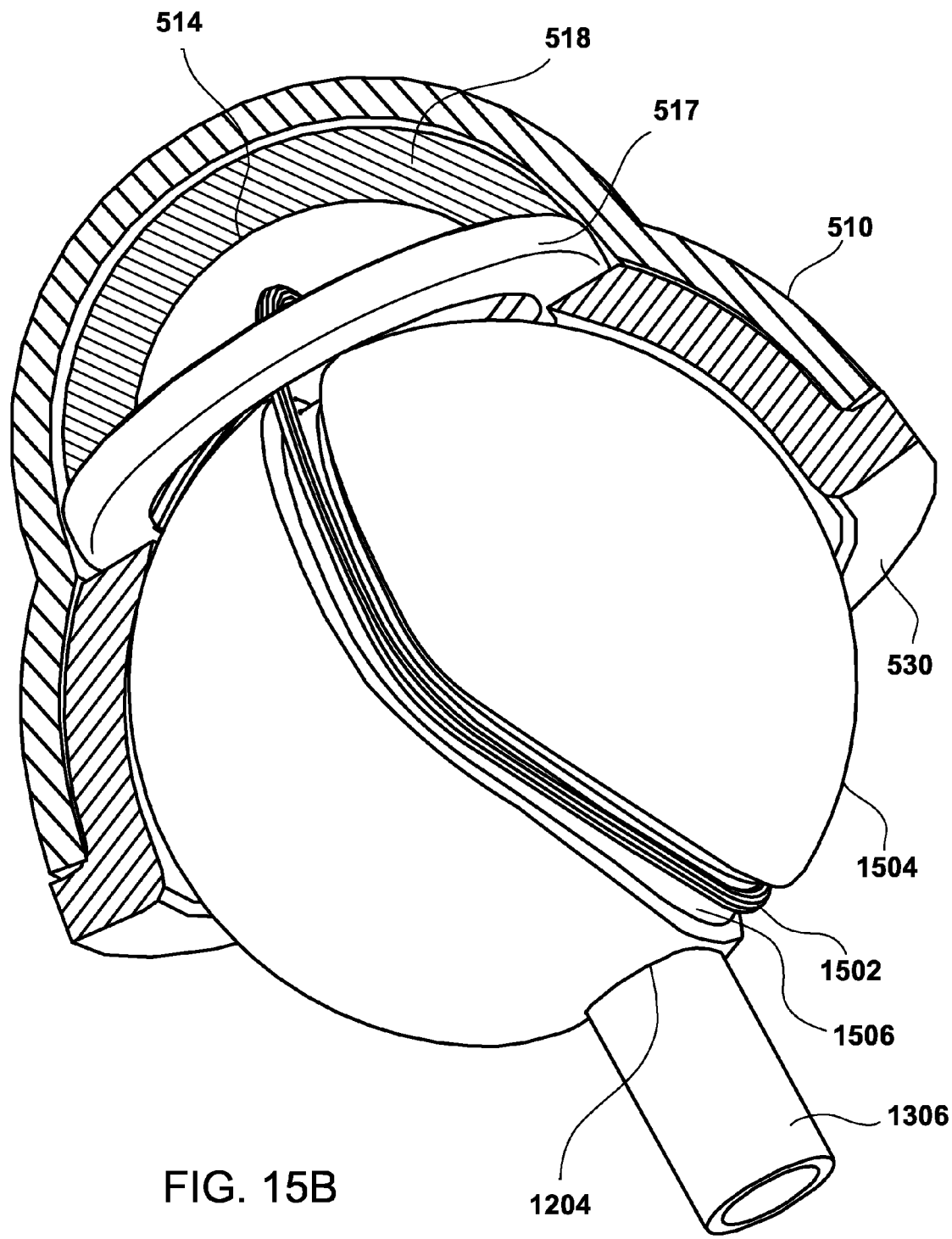
FIG. 15B is a different perspective, partial cross section view of the embodiment of FIG. 15A.

In yet another embodiment (see FIGS. 15A-15B), the head-cable 1502 and/or head groove 1506 in the head 1504 do not go around the south pole of the head 1204, though the head-cable 1502 does make a complete loop (no breaks in the head-cable 1502), obviating the need for a hole 570 between the stem 110 and the south pole of the head 1204, making the formerly pronged portion 564 into a non-pronged portion 1306. Again, the geometry of the swerve around the south pole of the head 1204 must 1) allow for usable head rotation and 2) if no sheath (similar to the sheath 1304 in FIG. 13A) is used around the head-cable 1502, not allow for the head-cable 1502 to slip out of the head-groove 1506 during usable head rotation.

In yet another embodiment (see FIG. 13B), the head-cable 202 and/or head-groove 204 do not go all the way down to the south pole of the head 1204 and loop around it, but attach 1302 to the head 1308 at certain latitudes above the south pole of the head 1204 at each end. The latitudes at each end where the head-cable 202 attaches 1302 to the head 1308 must allow for usable head rotation, and the formerly pronged portion becomes non-pronged 1306 because the head-cable 202 no longer needs a hole 570 to go through.

Figure 14A:
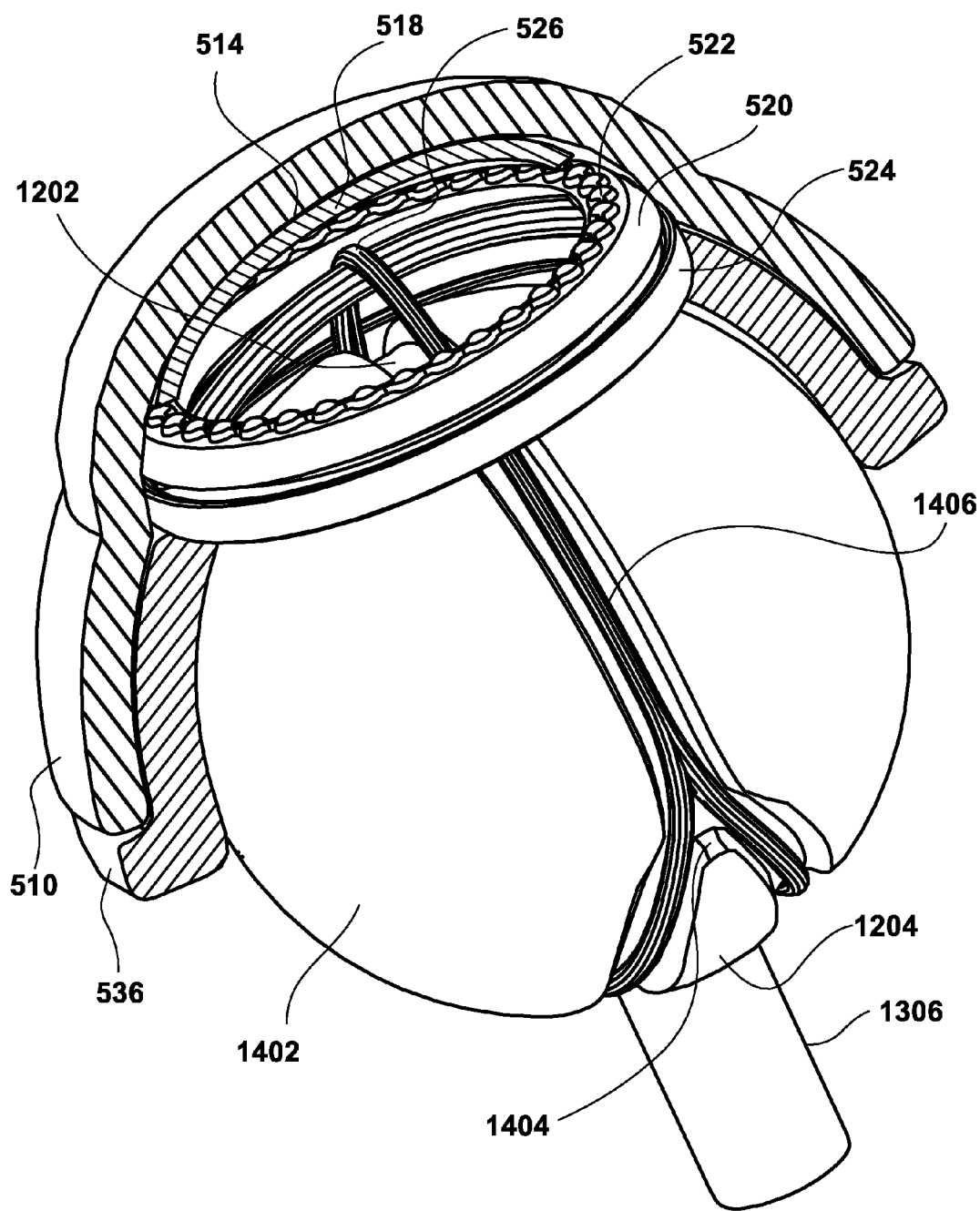
FIG. 14A is a perspective, partial cross section view of an embodiment with a forked cable around the south pole of the head.
Figure 14B:
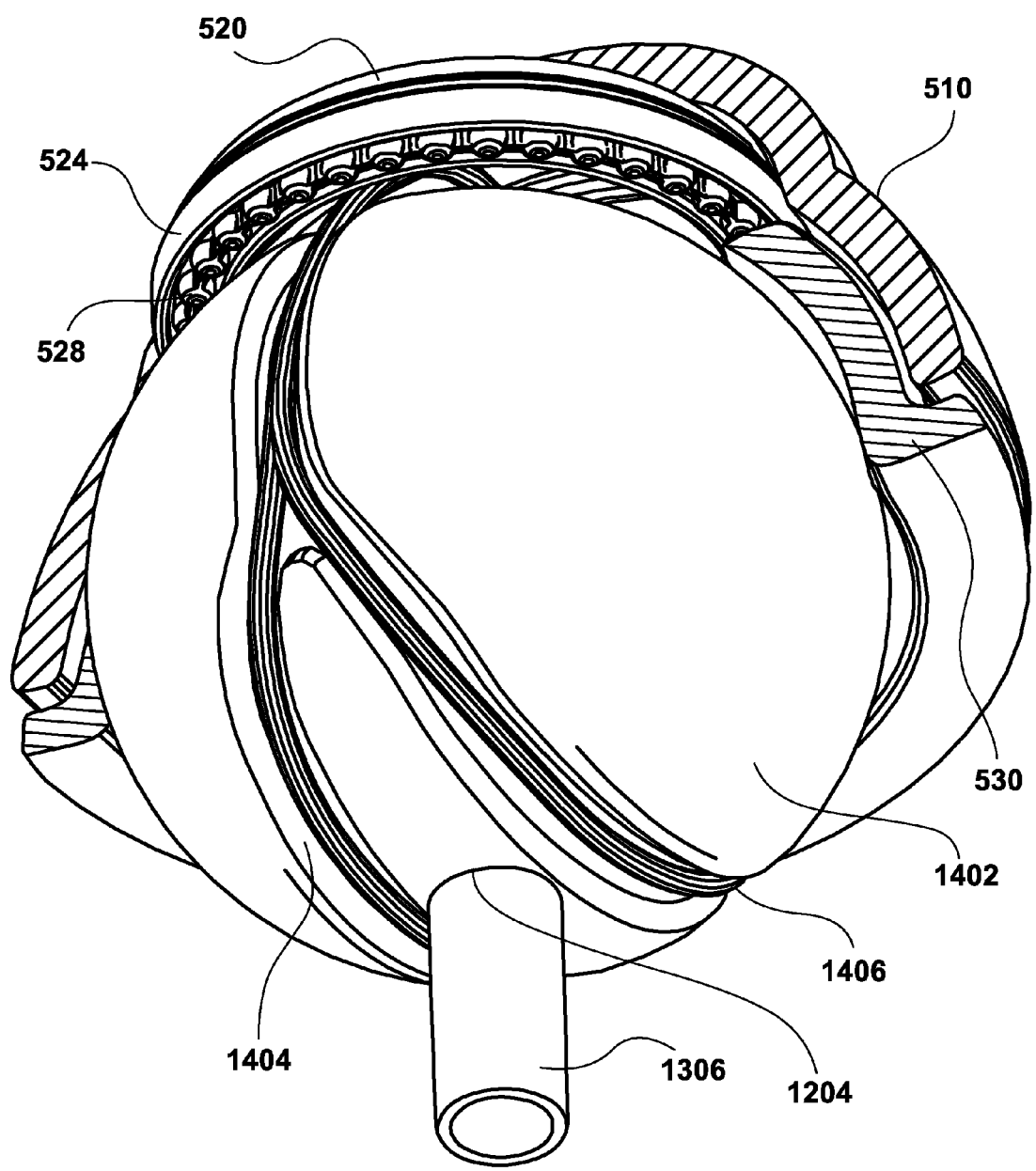
FIG. 14B is a different perspective, partial cross section view of the embodiment of FIG. 14A.

In another embodiment (see FIGS. 14A-14B), the head-cable is forked 1406 (with accommodating forked head-groove 1404) around the south pole 1204 of the accommodating head 1402, again obviating the need for a hole 570 between the stem 110 and the south pole of the head 1204, making the pronged portion 564 into a non-pronged portion 1306. Again, the geometry of the swerve around the south pole of the head 1204 must 1) allow for usable head rotation and 2) if no sheath (similar to the sheath 1304 in FIG. 13A) is used around the head-cable 1502, not allow for the head-cable 1406 to slip out of the head-groove 1404 during usable head rotation.

Figure 16B:
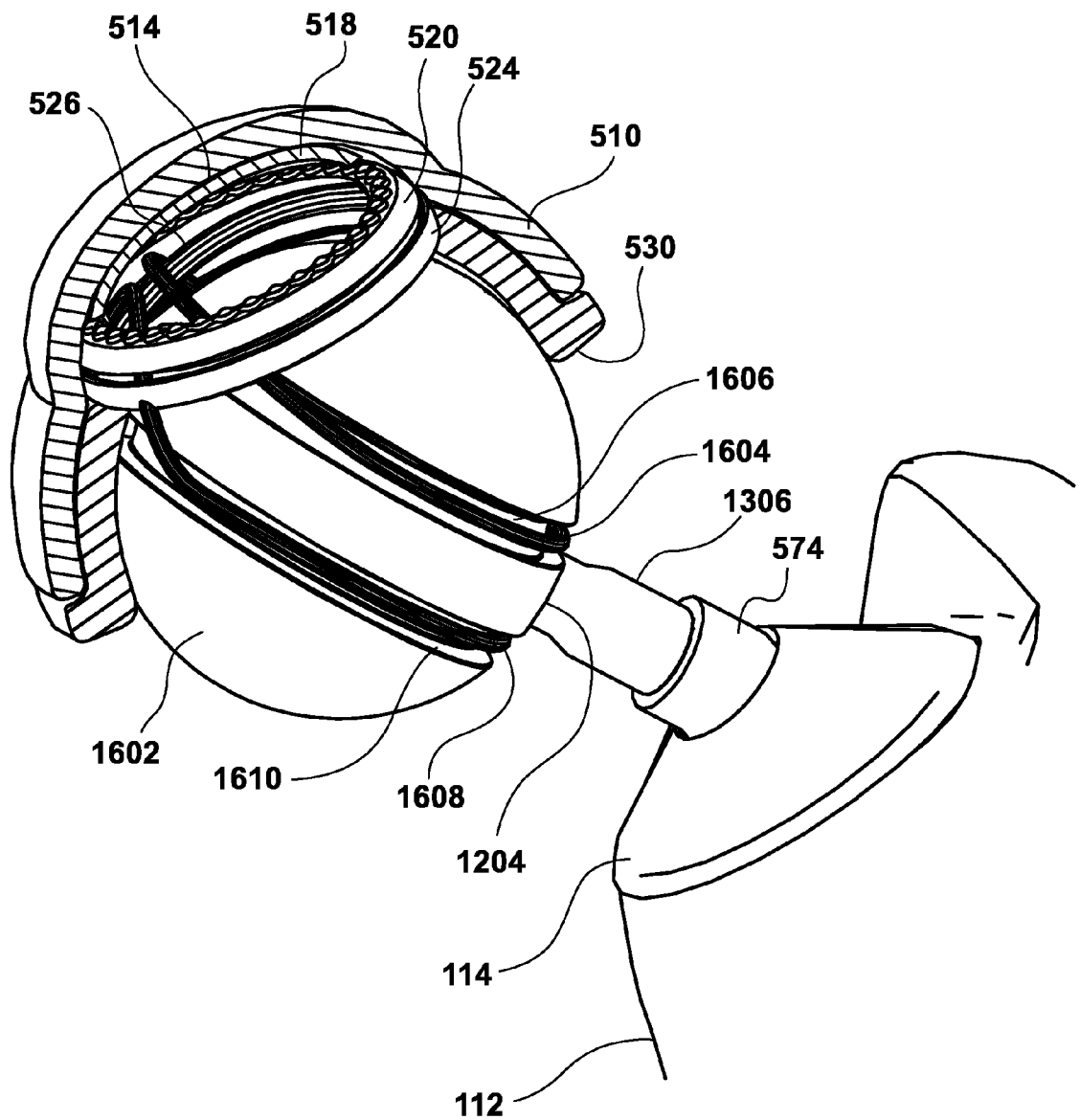
FIG. 16B is a different perspective, partial cross section view of the embodiment of FIG. 16A.

In yet another embodiment (see FIGS. 16A-16B), instead of one head-cable 108, one head-cable 1604 in a head-groove 1606 is used on one side of the south pole of the head 1204, and another head-cable 1608 in a head-groove 1610 in an accommodating head 1602 is used on the other side of the south pole of the head 1204, again obviating the need for a hole 570 between the stem 110 and the south pole of the head 1204, making the pronged portion 564 into a non-pronged portion 1306. Again, the geometry of each head-cable 1608 around the south pole of the head 1204 must 1) allow for usable head rotation and 2) if no sheath (similar to the sheath 1304 in FIG. 13A) is used around the head-cable 1502, not allow for the head-cable 1608 to slip out of the head-groove 1610 during usable head rotation. Note that any number of head-cables 1608 may be used, so long as they allow for usable head rotation. It is best to have the head-cables 1608 parallel, but they may be non-parallel if they still allow for usable head rotation.

Figure 17:
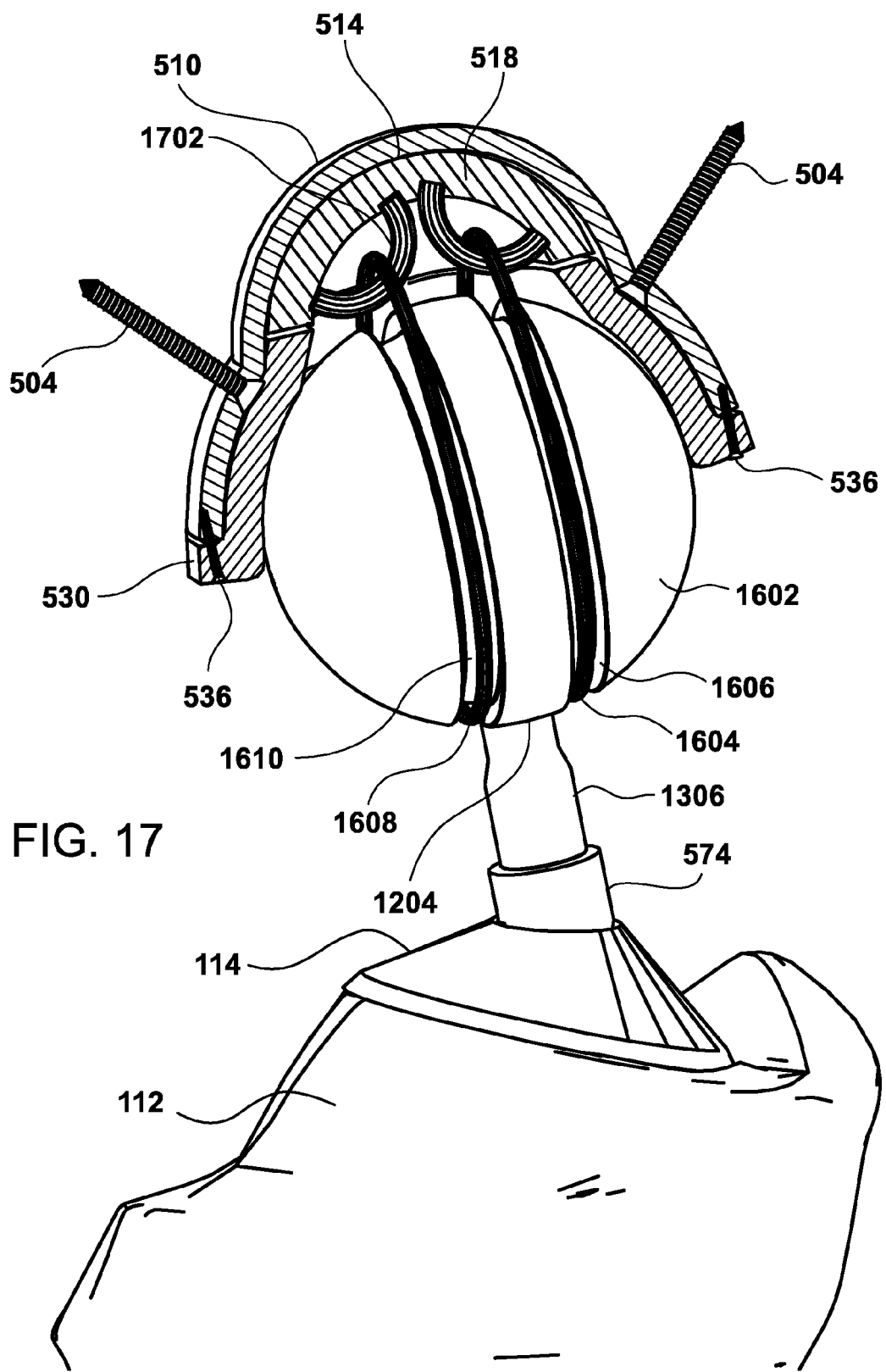
FIG. 17 is a perspective, partial cross section view of an embodiment with two head-cables, each of which loops around a separate cup-cable.

In yet another embodiment (see FIG. 17), the above embodiment (in the previous paragraph) with multiple head-cables is changed by replacing the cup-cable 526 with two cup-cables 1702. Again, the geometry must allow for usable head rotation. It is optionally useful to have stretchable head-cables to obtain more degrees in the range of motion along each axis.

Figure 20:
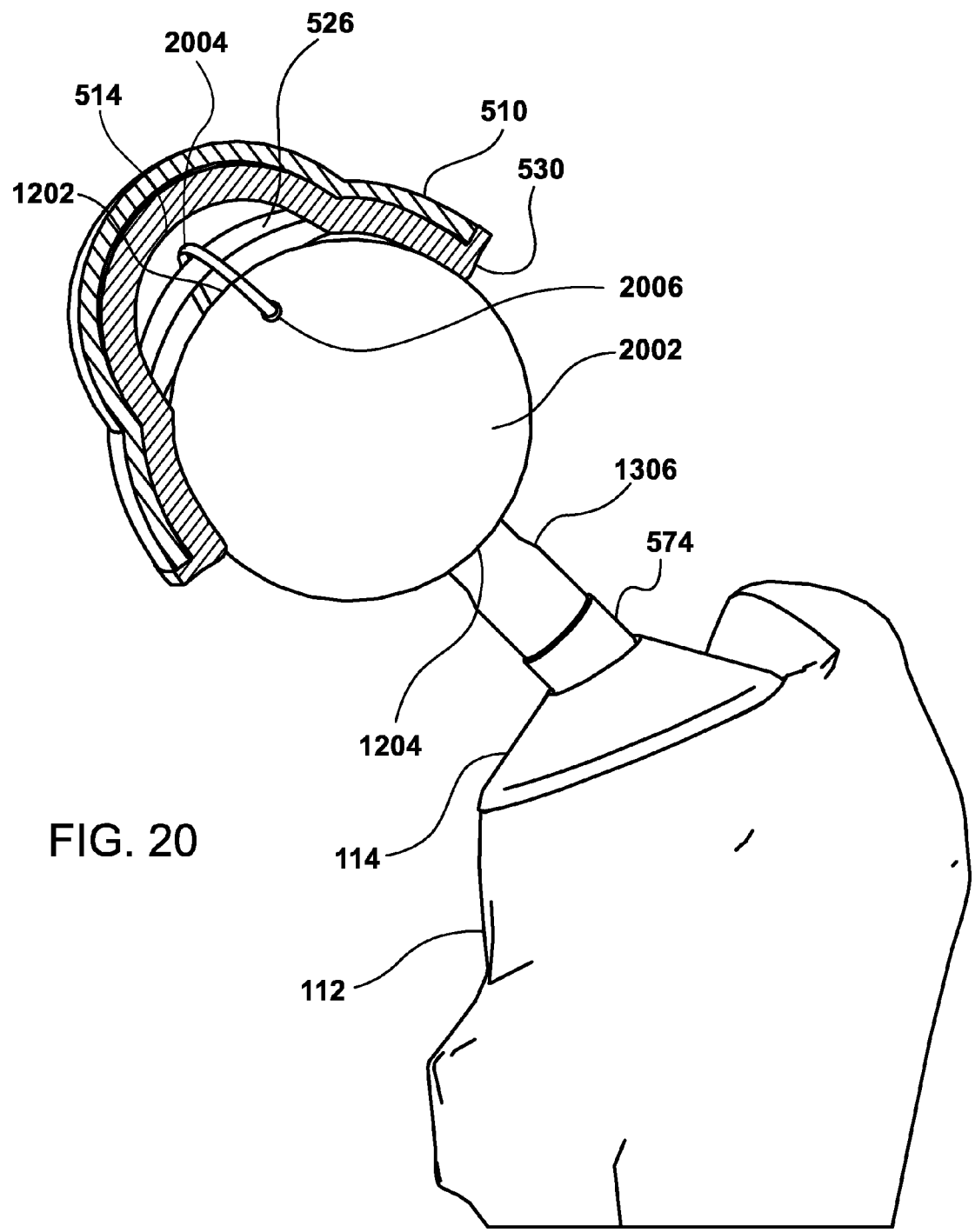
FIG. 20 is a perspective, partial cross section view of an embodiment where the head-cable attaches at each of its two ends at some point along the northern hemisphere of the head.
Figure 21:
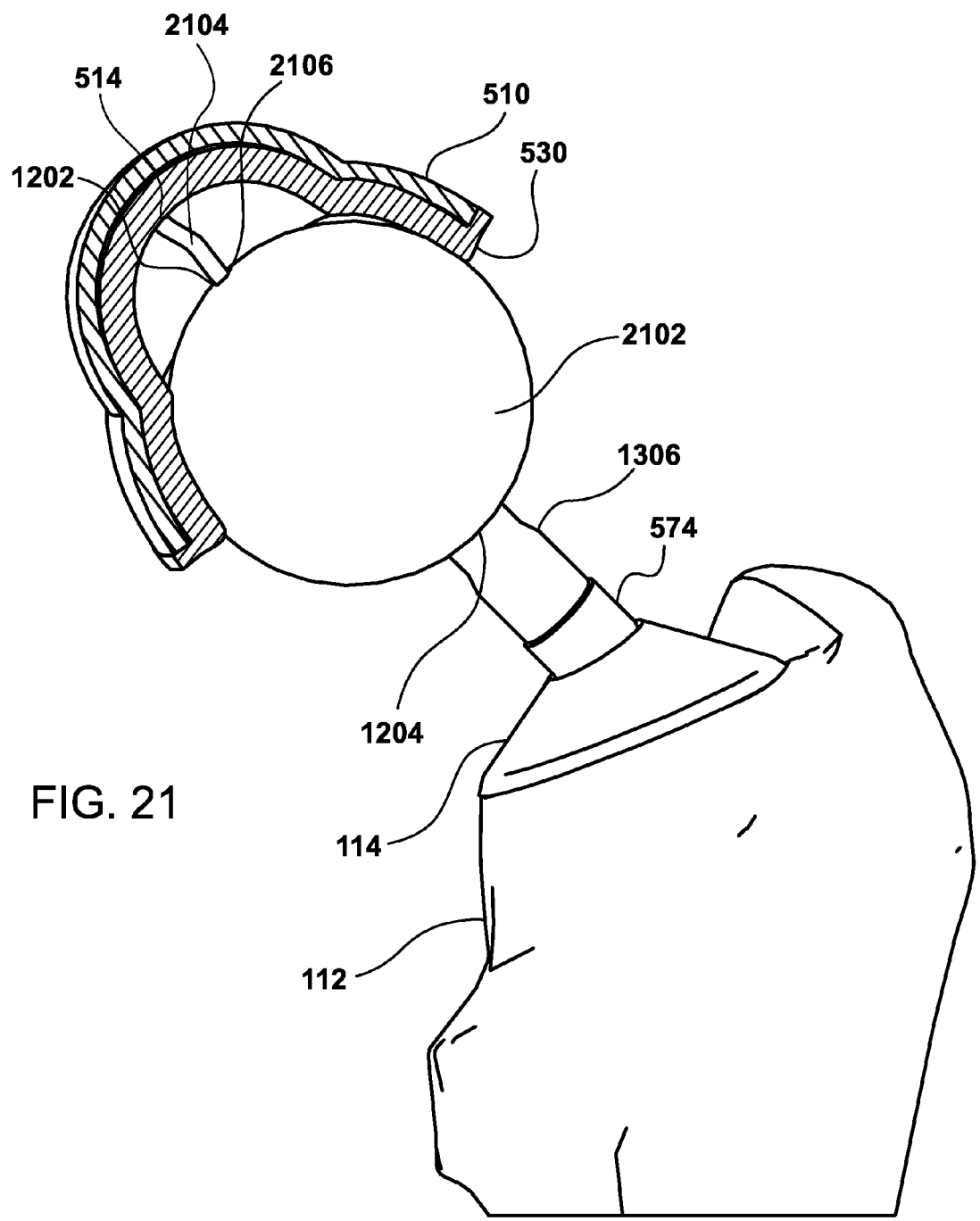
FIG. 21 is a perspective, partial cross section view of an embodiment where the head-cable attaches from the north pole of the cup to the north pole of the head.

In yet another embodiment (see FIG. 20), the head-cable 2004 does not have any head-groove 204 but attaches to the head 2002 at two points 2006 in the northern hemisphere of the head 2002, again obviating the need for a hole 570 between the stem 110 and the south pole of the head 1204, making the pronged portion 564 into a non-pronged portion 1306. Optimally, the head-cable 2004 attaches at each end at 45 degrees from the north pole of the head 1202 on opposite sides of the north pole, so as to allow the head 2002 to rotate 45 degrees in each direction along the line of the head-cable 2004 before either 1) the attachment point 2006 of the head-cable 2004 bangs into the inner surface of the cup 802, or 2) the head-cable 2004 catches on the cup-cable 526.

In yet another embodiment (see FIG. 2106), instead of using a head-cable 202 and cup-cable 526, a head-cup-cable 2104 to attach the inner surface of the cup 802 to the accommodating head 2102 with attachment point 2106. It is useful for the head-cup-cable 2104 to be stretchable and have room to unfold itself and become longer (like a snake uncurling), so as to increase the range of motion.

If it is not necessary for the head-cable to slide linearly relative to a head-groove, then the head-cable must just fit these requirements: 1) it must be able to loop around the cup-cable during usable head rotation; 2) it must not catch at the cup's equator between the head and the inner surface of the cup (through the cup-liner).)

Though not optimal, it is not necessary for the head-cable to be in the head-groove all of the way along the head, so long as usable head rotation is obtained.

Though the cup 106 is shown in the figures extending to the equator of the head and no further, the cup can extend down beyond the equator of the head into the southern hemisphere, so long as usable head rotation is obtained. This can be used as an additional safeguard to keep the head from dislocating from the socket, but sacrifices range of motion to the extent it encircles the head.

C. The cup: The cup is comprised of an inner surface 802 and an outer surface 511, the outer surface 511 fastened to the cup bone and the head fitting within the cup's inner surface 802. (See for example FIG. 5 for components mentioned in this paragraph).

The inner surface 802 is comprised of a spherical portion 506 and a super-spherical (hollowed out beyond spherical) portion 508.

Optionally and preferably the super-spherical portion 508 of the inner surface of the cup 802 viewed from the side is a portion of a circle with its center the same as the spherical portion 506 but with a larger radius, also optionally with sides that jut inward allowing the cup-cable 526 to contact the inner surface of the cup 802 at a perpendicular angle. However, so long as the cavity 804 allows room for the head-cable 202 to loop around the cup-cable 526 and rotate for usable rotation, there is enough concavity in the super-spherical cavity 804.

Spherical Portion:

The spherical portion 506 of the inner surface of the cup 802 "runs roughly all of the way around the inner surface of the cup along latitude lines, is located roughly closer to the cup's equator than the super-spherical portion, and extends approximately up from the equator to a certain latitude on the inside surface of the cup" [meaning also covering enough surface area along the head's equator 1206 to accomplish the following: 1) once fitted into the spherical portion 506 of the socket/cup 106, the head 108 cannot move translationally further into the socket 106; and 2) the surface area of the portion where the head 108 contacts the cup-liner 531 is sufficient such that any debris buildup caused by rubbing of the head 108 and the inner surface of the cup 802 against the cup liner 531 does not unduly impair operation of the apparatus nor the patient's health, rendering the hip implant unsafe to implant]. Alternatively, the "inner surface wherein a portion of the inner surface running from the cup's equator to a more northerly latitude" is defined to runs all of the way around the inner surface of the cup along latitude lines, extends upward from the cup's equator to a particular latitude (for example, 5, 10, 20, 45 degrees upward from the cup's equator, these examples not meant to be limiting).

Super-Spherical Portion:

The super-spherical portion 508 of the inner surface of the cup 802 "runs roughly all of the way around the cup along latitude lines, is located roughly closer to the cup's north pole, and extends down approximately from the cup's north pole to said certain latitude on the inner surface of the cup" [meaning also covering enough surface area to allow usable rotational movement both along the line of the cup-cable 526 and along the line of the head-cable 202]. Alternatively, there can be "a portion of the inner surface running from the more northerly latitude to the north pole of the cup", wherein the super-spherical (same meaning as "hollowed out super-spherically") portion runs all of the way around the cup along latitude lines, and runs down latitudinally from the north pole of the inner surface of the cup to the latitude at which the spherical portion begins.

Connecting the Cup to the Cup-Bone:

The cup 106 is fastened to the cup-bone, either directly or indirectly through a mounting plate (or other combination of parts) (optionally and preferably with two screws into the cup-bone).

Divisions of Cup:

The cup 106 is comprised of an inner surface 802 and an outer surface 511, the outer surface 511 fastened to the cup bone (for example, hip bone 102 or shoulder framework fitting around the cup 404) and the head 108 fitting within the cup's inner surface 802. The inner surface 802 is comprised of a spherical portion 506 and a super-spherical 508 (hollowed out beyond spherically) portion.

Figure 22A:
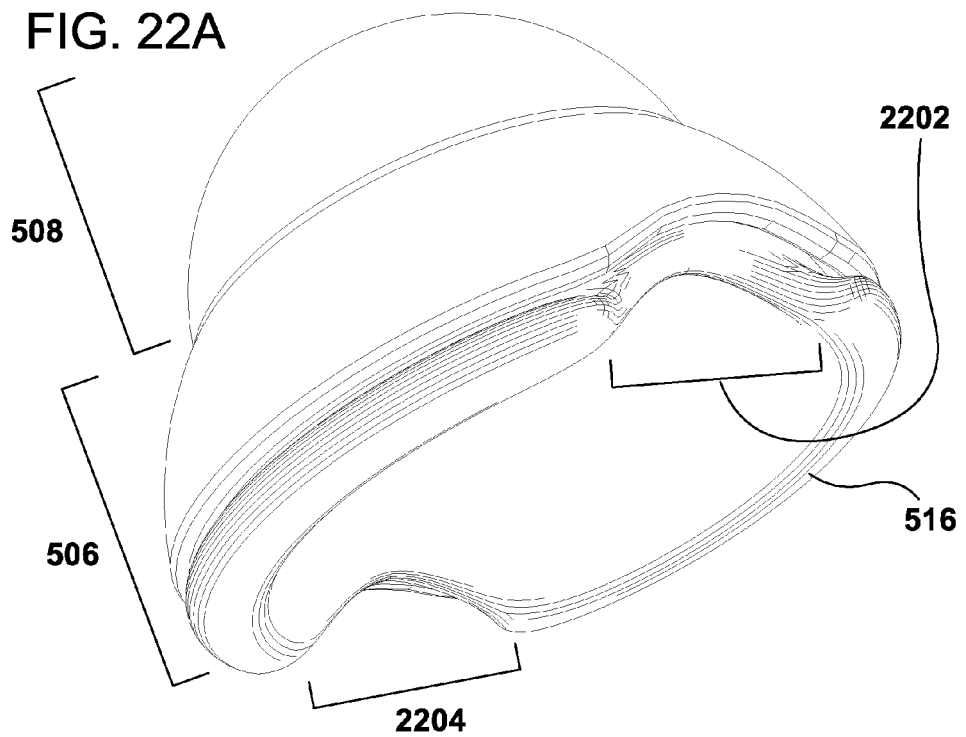
FIG. 22A is a perspective, partial cross section view of the embodiment in FIG. 5 with a recess in the cup at each end along the line of the head-cable.
Figure 22B:
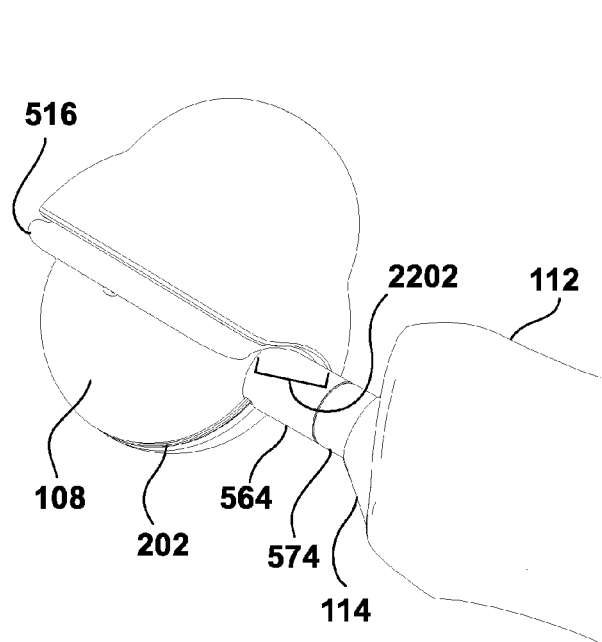
FIG. 22B is a perspective, partial cross section view of the embodiment in FIG. 22A with head and other parts added.
Figure 22C:
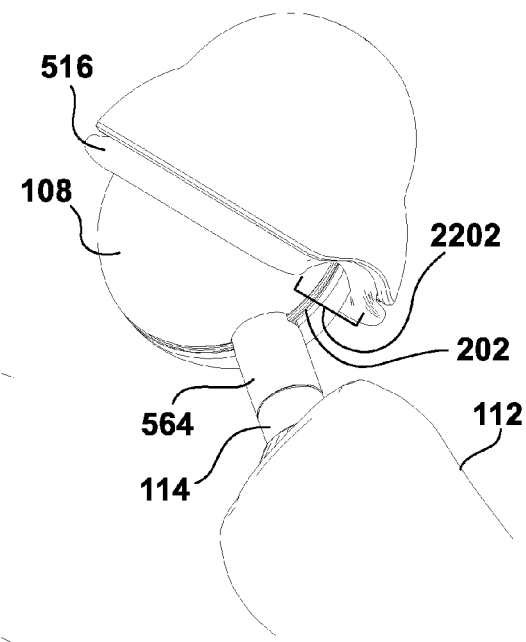
FIG. 22C is a perspective, partial cross section view of the embodiment in FIG. 22A with head and other parts added and head articulated.

In yet another embodiment (See FIGS. 22A-C), the portions of the cup along the cup's equator are recessed along the line of the head-cable 202 (with one recess 2202 at one side, and another recess 2204 on the opposite side), allowing the stem 110 room to swing up beyond 180 degrees (see FIG. 22B) along the line of the head-cable. Note that the cup-liner 531 must also similarly be recessed.

Optionally, the cup liner lines 531 at least the spherical portions of the inner surface of the cup 802 and contacts the inner surface of the cup 802 on one side and the head 108 on the other side. (See for example FIGS. 3, 5).

Optionally, a locking ring for the cup liner 531 holds the cup liner 531 in place, such as found in U.S. Pat. No. 7,766, 971, hereby incorporated by reference.

The cup-cable 526 runs "roughly parallel to the surface of the head above the north hemisphere and roughly perpendicular to the head-groove" [meaning parallel enough to the surface of the head and perpendicular enough relative to the head-groove to allow for usable head rotation], attached at each end at a point on the super-spherical portion of the inside surface of the cup (optionally with a lip that allows the cup-cable to contact the inside surface of the cup at a perpendicular angle). (See for example, FIGS. 13A-B). Alternatively, the cup-cable can run exactly parallel to the surface of the head above the north hemisphere.

Figure 18A:
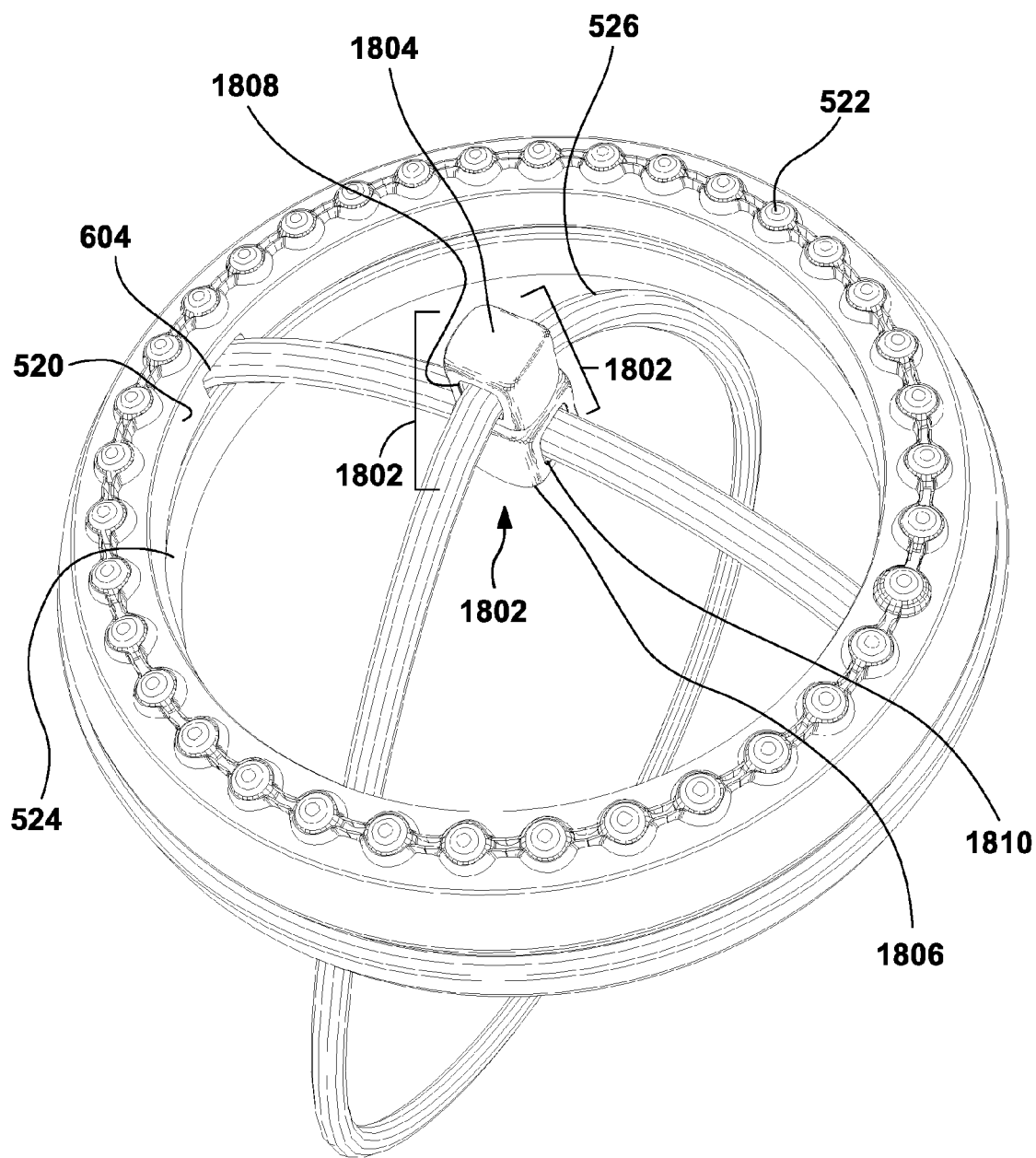
FIG. 18A is a perspective view of an interface (and surrounding parts) allowing the cup-cable and the head-cable each to slide along each cable's respective line relative to the interface.
Figure 18B:
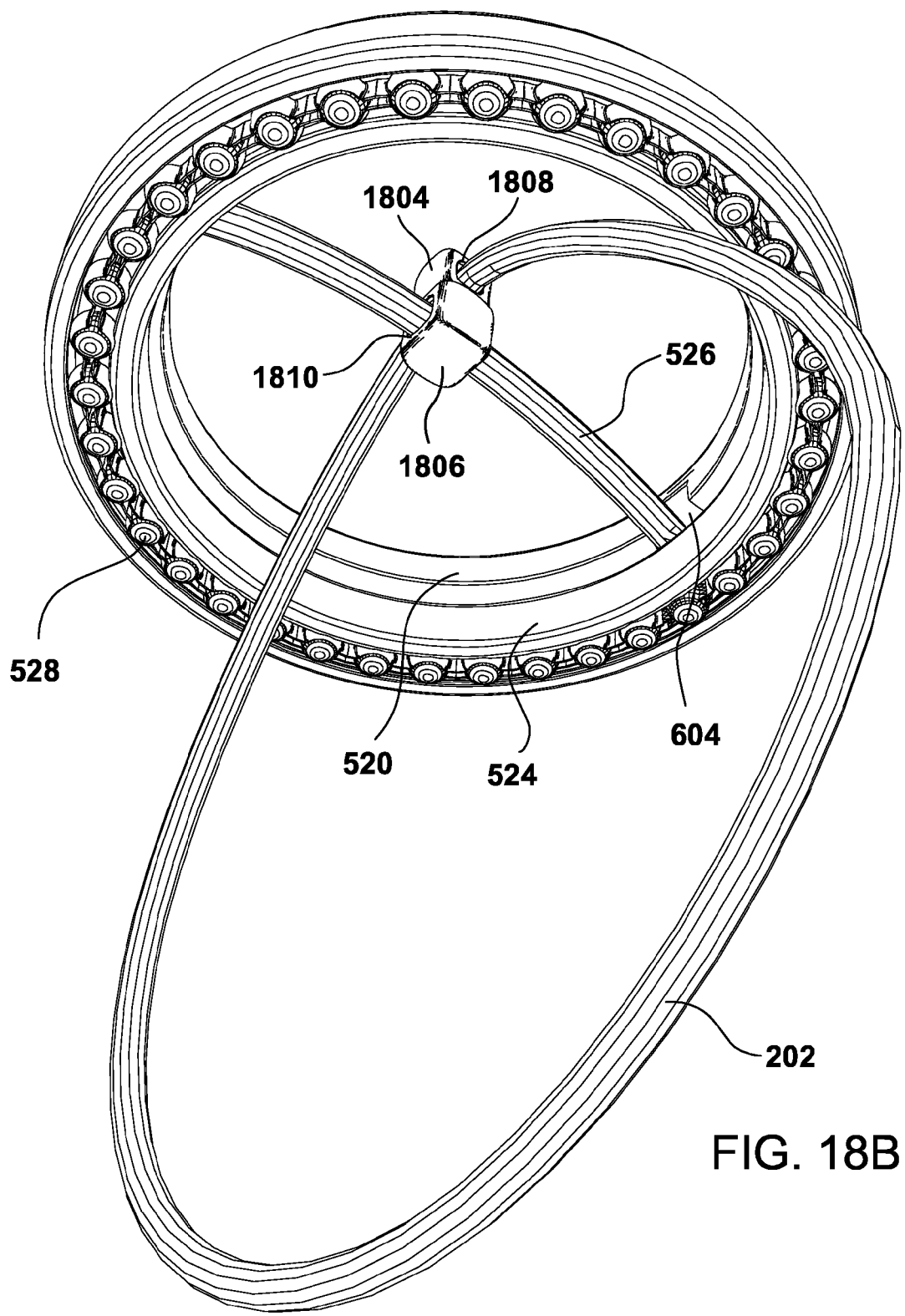
FIG. 18B is a different perspective view of the embodiment of FIG. 18A.
Figure 19A:
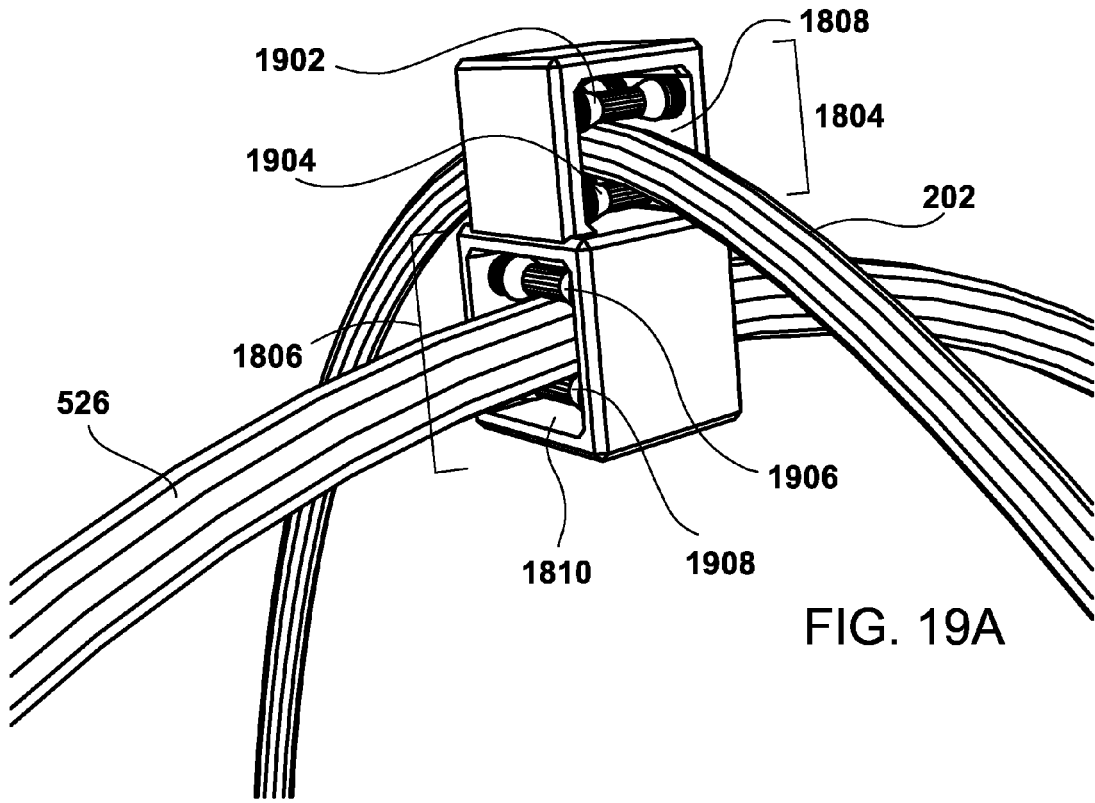
FIG. 19A is a perspective view of the embodiment of FIG. 18A, zoomed in relative to FIGS. 18A-B.
Figure 19B:
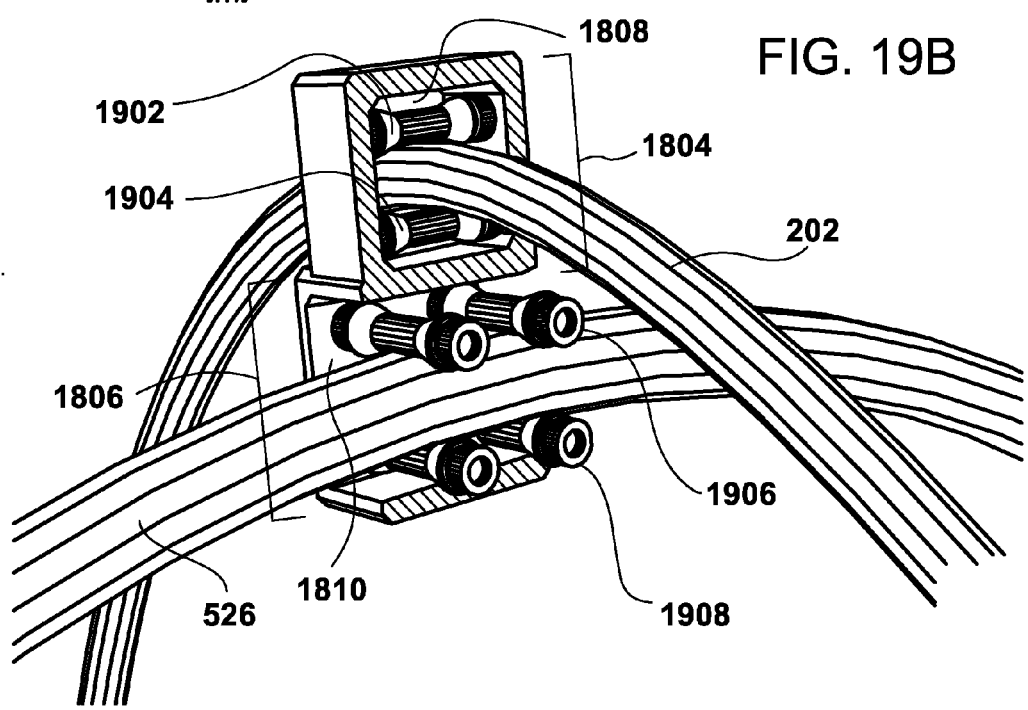
FIG. 19B is a perspective, partial cross section view of the embodiment of FIG. 18A, zoomed in relative to FIGS. 18A-B.

Cup-Cable/Head-Cable Interface:

In yet another embodiment (see FIGS. 18-19), the head-cable 202 can slide linearly relative to an interface 1802, while the cup-cable 526 can also slide linearly (though perpendicular to the head-cable 202) relative to the interface 1802. This allows the distance between the cup-cable 526 and the head-cable 202 to remain fixed for easier motion. The interface 1802 is composed of 1) a subunit 1804 with a hole 1808 for the head-cable 202 housing a roller bearing above the head-cable 1902 and a roller bearing below the head-cable 1904; and 2) a subunit 1806 with a hole 1810 for the cup-cable 526 housing a roller bearing above the cup-cable 1906 and a roller bearing below the cup-cable 1908. Note that any number of roller bearings (or other bearings, such as ball-bearings, or multiple sets of bearings) may be used, so long as the head-cable 202 and cup-cable 526 each can slide independently. It is also possible to have only the cup-cable 526 able to slide if ball-bearings 602 in the head groove 204 allow the head 108 to rotate independently of the head-cable 202.

More on the Swivel:

The swivel allows the head-bone to rotate along the z-axis (when you twist your leg (for the hip joint) or twist your shoulder (for the shoulder joint) in the axis pointing from the inner surface of the cup's north pole down to the head-bone, discussed earlier as "latitudinally"). Rotation along this z-axis is called "horizontal", resulting in the term "horizontal swivel." The swivel may be horizontal, or roughly horizontal enough to allow for usable head rotation, or anything in between. The swivel may be at any workable point between the head-bone and the cup-bone—thus, if it does not interfere with the functioning of the other parts of the apparatus, such points which should be obvious to one of ordinary skill in the art. The swivel also may be between the inner surface of the cup 802 and the cup-bone (for example, the hip bone 102 or the shoulder framework 404), or between the inner surface of the cup 802 and the head 108, or between the south 1204 pole of the head and the head-bone (for example, the femur 112 or the humerus 402), or bisecting the head 108 (so shoulder framework 404) remains "substantially fixed" [meaning not susceptible to breakage or unusable bending that would render the hip implant unsafe to be implanted] (aside from the horizontal twisting afforded by the swivel) relative to the part adjacent to the swivel further from the cup-bone (for example, the hip long as it doesn't interfere with the head-cable 202 sliding in any head-grooves 204, and is sufficiently strong so that the part adjacent to the swivel closer to the cup-bone (for example, the hip bone 102 or the bone 102 or the shoulder framework 404)). The swivel is optional, as the head 108 may still rotate along either axis even if horizontally the head-cable 202 is not strictly perpendicular to the cup-cable 526.

It should be obvious to one of ordinary skill in the art, using the main concepts and the first version to work off of, to make and use different versions using a) various means of connection (instead of screws, substituting other ways of connecting the parts); b) splitting a given part into multiple parts (for instance, to allow for assembly of most parts outside of the body, and to allow parts to be more easily replaced (for instance, so the bone doesn't have to be drilled into)), and/or combining parts; c) varying numbers along ranges (for instance, the size of the head, exact shape of super-spherical cavity so long as it performs its function, exact latitude at which the inner surface of the cup shifts from super-spherical to spherical, exact placement and design of the horizontal swivel, among others); and/or d) omitting features so long as the function of usable head rotation is still served. While different type heads (or other parts) are referred to throughout, the usage of a specific reference numeral (such as 108) is not meant to constrain the meaning if other geometries (including but not limited to parts from other embodiments and/or other versions) are workable within the general inventive concept, but just to be an example.

It should be obvious to a person of ordinary skill in the art how to assemble any of the previously mentioned versions, with the following additional tips:

1. To assemble the head 108/head-cable 202/head to head-bone rod 218 complex when there is a south pole 1204 hole 570 in the end of the head to head-bone rod 218 which the head-cable 202 and head-groove 204 fit through, the head to head-bone rod 218 may have two prongs 571 that fit into the head 108 at the south pole of the head 1204, where the head-cable 202 loops around the beginnings of the prongs in the prongs hole 570 and turns along with the prongs 571 until the prongs 571 are fully screwed in. (If the head-groove 204 is to completely loop around the south pole of the head 1204, then after the head-cable 202 is inserted between the two prongs 571, then a piece with head-groove portion 577 facing the beginnings of the prongs 571 could be attached between the two prongs to complete the head-groove 204 between the prongs 571.) Or, instead of looping the head-cable 202 around prongs 571 in the head-head-bone rod 218 before the prongs 571 are screwed into the head 108, a section of one of the prongs 571 could be cut out and replaced (or just put in) after sliding the head-cable 202 between the two prongs 571. There are many other methods of assembling these parts, which should be obvious to one of ordinary skill in the art.

2. To loop the head-cable 202 around the cup-cable 526 while both will eventually end up in a covered cavity 804 between the inner surface of the cup 802 and the northern hemisphere of the head, there must be a hole adequate to allow the cup-cable 526 to be inserted properly between the head-cable 202 and the head 108 (if the preferred embodiment method detailed above of squeezing the cup-cable 526 between two parts of the cup 106 is not used)—with (see FIG. 8B) a hole 808 at either end of where the cup-cable 526 attaches with an accommodating cup 810 to the cup 810, or (see FIG. 8C) closer to the top of the cup, beginning with an accommodating cup 812 with an accommodating hole in the top 814 through which first the cup-cable 526 fits into the cavity 804 and then the hole 814 is closed by an accommodating piece 816 to fit into the cup 812.

Any number of variations of the above two methods of assembly, and/or other methods, should be obvious to one of ordinary skill in the art.

Each version may be used to create independent axes of rotational movement (through a combination of rotation along the line of the head-cable 202 (see FIGS. 11A-11B examples), along the line of the cup-cable 526 (see FIGS. 11C-11D), and twisting through the swivel), while still constraining the head translationally relative to the cup. The degrees of rotation along each axis are limited by physical constraints—i.e. when one part (such as a head-cable 202) runs into another part (such as the inner surface of the cup 802).

Piecemeal Version:

In another version, each axis of rotation is created piecemeal through "swivel devices" or "devices" that form a device assembly (which connects the cup-bone (such as the hip bone 102 or the shoulder framework 404) to the head-bone (such as the femur 112 or the humerus 402).

Figure 24A:
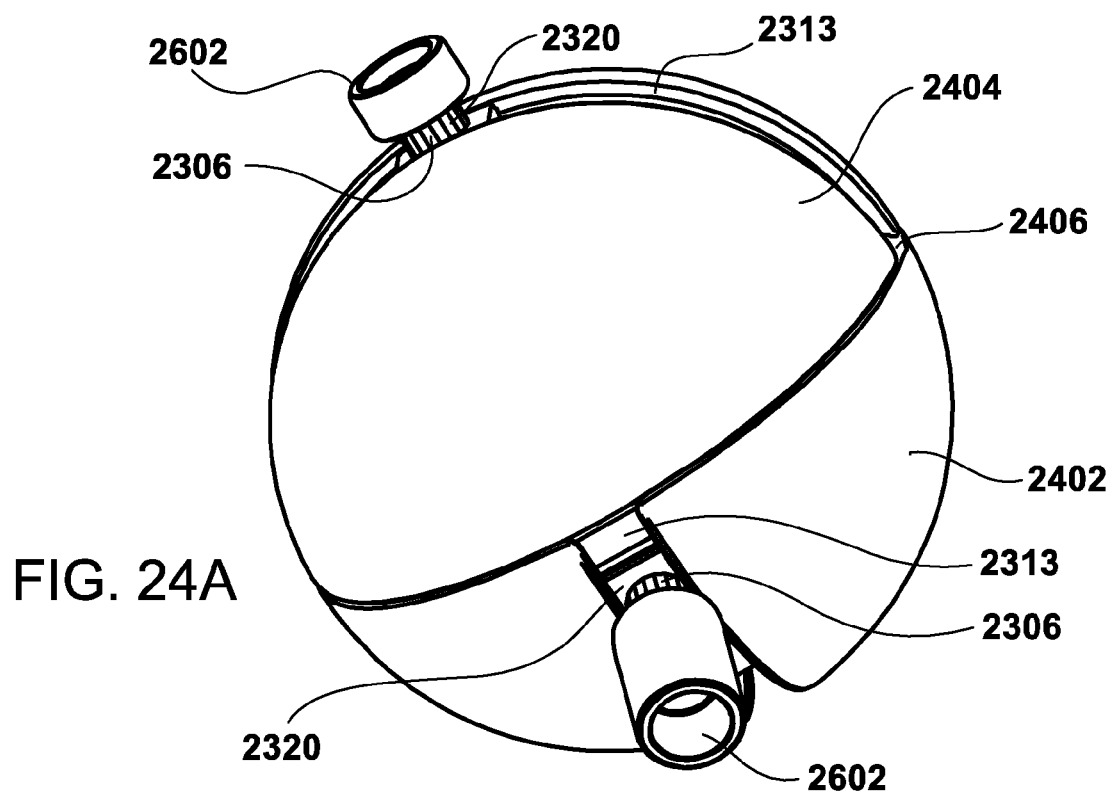
Figure 24B:
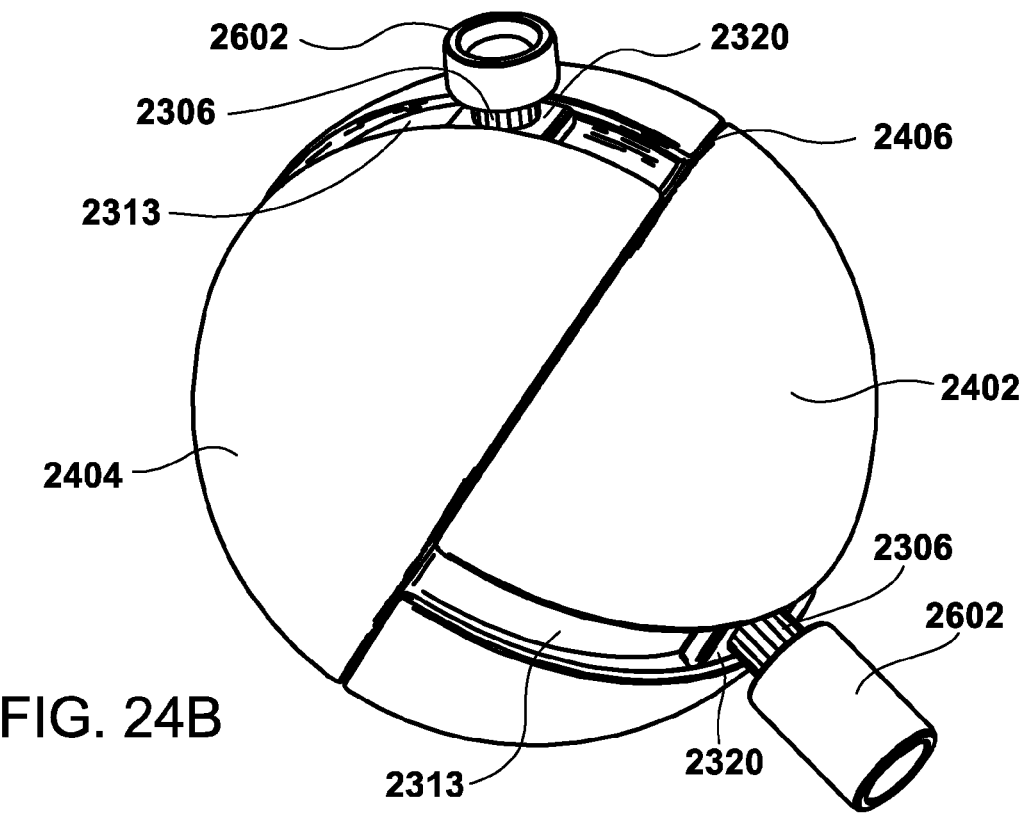
FIG. 24B is a different perspective view of the embodiment of FIG. 24A.
Figure 25A:
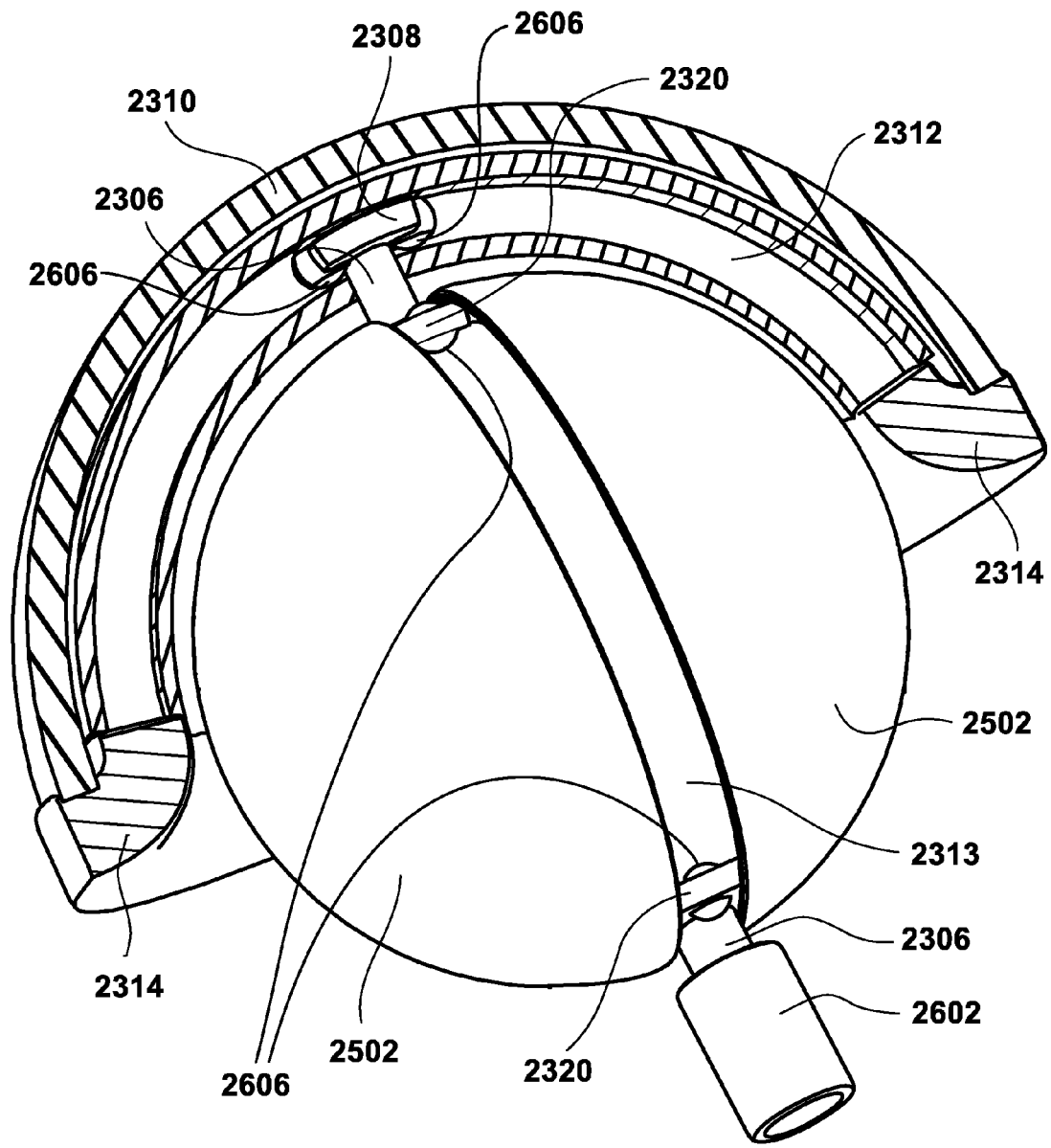
FIG. 25A is a perspective view of an embodiment with one outside track with knob, combined with two parallel inside tracks with knobs.
Figure 26:
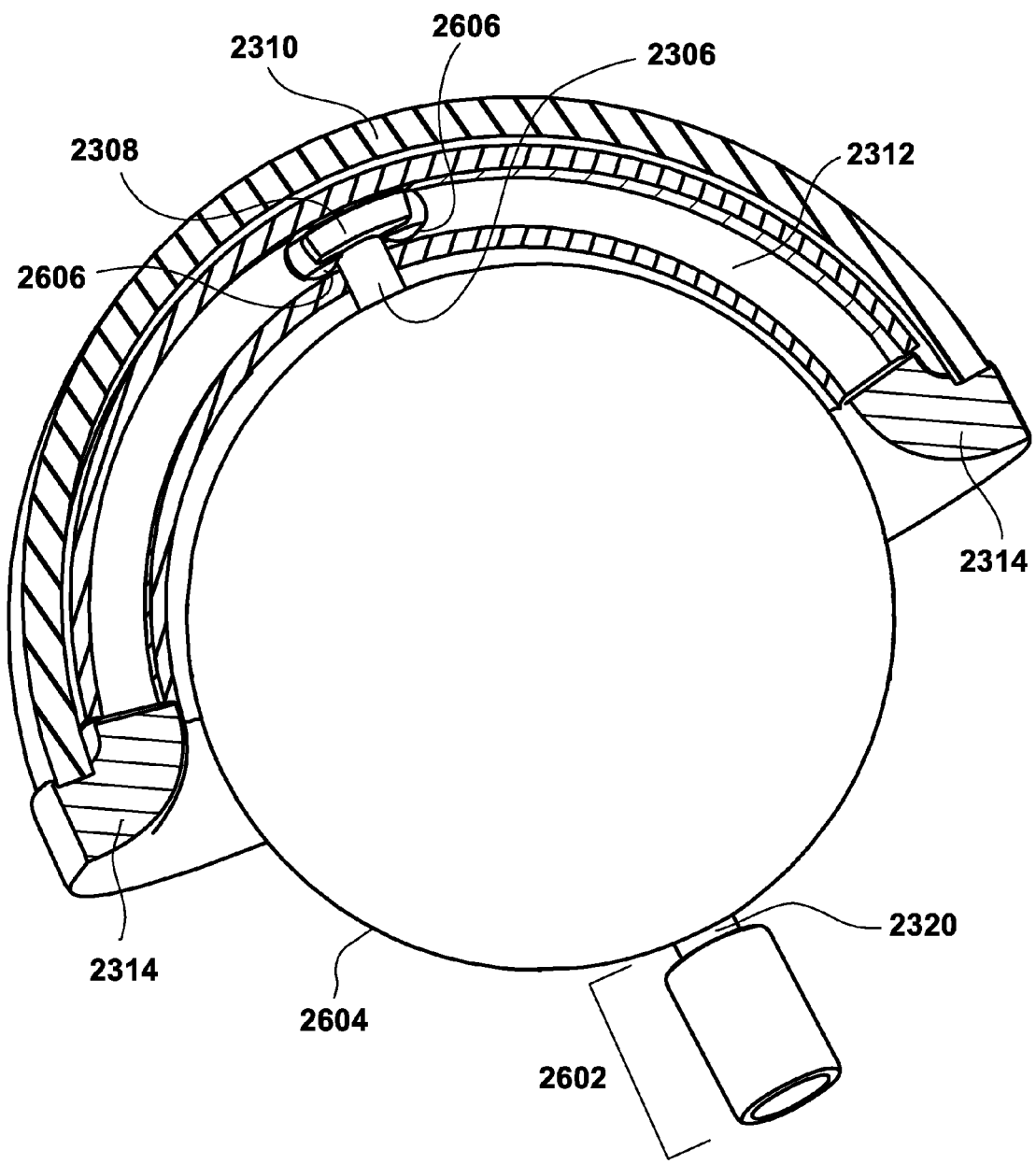
FIG. 26 is a perspective, partial cross section view of an embodiment with one outside track with knob.
Figure 27:
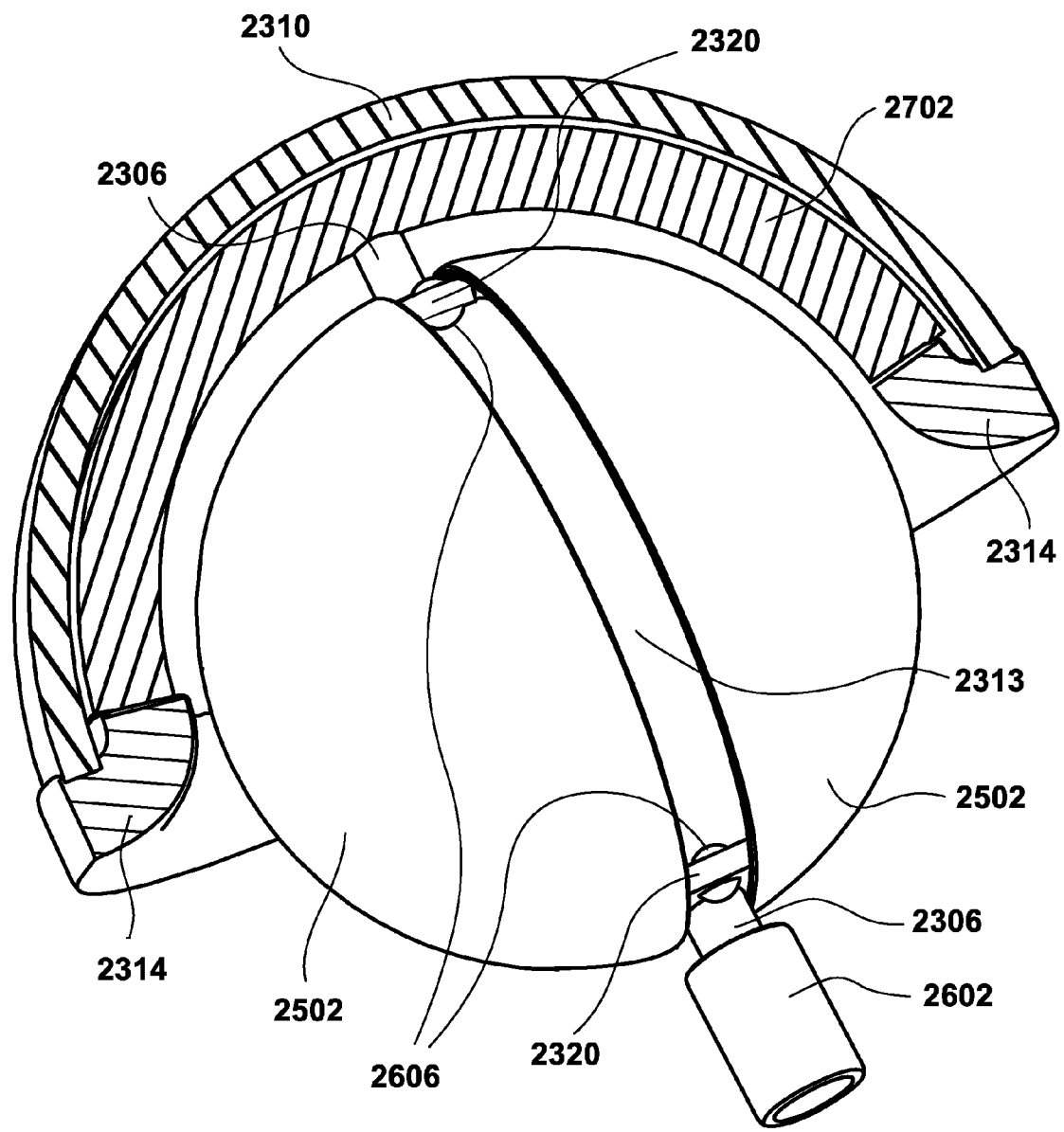
FIG. 27 is a perspective, partial cross section view of an embodiment with two inside tracks with knob.
Figure 28:
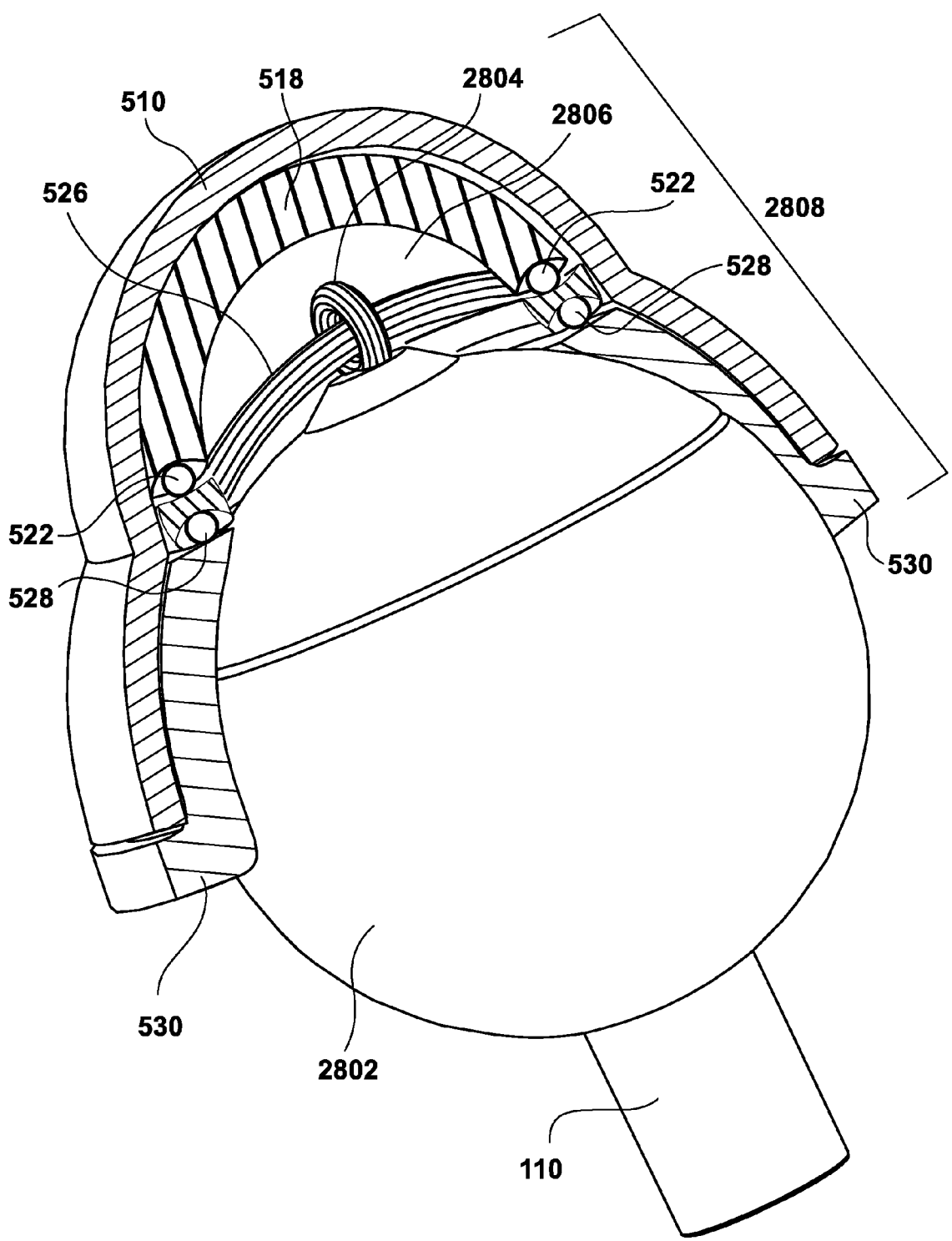
FIG. 28 is a perspective, partial cross section view of an embodiment with an outside track with ring around cable with a horizontal swivel.
Figure 29:
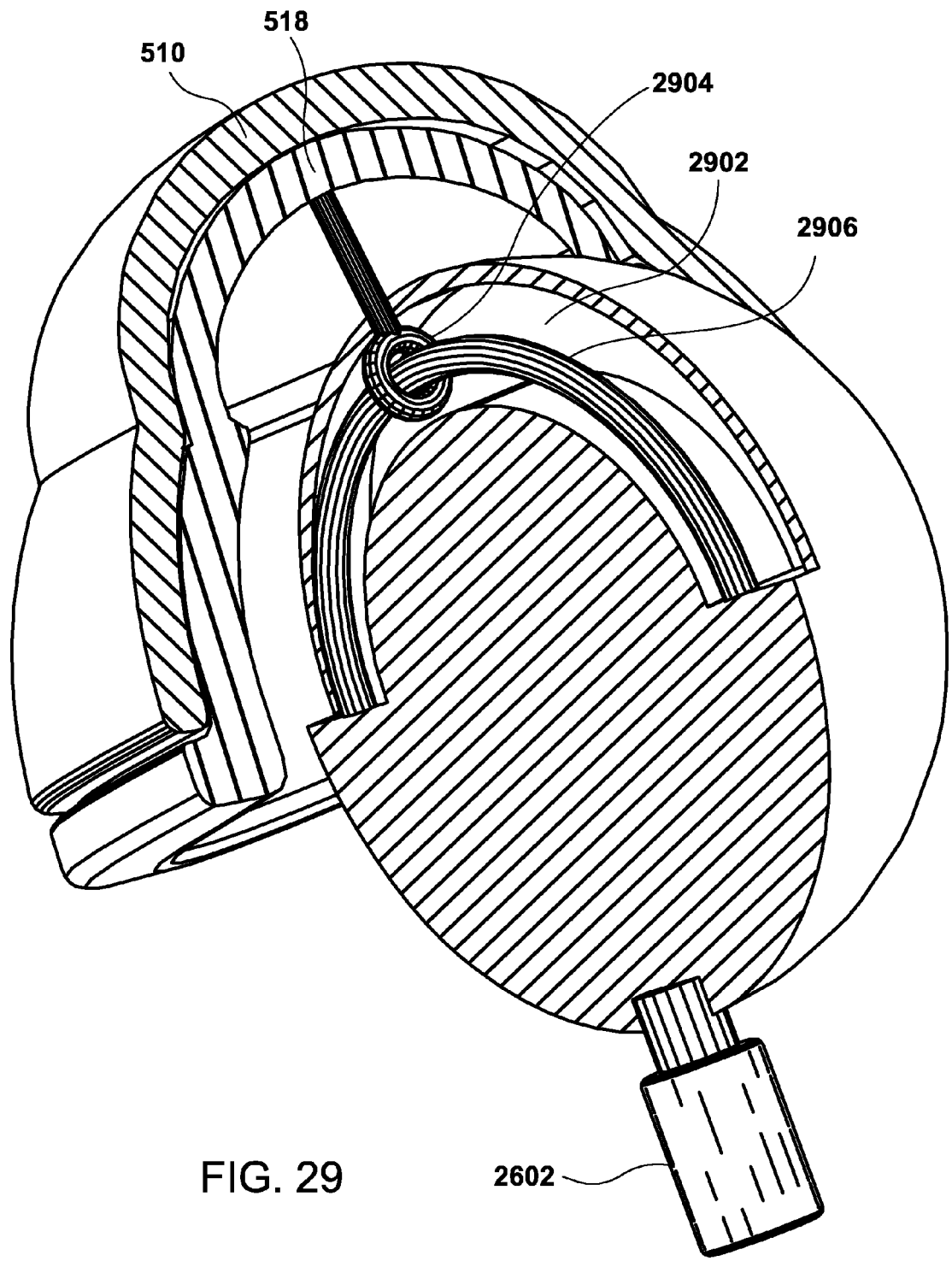
FIG. 29 is a perspective, partial cross section view of an embodiment with one inside track with ring around cable.

Each axis of rotation is created piecemeal through a "swivel device" that rotates around where the center of the head 108 would be, either through 1) a swivel with a lever (see for example FIGS. 30A-C), comprising a swivel whose axis of rotation crosses through the center of the head 108 with a lever 3004 extending perpendicular to said axis of rotation and outward from the center of where the head 108 would be, or 2) a cable that is caught within but slides smoothly along a circular track along a fixed radius from the center of the head (optionally with ball bearings interfacing between the cable caught in the track and the track), the cable being a permutation of the variables a) inside the head track (top left of FIGS. 26, 29) vs. along the cup track (top left of FIGS. 27, 28) and b) knob inside track (top left of FIGS. 26, 27) vs. ring around cable (top left of FIGS. 29, 28). To create two independent axes of rotation, the axis about which each device rotates is perpendicular to the other device's axis. Note that each device may be attached to separate sides of the head (see for example FIGS. 24A-24B with accommodating sides of head one 2402 and two 2404 and swivel in the middle of the head 2406, 31A-31B), or to each other (see for example top left of FIG. 25A)—the only constraint when selecting devices is that the lever device (see for example FIGS. 30A-30C) may only be used when pointing outward from the head's center. Each device or combination (when the devices are not on separate sides of the head but are connected to each other) of devices attaches the head to either the head-bone or to the cup-bone, and the connection between the head and the bone not connected by the combination (the cup-bone or the head-bone, if two separate devices are not used) does not have to (but may) rotate.

Figure 25B:
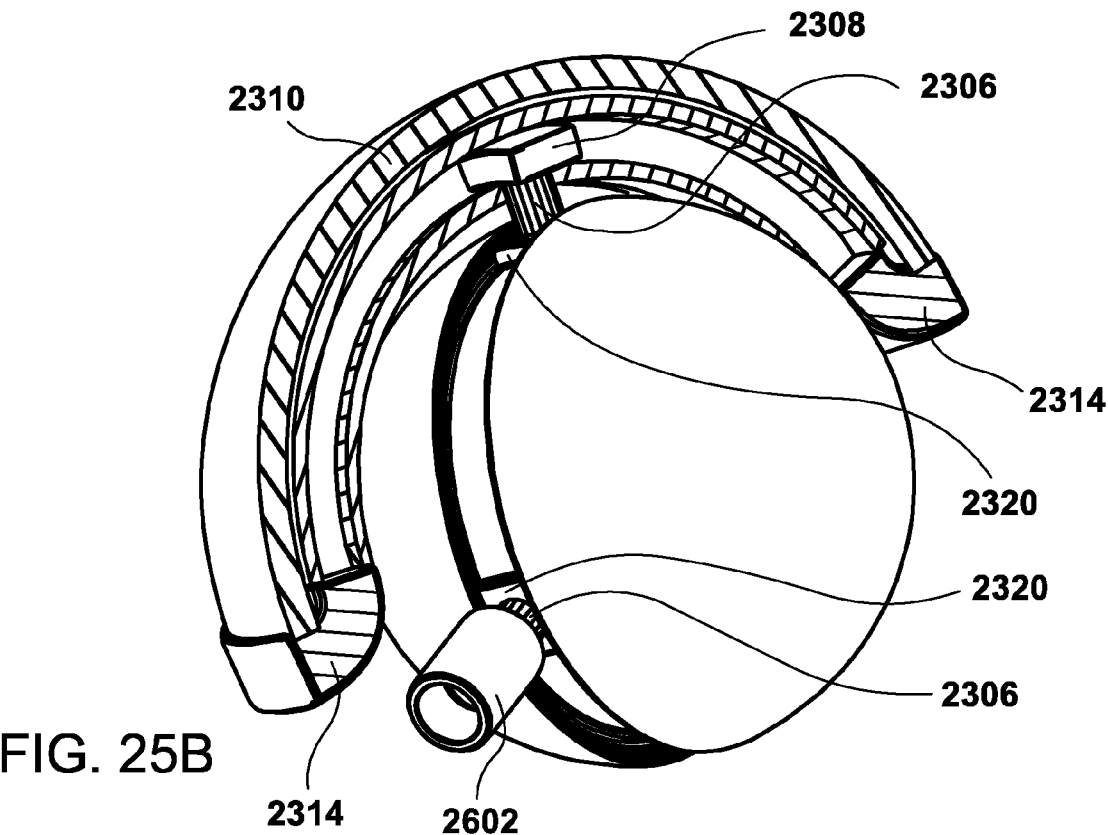
FIG. 25B is a different perspective view of the embodiment of FIG. 25A with the head rotated along various lines.
Figure 25C:
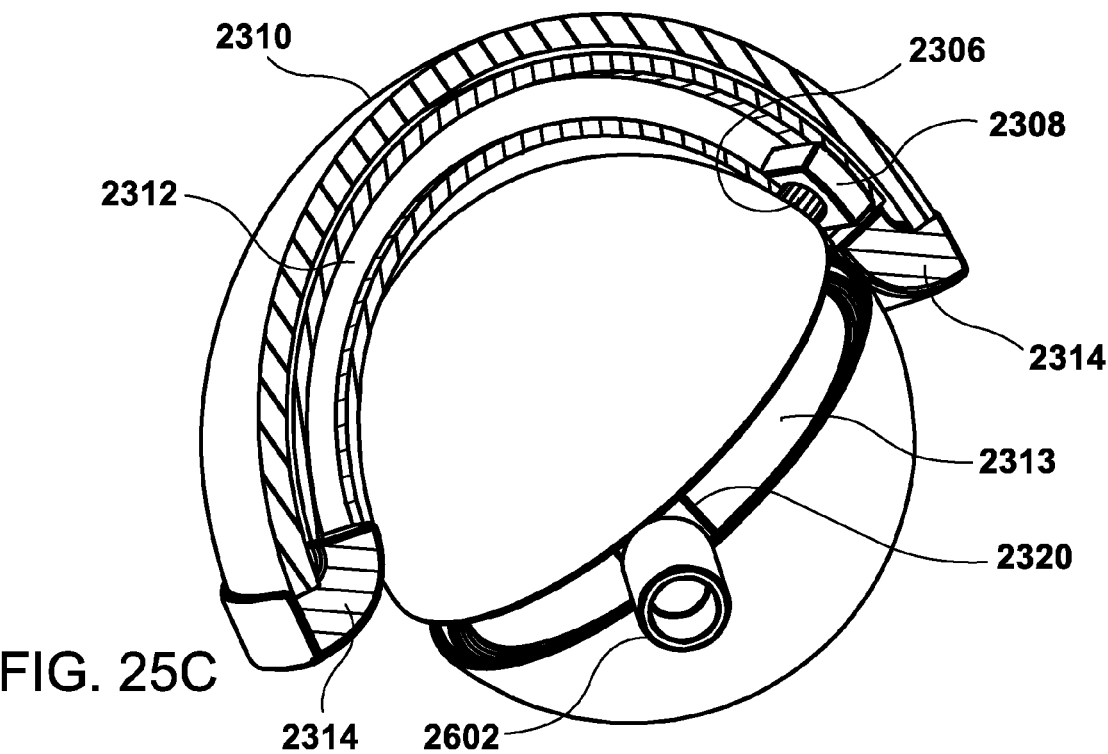
FIG. 25C is a different perspective view of the embodiment of FIG. 25A.

Adding more devices even after two axes of rotation were already created may be used to get extra degrees of rotation (such as by having both the head-bone and the cup-bone each separately attached to cables that insert along the same track (along the same axis of rotation, allowing for possibly more than 180 degrees of rotation along that axis)). (For example, see FIGS. 25A-C, where two knobs are both in a track in the head).

Figure 30A:
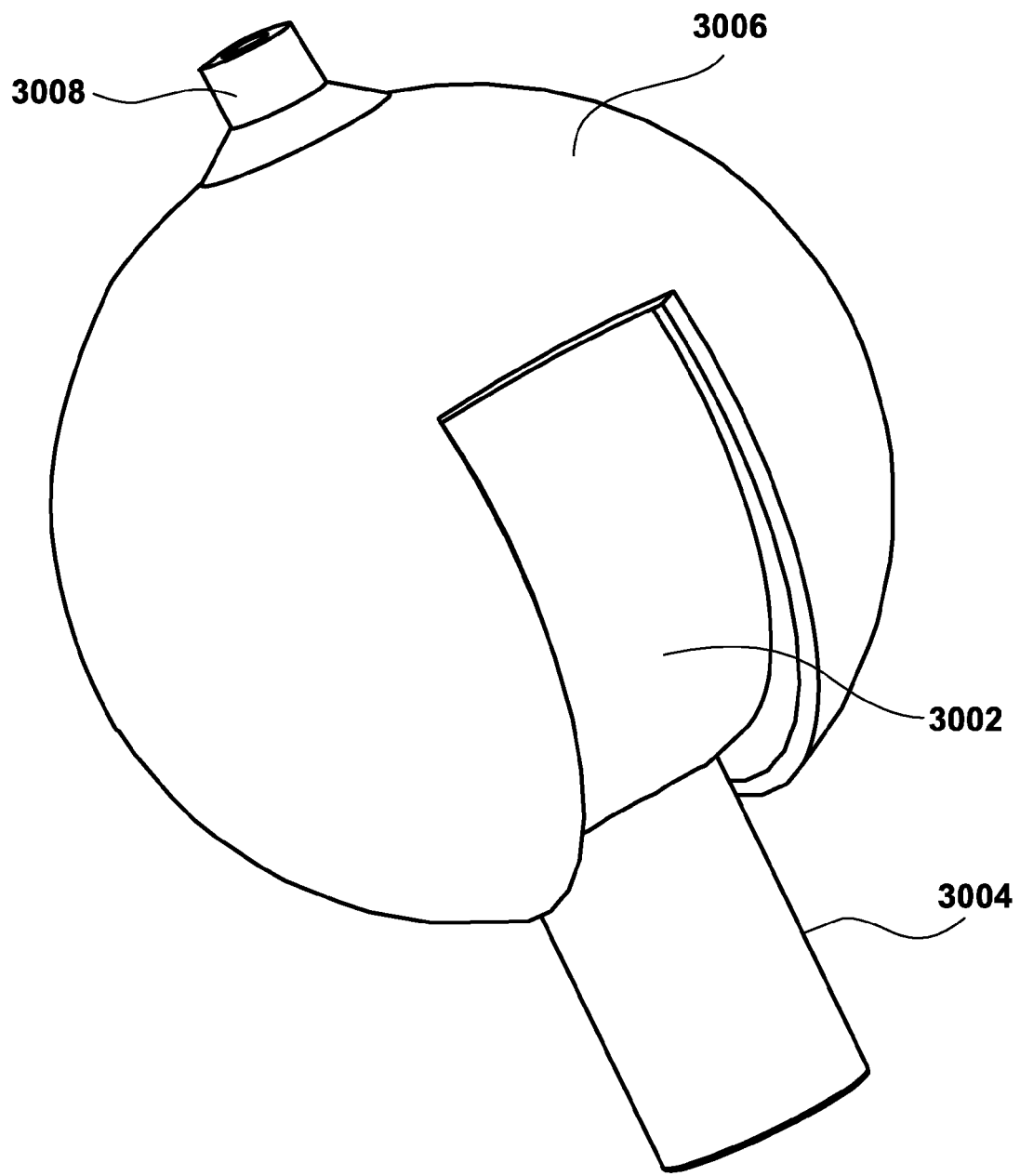
FIG. 30A is a perspective view of an embodiment with swivel with lever attached extending from center.
Figure 30B:
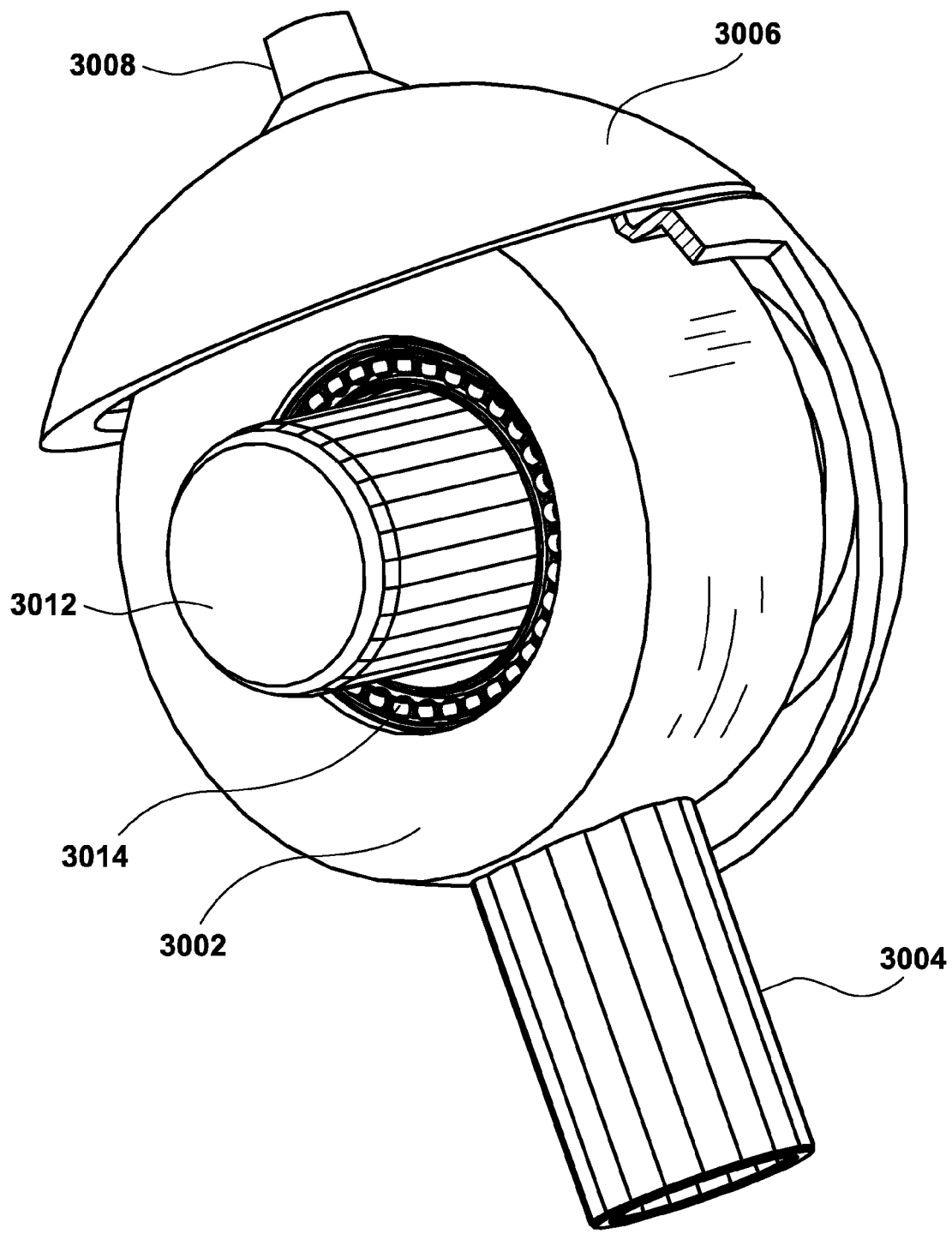
FIG. 30B is a perspective, partial cross section view of the embodiment of FIG. 30A with the head articulated.
Figure 30C:
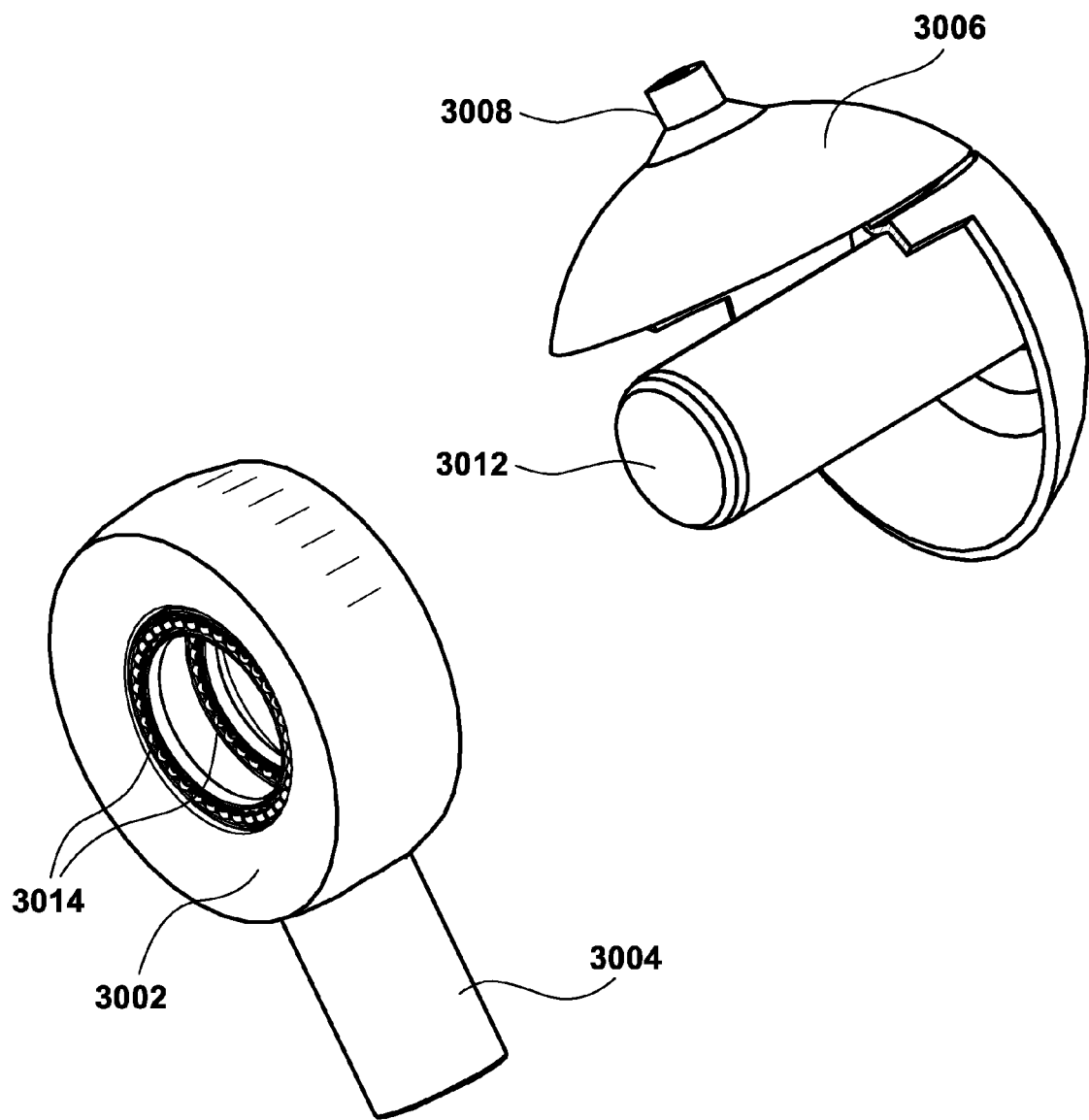
FIG. 30C is a perspective partially exploded view of the embodiment of FIG. 30A.
Figure 31A:
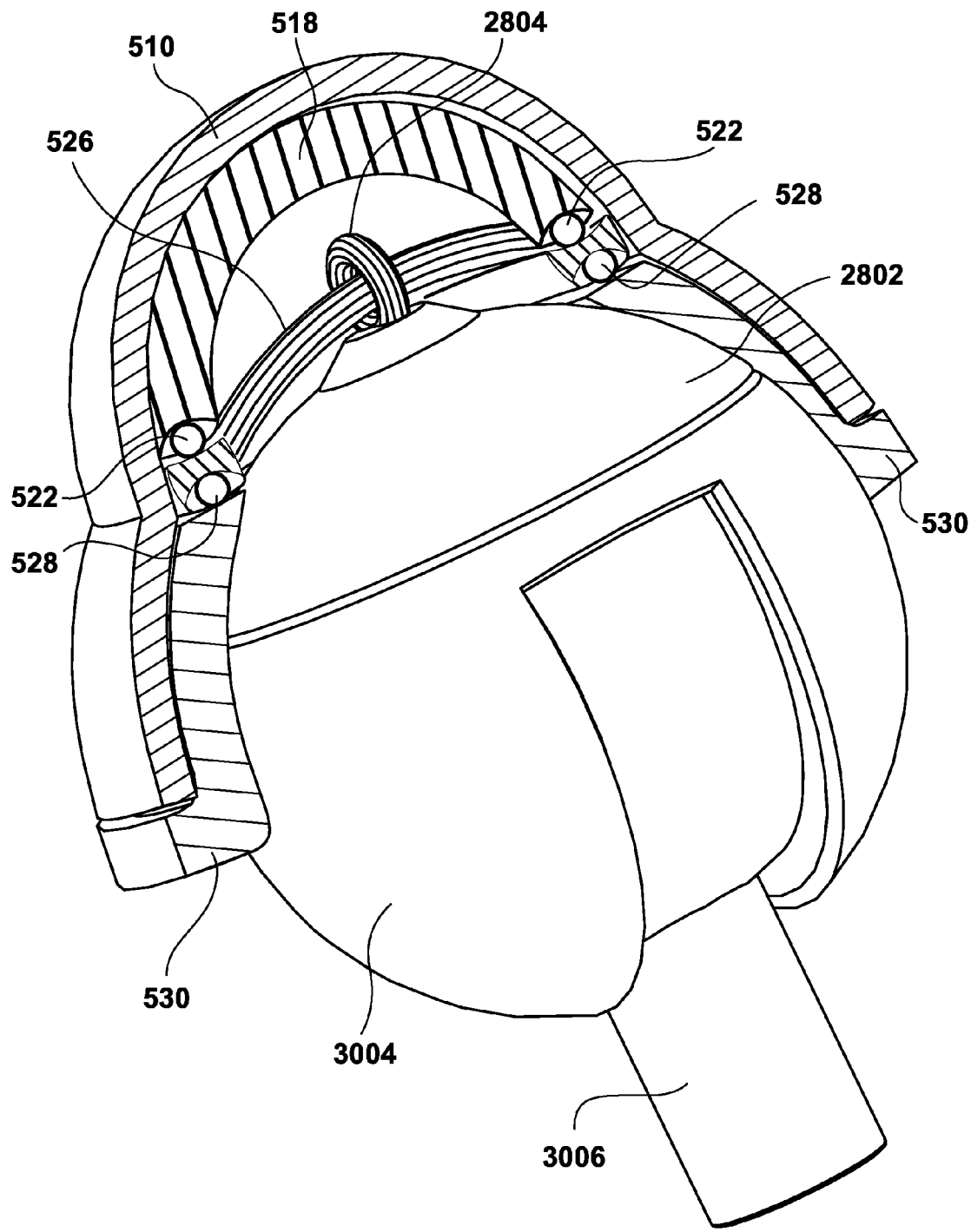
FIG. 31A is a perspective, partial cross section view of an embodiment with an outside track with ring around cable with horizontal swivel and swivel with lever attached extending from center on the opposite side of the head.
Figure 31B:
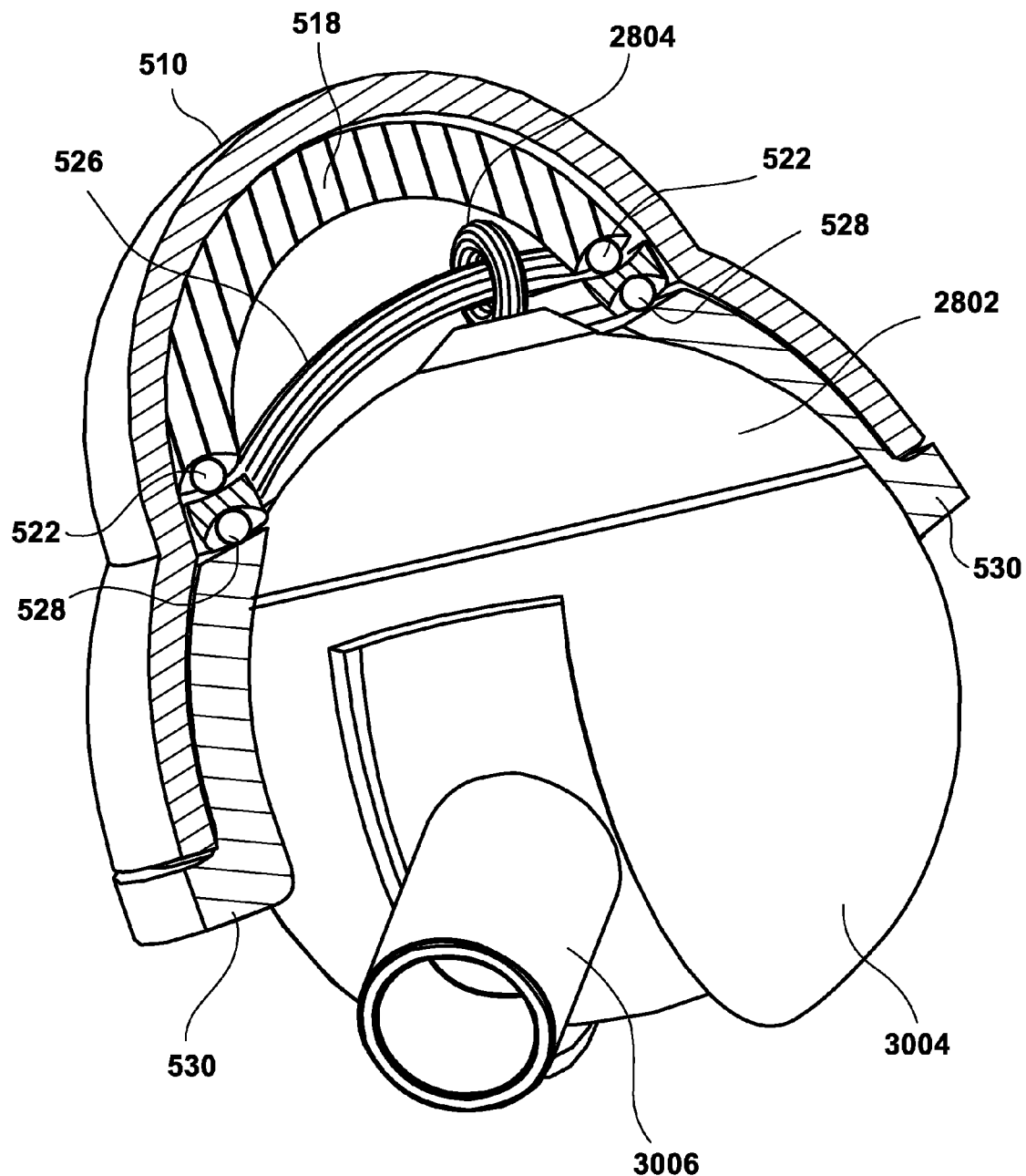
FIG. 31B is a perspective, partial cross section view of the embodiment of FIG. 31A with the head articulated.

Now we'll discuss the preferred embodiment of each device in detail (note that, just as in the cables version, there will be many other embodiments other than the preferred one performing the same functions that are obvious to one of ordinary skill in the art, but do not use all of the details shown by the examples below):

Swivel with Lever:

FIGS. 30A-30C depict the preferred embodiment of a swivel with lever 3004 (see FIGS. 30B-30C for inner parts). A head 3006 (with optional fixed point 3008 on opposite side of head 3006) is adapted to fit a swivel with lever 3004 extending perpendicular to axis of rotation and outward from the center of the head 3006, the swivel comprising the lever 3004 which is rotated by a ring 3002 that rotates about the center portion 3012 attached the head 3006 through ball-bearings 3014. The head 3006 contains a slot so that the lever 3004 can rotate a certain number of degrees without being stopped by the head 3006.

Inside Track:

An inside track is where something is caught within but slides smoothly along a circular track along a fixed radius from the center of the head, and where the fixed point is further away from the center of the head (for instance on the cup) than the track. For example, 1) (see for example, FIG. 27) a dumbbell portion with knob 2320 in track 2313 and stick portion 2306 extending to fixed points at the cup 2702 and on the bottom 2504 (optionally with ball-bearings 2606) (see FIG. 27, two knobs 2320) the inside of the accommodating head 2502 or 2) (see for example, FIG. 29) a ring 2904 around a cable 2906 in a slot 2902 on the inside of the head 2908.

Outside Track:

An outside track is where something is caught within but slides smoothly along a circular track along a fixed radius from the center of the head, and where the fixed point is closer to the center of the head (for instance in the head). For example, 1) (see for example, FIG. 26) a dumbbell portion with knob 2308 in track 2312 and stick portion 2306 extending down towards the center of the accommodating head 2604 (optionally with ball-bearings 2606 and with optional fixed point 2602 on the other side of the accommodating head 2604) or 2) (see, for example, see FIG. 28) a ring 2804 around a cable 526 in a slot 2806 on the accommodating cup 2808.

A horizontal swivel (with an axis perpendicular to that of the two devices) may be created just as in the cables version (see for example FIG. 28). Unlike some of the cables embodiments, a swivel bisecting the head will not interfere with the operation of any cable, because there is none.

As with the cables version, there are many ways of implementing the details of the piecemeal version, such as number of parts (such as more sets of ball-bearings for lever), type of parts (such as using roller-bearings instead of ball-bearings), geometry (does not have to be exact so long as the function of usable head rotation is fulfilled) and any other factor obvious to one of ordinary skill in the art. Of course, parts of versions may be combined when they produce usable head rotation.

Figure 32A:
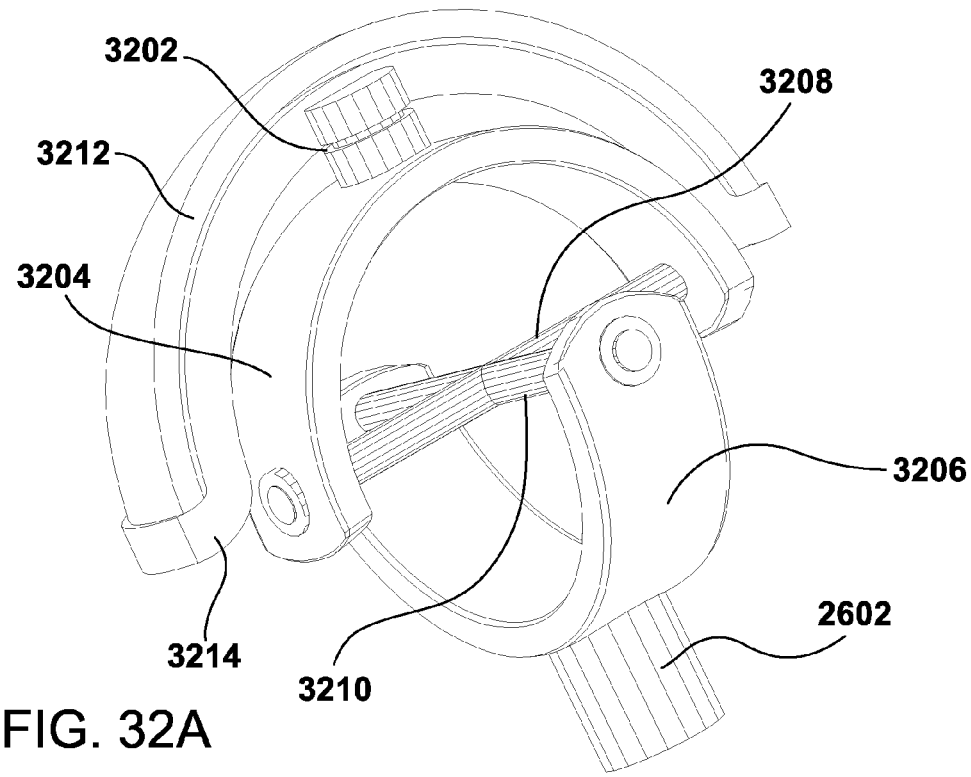
FIG. 32A is a perspective view of an embodiment with a gimbal attached to a horizontal swivel.
Figure 32B:
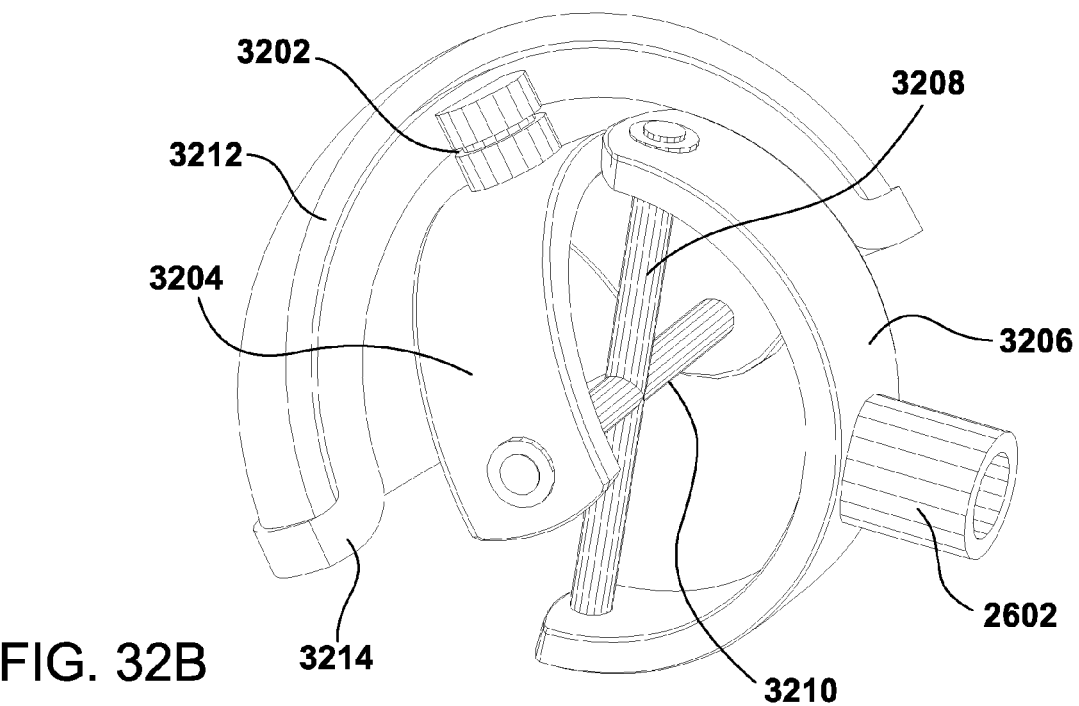
FIG. 32B is a different perspective view of the embodiment of FIG. 32A.

Gimbal Version:

Alternatively to the piecemeal version, two or three axes of rotation may be created through a gimbal for each axis of rotation (optionally the version has a flexible cover). (For example, see FIG. 32). In this preferred embodiment, a rod 3208 runs through another rod 3210 running perpendicular to the first rod, where the ends of the first rod are connected to ball-bearings surrounded by the ends of a C-clamp 3204, and similarly with the second C-clamp 3206, allowing each C-clamp to rotate perpendicularly to the other, creating rotation along two axes, and transferring that ability for example to a cup 106 (with an inner portion 3212 and an outer portion 3214) relative to a fixed point 2602.

Figure 23B:
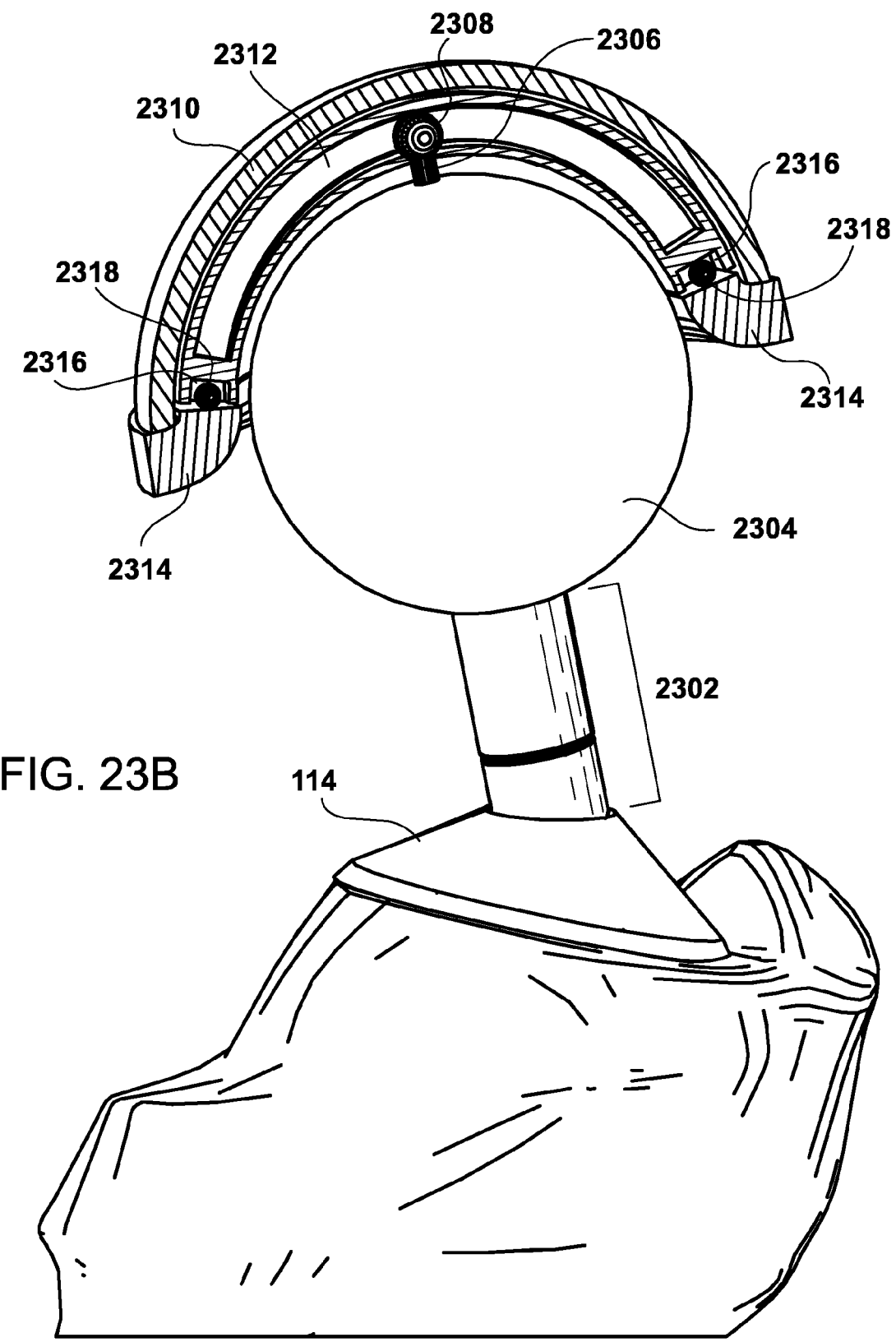
FIG. 23B is a perspective, partial cross section view of the embodiment of FIG. 23A with head articulated.

Weathervane Version:

Additionally, one track combined with a horizontal swivel may create two axes of rotation by acting like a weathervane (for example, see FIGS. 23A-23B). For example, an outside track with a knob (see FIGS. 23A-23B) can rotate along one axis. If the pressure on the left side of the head is different from that on the right side of the accommodating head 2304, then the accommodating head 2304 will swivel more and more until it reaches the point where it is only rotating about the axis of the track 2312. Note the ball-bearings 2318 in the slot 2316, outside of the cup 2310, track 2312, and a piece holding the two together 2314, along with the head 2304, hole-less stem 2302 and head-bone rod 114.

Note that though the inside and outside tracks may be used with a "cup" implanted in the socket of the cup-bone, the inside and outside tracks may also be used with a "cup" attaching to the head-bone.

Assembly of the piecemeal and track versions should be obvious to one of ordinary skill in the art.

The materials used for each embodiment within each version are those commonly used for making artificial hip joints. The inventor has no preference. So long as usable head rotation can be maintained without a certain feature within a combination of features, that feature is optional. Of course, parts of different versions may be combined when they produce usable head rotation. Again, all embodiments and alternatives mentioned above are merely intended to be examples, and are not intended to limit the scope of the invention—one of ordinary skill in the art will know many variations on implementing the details without varying the inventive concepts. Note: The abstract is an oversimplification and does not fully include all versions and all aspects of all versions contemplated. The detailed description incorporates the summary by reference.

What is claimed is:

1. A prosthetic ball and socket apparatus, comprising:
   a) a cup comprising an inner surface wherein a portion of the inner surface running from the cup's equator extending up from the equator to a northern border that runs all of the way around the inner surface at substantially a latitude such that any debris buildup caused by rubbing of a head and the inner surface of the cup against a cup liner does not unduly impair operation of the apparatus nor the patient's health to render the hip implant unsafe to implant, such portion being spherical, and a portion of the inner surface running from the northernmost points of the spherical inner surface to a north pole of the cup is hollowed out super-spherically, said cup fastened to a cup-bone;
   b) the head fitting inside the inner surface of the cup and contacting the spherical portion of the inner surface of the cup through the cup liner, a head-groove in said head;
   c) the cup liner interposed between the head and the spherical portion of the inner surface;
   d) a head to head-bone rod with one end fastened to a head-bone and the other end fastened to substantially a south pole of the head;
   e) the head groove looping approximately longitudinally allowing for walkable head rotation around the head;
   f) a flexible head-cable:
      i) fitting inside the head-groove when the head-cable is between the head and the spherical portion of the inner surface of the cup;
      ii) looping around a cup-cable at a point below the north pole of the inner surface of the cup; and
      iii) looping longitudinally allowing for walkable head rotation around the head, and
   g) the cup-cable:
      i) running parallel allowing for walkable head rotation to a portion of an outer surface of the head above a northern hemisphere of the head;
      ii) running perpendicularly allowing for walkable head rotation to the head-cable; and
      iii) fastened at each end at separate points on the super-spherical portion of the inner surface of the cup.

2. The apparatus of claim 1, wherein the head to head-bone rod has a hole to allow the head-cable to pass through the south pole of the head.

3. The apparatus of claim 1, wherein the spherical inner surface of the cup extends up from the equator to a northern border that runs all of the way around the inner surface at substantially a latitude of 5 degrees northward.

4. The apparatus of claim 3, wherein the head to head-bone rod has a hole to allow the head-cable to pass through the south pole of the head.

5. The apparatus of claim 1, wherein the spherical inner surface of the cup extends up from the equator to a northern border that runs all of the way around the inner surface at substantially a latitude of 10 degrees northward.

6. The apparatus of claim 5, wherein the head to head-bone rod has a hole to allow the head-cable to pass through the south pole of the head.

7. The apparatus of claim 1, wherein the spherical inner surface of the cup extends up from the equator to a northern border that runs all of the way around the inner surface at substantially a latitude of 20 degrees northward.

8. The apparatus of claim 7, wherein the head to head-bone rod has a hole to allow the head-cable to pass through the south pole of the head.

9. The apparatus of claim 1, wherein the spherical inner surface of the cup extends up from the equator to a northern border that runs all of the way around the inner surface at substantially a latitude of 45 degrees northward.

10. The apparatus of claim 9, wherein the head to head-bone rod has a hole to allow the head-cable to pass through the south pole of the head.

11. A prosthetic ball and socket apparatus, comprising:
    a) a cup comprising an inner surface wherein a portion of the inner surface running from the cup's equator extending up from the equator to a northern border that runs all of the way around the inner surface at substantially a latitude such that any debris buildup caused by rubbing of a head and the inner surface of the cup against a cup liner does not unduly impair operation of the apparatus nor the patient's health to render the hip implant unsafe to implant, such portion being spherical, and a portion of the inner surface running from the northernmost points of a spherical inner surface to a north pole of the cup is hollowed out super-spherically, said cup fastened to a cup-bone;
    b) a head fitting inside the inner surface of the cup and contacting the spherical portion of the inner surface of the cup through the cup liner, a head-groove in said head;
    c) the cup liner interposed between the head and the spherical portion of the inner surface;
    d) a head to head-bone rod with one end fastened to a head-bone and the other end fastened to a south pole of the head;
    e) the head groove looping substantially longitudinally around the head;
    f) a flexible head-cable:
       i) fitting inside the head-groove when the head-cable is between the head and the spherical portion of the inner surface of the cup;
       ii) looping around a cup-cable at a point below the north pole of the inner surface of the cup; and
       iii) looping substantially longitudinally around the head, and
    g) the cup-cable:
       i) running substantially parallel to a portion of an outer surface of the head above a northern hemisphere of the head;
       ii) running perpendicular substantially to the head-cable; and
       iii) fastened at each end at separate points on the super-spherical portion of the inner surface of the cup.

12. The apparatus of claim 11, wherein the head to head-bone rod has a hole to allow the head-cable to pass through the south pole of the head.

13. The apparatus of claim 11, wherein the spherical inner surface of the cup extends up from the equator to a northern border that runs all of the way around the inner surface at substantially a latitude of 5 degrees northward.

14. The apparatus of claim 13, wherein the head to head-bone rod has a hole to allow the head-cable to pass through the south pole of the head.

15. The apparatus of claim 11, wherein the spherical inner surface of the cup extends up from the equator to a northern border that runs all of the way around the inner surface at substantially a latitude of 10 degrees northward.

16. The apparatus of claim 15, wherein the head to head-bone rod has a hole to allow the head-cable to pass through the south pole of the head.

17. The apparatus of claim 11, wherein the spherical inner surface of the cup extends up from the equator to a northern border that runs all of the way around the inner surface at substantially a latitude of 20 degrees northward.

18. The apparatus of claim 17, wherein the head to head-bone rod has a hole to allow the head-cable to pass through the south pole of the head.

19. The apparatus of claim 11, wherein the spherical inner surface of the cup extends up from the equator to a northern border that runs all of the way around the inner surface at substantially a latitude of 45 degrees northward.

20. The apparatus of claim 19, wherein the head to head-bone rod has a hole to allow the head-cable to pass through the south pole of the head.

21. A prosthetic ball and socket apparatus, comprising:
  a) a cup comprising an inner surface wherein a portion of the inner surface running from the cup's equator extending up from the equator to a northern border that runs all of the way around the inner surface at substantially a latitude such that any debris buildup caused by rubbing of a head and the inner surface of the cup against a cup liner does not unduly impair operation of the apparatus nor the patient's health to render the hip implant unsafe to implant, such portion being spherical, and a portion of the inner surface running from the northernmost points of a spherical inner surface to a north pole of the cup is hollowed out super-spherically, said cup fastened to a cup-bone;
  b) the head fitting inside the inner surface of the cup and contacting the spherical portion of the inner surface of the cup through the cup liner, a head-groove in said head;
  c) the cup liner interposed between the head and the spherical portion of the inner surface;
  d) a head to head-bone rod with one end fastened to a head-bone and the other end fastened to a south pole of the head;
  e) the head groove looping longitudinally around the head;
  f) a flexible head-cable:
    i) fitting inside the head-groove when the head-cable is between the head and the spherical portion of the inner surface of the cup;
    ii) looping around a cup-cable at a point below the north pole of the inner surface of the cup; and
    iii) looping longitudinally around the head, and
  g) the cup-cable:
    i) running parallel to a portion of an outer surface of the head above a northern hemisphere of the head;
    ii) running perpendicular to the head-cable; and
    iii) fastened at each end at separate points on the super-spherical portion of the inner surface of the cup.

22. The apparatus of claim 21, wherein the head to head-bone rod has a hole to allow the head-cable to pass through the south pole of the head.

23. The apparatus of claim 21, wherein the spherical inner surface of the cup extends up from the equator to a northern border that runs all of the way around the inner surface at substantially a latitude of 5 degrees northward.

24. The apparatus of claim 23, wherein the head to head-bone rod has a hole to allow the head-cable to pass through the south pole of the head.

25. The apparatus of claim 21, wherein the spherical inner surface of the cup extends up from the equator to a northern border that runs all of the way around the inner surface at substantially a latitude of 10 degrees northward.

26. The apparatus of claim 25, wherein the head to head-bone rod has a hole to allow the head-cable to pass through the south pole of the head.

27. The apparatus of claim 21, wherein the spherical inner surface of the cup extends up from the equator to a northern border that runs all of the way around the inner surface at substantially a latitude of 20 degrees northward.

28. The apparatus of claim 27, wherein the head to head-bone rod has a hole to allow the head-cable to pass through the south pole of the head.

29. The apparatus of claim 21, wherein the spherical inner surface of the cup extends up from the equator to a northern border that runs all of the way around the inner surface a substantially a latitude of 45 degrees northward.

* * * * *